United States Patent [19]

Bühlmayer et al.

[11] Patent Number: 4,931,591
[45] Date of Patent: Jun. 5, 1990

[54] NOVEL 5-AMINO-4-HYDROXYVALERYL DERIVATIVES

[75] Inventors: Peter Bühlmayer, Arlesheim; Vittorio Rasetti, Basel; Walter Fuhrer, Lupsingen; James L. Stanton, Basel; Richard Göschl, Bottmingen, all of Switzerland

[73] Assignee: Ciba-Geigy Corporation, Ardsley, N.Y.

[21] Appl. No.: 380,711

[22] Filed: Jul. 12, 1989

Related U.S. Application Data

[60] Continuation of Ser. No. 123,618, Dec. 28, 1987, abandoned, which is a division of Ser. No. 794,914, Nov. 4, 1985, Pat. No. 4,727,060.

[30] Foreign Application Priority Data

Nov. 13, 1984 [CH] Switzerland ................ 5426/84
Jul. 17, 1985 [CH] Switzerland ................ 3094/85

[51] Int. Cl.$^5$ .............. C07C 103/00; C07C 103/20; C07C 103/14; C07C 103/24
[52] U.S. Cl. .................. 564/165; 564/154; 564/157; 564/160; 564/162; 564/188; 564/189; 564/191; 564/197
[58] Field of Search ........... 564/154, 157, 160, 162, 564/165, 188, 189, 191, 197

[56] References Cited

U.S. PATENT DOCUMENTS

| | | | |
|---|---|---|---|
| 4,198,398 | 4/1980 | Hudson et al. | 514/17 |
| 4,304,715 | 12/1981 | Hudson et al. | 530/323 |
| 4,372,974 | 2/1983 | Fish et al. | 514/561 |
| 4,424,207 | 1/1984 | Szelke et al. | 514/15 |
| 4,435,329 | 3/1984 | McEnvoy et al. | 560/10 |
| 4,470,971 | 9/1984 | Boger et al. | 514/15 |
| 4,478,826 | 10/1984 | Veber et al. | 514/16 |
| 4,479,941 | 10/1984 | Veber et al. | 514/17 |
| 4,599,198 | 7/1986 | Hoover et al. | 530/333 |
| 4,609,641 | 9/1986 | Evans et al. | 156/152 |
| 4,609,643 | 9/1986 | Szelke et al. | 514/16 |
| 4,613,676 | 9/1986 | Fuhrer et al. | 560/39 |
| 4,645,759 | 2/1987 | Luly et al. | 514/18 |
| 4,650,661 | 3/1987 | Szelke et al. | 514/16 |
| 4,652,551 | 3/1987 | Luly et al. | 514/18 |
| 4,719,288 | 1/1988 | Fuhrer et al. | 530/331 |
| 4,722,810 | 2/1988 | Delaney et al. | 260/402.5 |
| 4,758,584 | 7/1988 | Buhlymayer et al. | 514/400 |

FOREIGN PATENT DOCUMENTS

| | | |
|---|---|---|
| 104041 | 3/1984 | European Pat. Off. . |
| 152255 | 8/1985 | European Pat. Off. . |
| 156322 | 10/1985 | European Pat. Off. . |
| 173481 | 3/1986 | European Pat. Off. . |
| 212903 | 3/1987 | European Pat. Off. . |
| WO/03044 | 1/1984 | PCT Int'l Appl. . |

OTHER PUBLICATIONS

Rich et al., Tetrahedron Letters, vol. 24, pp. 4401–4404 (1983).
Rich et al., J. Med. Chem., pp. 263–273 (1985).
J. Org. Chem., vol. 50, pp. 4615–4625 (1985).
Rich et al., Peptides: Structure and Function: Proceedings of the 8th American Peptide Symposium, pp. 511–520 (1983).
Szelke et al., Peptides: Structure and Function: Proceedings of the 8th American Peptide Symposium, pp. 579–582 (1983).
Tamara et al., J. Am. Chem. Soc., vol. 106, p. 1079 (1984).
Carroll, J. Chem. Soc., pp. 507–511 (1941).
Kempf, J. Org. Chem., vol. 51, p. 3921 (1986).

*Primary Examiner*—Lester L. Lee
*Attorney, Agent, or Firm*—JoAnn Villamizar

[57] ABSTRACT

Compounds of the formula

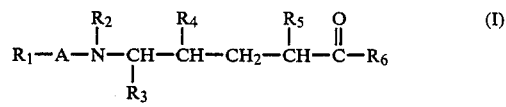

in which $R_1$ represents hydrogen or acyl, A represents an optionally N-alkylated α-amino acid residue which is bonded N-terminally to $R_1$ and C-terminally to the group —$NR_2$—, $R_2$ represents hydrogen or lower alkyl, $R_3$ represents hydrogen, lower alkyl, optionally etherified or esterified hydroxy-lower alkyl, cycloalkyl, cycloalkyl-lower alkyl, bicycloalkyl-lower alkyl, tricycloalkyl-lower alkyl, aryl or aryl-lower alkyl, $R_4$ represents hydroxy or etherified or esterified hydroxy, $R_5$ represents lower alkyl having 2 or more carbon atoms, optionally etherified or esterified hydroxy-lower alkyl, cycloalkyl, cycloalkyl-lower alkyl, bicycloalkyl, bicycloalkyl-lower alkyl, tricycloalkyl, tricycloalkyl-lower alkyl, aryl, aryl-lower alkyl, optionally substituted carbamoyl, optionally substituted amino, optionally substituted hydroxy or optionally substituted mercapto and $R_6$ represents substituted amino, and salts of such compounds having salt-forming groups inhibit the blood pressure-increasing action of the enzyme renin and can be used as antihypertensives.

4 Claims, No Drawings

NOVEL 5-AMINO-4-HYDROXYVALERYL DERIVATIVES

This application is a continuation, of application Ser. No. 123,618, filed Dec. 28, 1987, and now abandoned which is a divisional of application Ser. No. 794,914 filed Nov. 4, 1985 now U.S. Pat. No. 4,727,060.

The invention relates to compounds of the formula

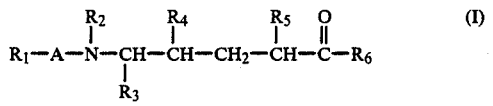

in which $R_1$ represents hydrogen or acyl with the exception of an optionally N-substituted acyl residue of a natural amino acid, A represents an optionally N-alkylated α-amino acid residue which is bonded N-terminally to $R_1$ and C-terminally to the group $-NR_2-$, $R_2$ represents hydrogen or lower alkyl, $R_3$ represents hydrogen, lower alkyl, optionally etherified or esterified hydroxy-lower alkyl, cycloalkyl, cycloalkyl-lower alkyl, bicycloalkyl-lower alkyl, tricycloalkyl-lower alkyl, aryl or aryl-lower alkyl, $R_4$ represents hydroxy or etherified or esterified hydroxy, $R_5$ represents lower alkyl having 2 or more carbon atoms, optionally etherified or esterified hydroxy-lower alkyl, cycloalkyl, cycloalkyl-lower alkyl, bicycloalkyl, bicycloalkyl-lower alkyl, tricycloalkyl, tricycloalkyl-lower alkyl, aryl, aryl-lower alkyl, optionally substituted carbamoyl, optionally substituted amino, optionally substituted hydroxy or optionally substituted mercapto and $R_6$ represents substituted amino with the exception of an amino residue derived from an α-amino acid, and to salts of such compounds having salt-forming groups, processes for their manufacture, pharmaceutical preparations containing these compounds and the use of these compounds as medicaments or for the manufacture of pharmaceutical preparations, and intermediates for the manufacture of compounds of the formula I.

In the description of the present invention the term "lower" used in the definition of groups or radicals, for example lower alkyl, lower alkoxy, lower alkanoyl, etc., denotes that those groups or radicals, unless expressly defined otherwise, contain up to and including 7, and preferably up to and including 4, carbon atoms.

The carbon atoms substituted by $R_3$, $R_4$ and $R_5$ may have the R—, S— or R,S-configuration. Compounds of the formula I in which the carbon atoms substituted by $R_3$ and $R_4$ have the S-configuration are preferred.

The general terms and expressions used in the description of the present invention preferably have the following meanings:

Acyl $R_1$ has, for example, up to 19 carbon atoms and is especially the acyl group of a carboxylic acid, of a semi-ester of carbonic acid, of an optionally N-substituted carbamic acid or thiocarbamic acid, of an optionally N-substituted oxalamide, of a sulphonic acid, or of an optionally N-substituted amidosulphonic acid, for example having the partial formula: $R^b-CO-$, $R^a-O-CO-$, $(R^b)(R^b)N-CO-$, $(R^b)(R^b)N-CS-$, $(R^b)(R^b)N-CO-CO-$, $R^b-SO_2-$ or $(R^b)(R^b)N-SO_2-$ in which $R^a$ represents an unsubstituted or substituted, saturated or unsaturated aliphatic, cycloaliphatic or cycloaliphatic-aliphatic hydrocarbon radical having up to an including 18, preferably up to and including 10, carbon atoms, or an unsubstituted or substituted aromatic, heteroaromatic, aromatic-aliphatic or heteroaromatic-aliphatic hydrocarbon radical having up to and including 18, preferably up to and including 10, carbon atoms, or an unsubstituted or substituted saturated five- or six-membered heterocycle, and $R^b$ represents hydrogen or has the meanings of $R^a$. In groups in which $R^b$ occurs twice, the two radicals $R^b$ may be the same or different.

An acyl residue of an optionally N-substituted natural amino acid is excluded from being acyl $R_1$.

An unsubstituted or substituted, saturated or unsaturated aliphatic, cycloaliphatic or cycloaliphaticaliphatic hydrocarbon radical $R^a$ or $R^b$ is, for example, unsubstituted or substituted alkyl, for example lower alkyl, lower alkenyl, lower alkynyl, mono-, bi- or tri-cycloalkyl, monocycloalkenyl, bicycloalkenyl, cycloalkyl-lower alkyl, cycloalkyl-lower alkenyl or cycloalkenyl-lower alkyl.

Alkyl $R^a$ or $R^b$ preferably has from 1 to 10 carbon atoms and is, for example, optionally substituted lower alkyl having from 1 to 7 carbon atoms or n-octyl, n-nonyl or n-decyl.

Lower alkyl $R^a$ or $R^b$ preferably has from 1 to 7 carbon atoms and is, for example, methyl, ethyl, n-propyl, isopropyl, n-butyl or tert.-butyl, each of which may be substituted by one or more functional groups, for example hydroxy, etherified hydroxy, for example lower alkoxy, such as methoxy or ethoxy, or phenoxy, esterified hydroxy, for example lower alkanoyloxy, such as acetoxy, halogen, for example chlorine or bromine, hydroxy-sulphonyloxy, carboxy, esterified carboxy, for example lower alkoxycarbonyl, such as methoxy- or ethoxy-carbonyl, amidated carboxy, for example carbamoyl or mono- or di-lower alkylcarbamoyl, such as methyl- or dimethyl-carbamoyl, cyano, phosphono, esterified phosphono, for example di-lower alkoxyphosphoryl, such as dimethoxy- or diethoxyphosphoryl, amino, or by oxo, the substituents being in the 1-position of the lower alkyl radical only if that radical in the partial formula $R^b-CO-$ is bonded to the carbonyl group.

Monosubstituted lower alkyl $R^a$ or $R^b$ is, for example, hydroxy-lower alkyl, for example 2-hydroxyethyl, lower alkoxy-lower alkyl, for example lower alkoxymethyl or lower alkoxyethyl, such as methoxymethyl or 2-methoxyethyl, phenoxy-lower alkyl, for example phenoxymethyl, naphthoxy-lower alkyl, for example α- or β-naphthoxymethyl, lower alkanoyloxy-lower alkyl, for example lower alkanoyloxymethyl or lower alkanoyloxyethyl, such as acetoxymethyl or 2-acetoxyethyl, halo-lower alkyl, for example halomethyl or haloethyl, such as 2-chloro- or 2-bromo-ethyl, hydroxysulphonyloxy-lower alkyl, for example hydroxysulphonyloxymethyl or 2-hydroxysulphonyloxyethyl, carboxy-lower alkyl, for example carboxymethyl or 2-carboxyethyl, lower alkoxycarbonyl-lower alkyl, for example lower alkoxycarbonylmethyl or lower alkoxycarbonylethyl, such as methoxycarbonylmethyl, 2-methoxycarbonylethyl, ethoxycarbonylmethyl or 2-ethoxycarbonylethyl, carbamoyl-lower alkyl, for example carbamoylmethyl or 2-carbamoylethyl, lower alkylcarbamoyl-lower alkyl, for example methylcarbamoylmethyl, di-lower alkylcarbamoyl-lower alkyl, for example dimethylcarbamoylmethyl, cyano-lower alkyl, for example cyanomethyl or 2-cyanoethyl, or oxo-lower alkyl, for example 2-oxopropyl or 2-oxobutyl.

Substituted lower alkyl $R^a$ or $R^b$ having two or more substituents is, for example, hydroxy-carboxy-lower alkyl, for example hydroxy-carboxy-methyl or 1-hydroxy-2-carboxy-ethyl, hydroxy-lower alkoxycarbonyl-lower alkyl, for example hydroxy-ethoxy- or -methoxycarbonyl-ethyl, esterified hydroxy-lower alkoxycarbonyl-lower alkyl, for example acetoxy-methoxycarbonyl-methyl-, dihydroxy-carboxy-lower alkyl, for example 1,2-dihydroxy-2-carboxy-ethyl, dihydroxy-lower alkoxycarbonyl-lower alkyl, for example 1,2-dihydroxy-2-ethoxy- or -methoxy-carbonyl-ethyl, esterified dihydroxy-lower alkoxycarbonyl-lower alkyl, for example 1,2-diacetoxy-2-ethoxy- or -methoxy-carbonyl-ethyl, α-naphthoxy-carboxy-lower alkyl, for example 1-α-naphthoxy-3-carboxy-propyl, α-naphthoxy-lower alkoxycarbonyl-lower alkyl, for example α-naphthoxyethoxycarbonyl-methyl, 1-α-naphthoxy-2-ethoxycarbonylethyl or 1-α-naphthoxy-3-tert.-butoxycarbonylpropyl, α-naphthoxy-benzyloxycarbonyl-lower alkyl, for example 1-α-naphthoxy-2-benzyloxycarbonyl-ethyl, α-naphthoxycarbamoyl-lower alkyl, for example 1-α-naphthoxy-3-carbamoyl-propyl, α-naphthoxy-cyano-lower alkyl, for example α-naphthoxy-cyano-methyl or 1-α-naphthoxy-3-cyano-propyl, α-naphthoxy-di-lower alkylamino-lower alkyl, for example 1-α-naphthoxy-4-dimethylamino-butyl, or α-naphthoxy-oxo-lower alkyl, for example 1-α-naphthoxy-3-oxo-butyl.

Lower alkenyl $R^a$ or $R^b$ contains, for example, from 2 to 7, especially from 2 to 4, carbon atoms, the double bond being in the 1-position of the lower alkenyl radical only if that radical in the partial formula $R^b$—CO— is bonded to the carbonyl group, and is, for example, vinyl, allyl or 2- or 3-butenyl. Lower alkenyl $R^a$ or $R^b$ may be substituted by the same substituents as may lower alkyl, for example by hydroxy, etherified hydroxy, for example methoxy, esterified hydroxy, for example acetoxy, halogen, for example chlorine or bromine, carboxy, esterified carboxy, for example methoxycarbonyl or ethoxycarbonyl, or by amidated carboxy, for example carbamoyl.

Lower alkynyl $R^a$ or $R^b$ contains, for example, from 2 to 7, especially from 2 to 4, carbon atoms and is, for example ethynyl, 1-propynyl or 2-propynyl.

Cycloalkyl $R^a$ or $R^b$ contains, for example, from 3 to 8, especially from 3 to 6, carbon atoms and is, for example cyclopropyl, cyclobutyl, cyclopentyl or cyclohexyl.

Bicycloalkyl $R^a$ or $R^b$ contains, for example, from 5 to 10, especially from 6 to 9, carbon atoms and is, for example, bicyclo-hexyl, -heptyl, -octyl, -nonyl or -decyl, for example bicyclo[3.1.0]hex-1-, -2- or -3-yl, bicyclo[4.1.0]hept-1- or -4-yl, bicyclo[2.2.1]-hept-2-yl, for example endo- or exo-norbornyl, bicyclo[3.2.1]oct-2-yl, bicyclo[3.3.0]oct-3-yl or bicyclo[3.3.1]non-9-yl, also α- or β-decahydronaphthyl.

Tricycloalkyl $R^a$ or $R^b$ contains, for example, from 8 to 10 carbon atoms and is, for example, tricyclo[5.2.1.0$^{2,6}$]dec-8-yl or adamantyl, such as 1-adamantyl.

Cycloalkenyl $R^a$ or $R^b$ contains, for example, from 3 to 8, especially from 3 to 6, carbon atoms and is, for example, cyclohexenyl, for example 1-cyclohexenyl, or cyclohexadienyl, for example 1,4-cyclohexadienyl.

Bicycloalkenyl $R^a$ or $R^b$ contains, for example, from 5 to 10, especially from 7 to 10, carbon atoms and is, for example, bicyclo[2.2.1]hept-5-en-yl, for example 5-norbornen-2-yl, bicyclo[2.2.2]octen-2-yl or hexahydro-4,7-methanoind-1-en-6-yl.

Cycloalkyl-lower alkyl $R^a$ or $R^b$ contains, for example, from 4 to 10, especially from 4 to 7, carbon atoms and is, for example, cyclopropylmethyl, cyclobutylmethyl, cyclopentylmethyl or cyclohexylmethyl.

Cycloalkyl-lower alkenyl $R^a$ or $R^b$ contains, for example, from 5 to 10, especially from 5 to 9, carbon atoms and is, for example, cyclohexylvinyl or cyclohexylallyl.

Cycloalkenyl-lower alkyl $R^a$ or $R^b$ contains, for example, from 4 to 10, especially from 4 to 7, carbon atoms and is, for example 1-cyclohexenylmethyl or 1,4-cyclohexadienylmethyl.

The cycloaliphatic or cycloaliphatic-aliphatic radicals mentioned may be substituted by the same substituents as may lower alkyl $R^a$.

An optionally substituted aromatic or aromatic-aliphatic hydrocarbon radical $R^a$ or $R^b$ is, for example, unsubstituted or substituted aryl, aryl-lower alkyl or aryl-lower alkenyl.

Aryl $R^a$ or $R^b$ contains, for example, from 6 to 14 carbon atoms and is, for example, phenyl, indenyl, for example 2- or 4-indenyl, 1- or 2-naphthyl, anthryl, for example 1- or 2-anthryl, phenanthryl, for example 9-phenanthryl, or acenaphthenyl, for example 1-acenaphthenyl. Aryl $R^a$ or $R^b$ is substituted, for example, by lower alkyl, for example methyl, hydroxy, lower alkoxy, for example methoxy, acyloxy, for example lower alkanoyloxy, such as acetoxy, amino, lower alkylamino, for example methylamino, di-lower alkylamino, for example dimethylamino, acylamino, for example tert.-butoxycarbonylamino, or halogen, for example chlorine, bromine or iodine, it being possible for the substituent to be in any position in the aryl radical, for example in the o-, m- or p-position of the phenyl radical, and it also being possible for the aryl radical to be polysubstituted by the same or different substituents.

Aryl-lower alkyl $R^a$ or $R^b$ has, for example, from 7 to 15 carbon atoms and contains, for example, an unsubstituted or substituted, optionally branched radical mentioned under lower alkyl $R^a$ or $R^b$ and an unsubstituted or substituted radical mentioned under aryl $R^a$ or $R^b$. Such an aryl-lower alkyl radical is, for example, benzyl, lower alkylbenzyl, such as 4-methylbenzyl, lower alkoxybenzyl, such as 4-methoxybenzyl, substituted anilinobenzyl, such as 2-(o,o-dichloroanilino)-benzyl or 2-(o,o-dichloro-N-benzylanilino)-benzyl, 2-phenylethyl, 2-(p-hydroxyphenyl)-ethyl, diphenylmethyl, di-(4-methoxyphenyl)-methyl, trityl, α- or β-naphthylmethyl, or 2-(α- or β-naphthyl)-ethyl, also 2-phenylethyl, 3-phenyl-2-propyl, 4-phenyl-3-butyl, 2-α-naphthylethyl, 3-α-naphthyl-2-propyl or 4-α-naphthyl-3-butyl, each of which is substituted in the 1-position by hydroxy, lower alkoxy, for example neopentyloxy, acyloxy, for example acetoxy, pivaloyloxy, ethylaminocarbonyloxy, 2-benzyloxycarbonylamino-2-methylpropionoxy, 2-amino-2-methylpropionoxy or acetoacetoxy, carboxy, esterified carboxy, for example benzyloxycarbonyl, tert.-butoxycarbonyl or ethoxycarbonyl, carbamoyl, substituted carbamoyl, for example tert.-butylcarbamoyl, carboxymethylcarbamoyl, tert.-butoxycarbonylmethylcarbamoyl, 2-dimethylaminoethylcarbamoyl, 3-hydroxy-2-propylcarbamoyl, 2,2-dimethoxyethylcarbamoyl or 5-amino-5-carboxypentylcarbamoyl, cyano, phosphono, esterified phosphono, for example diethoxyphosphoryl, dimethoxyphosphoryl or hydroxymethoxyphosphoryl, or by oxo, also 1-phenyl- or α-naphthyl-4-oxo-2-pentyl, 1-phenyl- or α-naphthyl-5,5-dimethyl-4-oxo-2-hexyl, 1-phenyl- or α-naphthyl-4,4-dimethyl-3-oxo-2-pentyl, 1-phenyl-4-(2-benzofuranyl)-4-oxo-butyl, 1-phenyl- or α-naphthyl-5-dimethylamino-2-pentyl, 1-phenyl- or α-naphthyl-5-dimethylamino-4-oxo-2-pentyl, 1-phenyl- or α-naphthyl-3-dimethylamino-2-propyl, α,p-diaminobenzyl or α,p-diacylaminobenzyl, for example α,p-dibenzyloxycarbonylaminobenzyl or α-pivaloylamino-p-benzyloxycarbonylaminobenzyl.

Aryl-lower alkenyl $R^a$ or $R^b$ has, for example, from 8 to 16 carbon atoms and contains, for example, an unsubstituted or substituted radical mentioned under lower alkenyl $R^a$ or $R^b$ and an unsubstituted or substituted radical mentioned under aryl $R^a$ or $R^b$. Such an aryl-lower alkenyl radical is, for example, styryl, 3-phenylallyl, 2-(α-naphthyl)-vinyl or 2-(β-naphthyl)-vinyl.

In a heteroaromatic or heteroaromatic-aliphatic hydrocarbon radical $R^a$ or $R^b$ the heterocycle is mono-, bi- or tri-cyclic and contains one or two nitrogen atoms and/or an oxygen or sulphur atom and is linked by one of its ring carbon atoms to the group —CO— or —O—CO—, >N—CO—, >N—CS—, >N—CO—CO—, —SO$_2$— or >N—CO$_2$—. Such a heteroaryl radical $R^a$ or $R^b$ is, for example, pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl or a benzo-annellated or cyclopenta-, cyclohexa- or cyclohepta-annellated derivative of those radicals. This heterocycle may be partially saturated and, at a nitrogen atom, it may be substituted by lower alkyl, for example methyl or ethyl, phenyl, or phenyl-lower alkyl, for example benzyl, and/or, at one or more carbon atoms, it may be substituted by lower alkyl, for example methyl, phenyl, phenyl-lower alkyl, for example benzyl, halogen, for example chlorine, hydroxy, lower alkoxy, for example methoxy, phenyl-lower alkoxy, for example benzyloxy, or by oxo, and is, for example, 2- or 3-pyrrolyl, phenyl-pyrrolyl, for example 4- or 5-phenyl-2-pyrrolyl, 2-furyl, 2-thienyl, 4-imidazolyl, 2-, 3- or 4-pyridyl, 2-, 3- or 5-indolyl, substituted 2-indolyl, for example 1-methyl-, 5-methyl-, 5-methoxy-, 5-benzyloxy-, 5-chloro- or 4,5-dimethyl-2-indolyl, 1-benzyl-2- or -3-indolyl, 4,5,6,7-tetrahydro-2-indolyl, cyclohepta-[b]-5-pyrrolyl, 2-, 3- or 4-quinolyl, 4-hydroxy-2-quinolyl, 1-, 3- or 4-isoquinolyl, 1-oxo-1,2-dihydro-3-isoquinolyl, 2-quinoxalinyl, 2-benzofuranyl, 2-benzoxazolyl, 2-benzothiazolyl, benz[e]indol-2-yl or β-carbolin-3-yl.

A heteroaromatic-aliphatic hydrocarbon radical $R^a$ or $R^b$ contains, for example, an unsubstituted or substituted radical mentioned under lower alkyl $R^a$ or $R^b$ and an unsubstituted or substituted radical mentioned under heteroaryl $R^a$ or $R^b$ and is, for example, 2- or 3-pyrrolylmethyl, 2-, 3- or 4-pyridylmethyl, 2-(2-, 3- or 4-pyridyl)-ethyl, 4-imidazolylmethyl, 2-(4-imidazolyl)-ethyl, 2- or 3-indolylmethyl, 2-(3-indolyl)-ethyl or 2-quinolyl-methyl.

A saturated five- or six-membered heterocycle $R^a$ or $R^b$ has as ring members at least one carbon atom, from 1 to 3 nitrogen atoms and optionally an oxygen or a sulphur atom and is linked by one of its ring carbon atoms to the group —CO— or —OCO—, >N—CO—, >N—CS—, >N—CO—CO—, —SO$_2$— or >N—SO$_2$—. This heterocycle may be substituted at one of its carbon atoms or at a ring nitrogen atom by lower alkyl, for example methyl or ethyl, phenyl or phenyl-lower alkyl, for example benzyl, or at one of its carbon atoms by hydroxy or oxo, and/or it may be benzoannellated at two adjacent carbon atoms.

Such a heterocycle is, for example, pyrrolidin-3-yl, hydroxypyrrolidin-2- or -3-yl, for example 4-hydroxypyrrolidin-2-yl, oxopyrrolidin-2-yl, for example 5-oxopyrrolidin-2-yl, piperidin-2- or -3-yl, 1-lower alkyl-piperidin-2-, -3- or -4-yl, for example 1-methylpiperidin-2-, -3- or -4-yl, morpholin-2- or -3-yl, thiomorpholin-2- or -3-yl, and/or 4-lower alkylpiperazin-2- or -3-yl, for example 1,4-dimethylpiperazin-2-yl indolinyl, for example 2- or 3-indolinyl, 1,2,3,4-tetrahydroquinolyl, for example 1,2,3,4-tetrahydroquinol-2-, -3- or -4-yl or 1,2,3,4-tetrahydroisoquinolyl, for example 1,2,3,4-tetrahydroisoquinol-1-, -3- or -4-yl or 1-oxo-1,2,3,4-tetrahydroisoquinol-3-yl Excluded as heterocycle $R^b$ in an acyl radical $R^b$—CO— is optionally N-substituted pyrrolidin-2-yl, that is to say the residue of the amino acid proline.

Preferred acyl groups $R_1$ are, for example, alkanoyl, for example n-decanoyl, or lower alkanoyl, for example formyl, acetyl, propionyl or pivaloyl, hydroxy-lower alkanoyl, for example β-hydroxypropionyl, lower alkoxy-lower alkanoyl, for example lower alkoxyacetyl or lower alkoxypropionyl, such as methoxyacetyl or β-methoxypropionyl, phenoxy-lower alkanoyl, for example phenoxyacetyl, naphthoxy-lower alkanoyl, for example α- or β-naphthoxyacetyl, lower alkanoyloxy-lower alkanoyl, for example lower alkanoxyloxyacetyl or lower alkanoyloxypropionyl, such as acetoxyacetyl or β-acetoxypropionyl, halo-lower alkanoyl, for example α-haloacetyl, such as α-chloro-, α-bromo-, α-iodo- or α,α,α,-trichloro-acetyl, or halopropionyl, such as β-chloro- or β-bromo-propionyl, carboxy-lower alkanoyl, for example carboxyacetyl or β-carboxypropionyl, lower alkoxycarbonyl-lower alkanoyl, for example lower alkoxycarbonylacetyl or lower alkoxycarbonylpropionyl, such as methoxycarbonylacetyl, β-methoxycarbonylpropionyl, ethoxycarbonylacetyl or β-ethoxycarbonylpropionyl, carbamoyl-lower alkanoyl, for example carbamoylacetyl or β-carbamoylpropionyl, lower alkylcarbamoyl-lower alkanoyl, for example methylcarbamoylacetyl, di-lower alkylcarbamoyl-lower alkanoyl, for example dimethylcarbamoylacetyl, oxo-lower alkanoyl, for example acetoacetyl or propionylacetyl, hydroxycarboxy-lower alkanoyl, for example α-hydroxy-α-carboxy-acetyl or α-hydroxy-β-carboxy-propionyl, hydroxy-lower alkoxycarbonyl-lower alkanoyl, for example α-hydroxy-α-ethoxy- or -methoxy-carbonyl-acetyl or α-hydroxy-β-ethoxy- or -methoxy-carbonyl-propionyl, esterified hydroxy-lower alkoxycarbonyl-lower alkanoyl, for example α-acetoxy-α-methoxycarbonyl-acetyl, dihydroxycarboxy-lower alkanoyl, for example α,β-dihydroxy-β-carboxy-propionyl, dihydroxy-lower alkoxycarbonyl-lower alkanoyl, for example α,β-dihydroxy-β-ethoxy- or -methoxy-carbonyl-propionyl, esterified dihydroxy-lower alkoxycarbonyl-lower alkanoyl, for example α,β-diacetoxy-β-methoxycarbonylpropionyl, α-naphthoxy-carboxy-lower alkanoyl, for example 2-α-naphthoxy-4-carboxy-butyryl, α-naphthoxylower alkoxycarbonyl-lower alkanoyl, for example α-naphthoxy-ethoxycarbonyl-acetyl, 2-α-naphthoxy-3-ethoxycarbonyl-propionyl or 2-α-naphthoxy-4-tert.-butoxycarbonyl-butyryl, α-naphthoxy-benzyloxycarbonyl-lower alkanoyl, for example 2-α-naphthoxy-3-benzyloxycarbonyl-propionyl, α-naphthoxy-carbamoyl-lower alkanoyl, for example 2-α-naphthoxy-4-carbamoylbutyryl, α-naphthoxy-cyano-lower alkanoyl, for example α-naphthoxy-cyano-acetyl or 2-α-naphthoxy-4-cyanobutyryl, α-naphthoxy-di-lower alkylamino-lower alkanoyl, for example 2-α- naphthoxy-5-dimethylaminopentanoyl, α-naphthoxy-oxo-lower alkanoyl, for example 2-α-naphthoxy-4-oxopentanoyl, lower alkenoyl, for example acryloyl, vinylacetyl, crotonoyl or 3- or 4-pentenoyl, lower alkynoyl, for example propiolyl or 2- or 3-butynoyl, cycloalkylcarbonyl, for example cyclopropyl-, cyclobutyl-, cyclopentyl- or cyclohexylcarbonyl, bicycloalkylcarbonyl, for example endo- or exo-norbornyl-2-carbonyl, bicyclo[2.2.2]oct-2-ylcarbonyl or bicyclo[3.3.1]non-9-ylcarbonyl, tricycloalkylcarbonyl, for example 1- or 2-adamantylcarbonyl, cycloalkenylcarbonyl, for example 1-cyclohexenylcarbonyl or 1,4-cyclohexadienylcarbonyl, bicycloalkenylcarbonyl, for example 5-norbornen-2-ylcarbonyl or bicyclo[2.2.2]octen-2-ylcarbonyl, cycloalkyl-lower alkanoyl, for example cyclopropylacetyl, cyclopentylacetyl or cyclohexylacetyl, cycloalkyl-lower alkenoyl, for example cyclohexylacryloyl, cycloalkenyl-lower alkanoyl, for example 1-cyclohexenylacetyl or 1,4-cyclohexadienylacetyl, benzoyl unsubstituted or mono-or poly-substituted by lower alkyl, for example methyl, halogen, for example chlorine, hydroxy, lower alkoxy, for example methoxy, and/or by nitro, for example 4-chloro-, 4-methoxy- or 4-nitro-benzoyl, also phenyl-, α-naphthyl- or β-naphthyl-lower alkanoyl in which phenyl may be unsubstituted or mono- or poly-substituted by lower alkyl, for example methyl, halogen, for example chlorine, hydroxy, lower alkoxy, for example methoxy, and/or by nitro and in which lower alkanoyl may be unsubstituted or substituted, for example, by hydroxy, lower alkoxy, acyloxy, carboxy, esterified carboxy, carbamoyl, substituted carbamoyl, cyano, phosphono, esterified phosphono, benzofuranyl and/or by oxo and is optionally branched, for example phenylacetyl, α-naphthylacetyl, β-naphthylacetyl, lower alkylphenylacetyl, such as 4-methylphenylacetyl, lower alkoxyphenylacetyl, such as 4-methoxyphenylacetyl, 3-phenylpropionyl, 3-(p-hydroxyphenyl)-propionyl, diphenylacetyl, di-(4-methoxyphenyl)-acetyl, triphenylacetyl, substituted anilinophenylacetyl, such as 2-(o,o-dichloroanilino)-phenylacetyl or 2-(o,o-dichloro-N-benzylanilino)-phenylacetyl, 3-α- or -β-naphthylpropionyl, 3-phenyl- or 3-α-naphthyl-2-hydroxypropionyl, 3-phenyl- or 3-α-naphthyl-2-lower alkoxypropionyl, such as 3-phenyl- or 3-α-naphthyl-2-neopentyloxy-propionyl, 3-phenyl- or 3-α-naphthyl2-acyloxy-propionyl, such as 3-phenyl-2-pivaloyloxy- or -2-acetoxy-propionyl, 3-α-naphthyl-2-pivaloyloxy- or -2-acetoxy-propionyl, 3-α-naphthyl-2-acetoacetoxypropionyl, 3-α-naphthyl-2-ethylaminocarbonyloxypropionyl or 3-α-naphthyl-2-(2-amino- or 2-benzyloxycarbonylamino-2-methylpropionyloxy)-propionyl, 3-phenyl- or 3-α-naphthyl-2-carboxymethylpropionyl, 3-phenyl- or 3-α-naphthyl-2-lower alkoxycarbonylpropionyl, such as 3-α-naphthyl-2-ethoxycarbonylpropionyl, 3-phenyl- or 3-α-naphthyl-2-benzyloxycarbonylmethyl-propionyl, 3-phenyl- or 3-α-naphthyl-2-carbamoyl-propionyl, 3-phenyl- or 3-α-naphthyl-2-tert.-butylcarbamoyl-propionyl, 3-phenyl- or 3-α-naphthyl-2-(2-dimethylaminoethyl)-carbamoyl-propionyl, 3-α-naphthyl-2-(carboxy- or tert.-butoxycarbonyl)-methylcarbamoyl-propionyl, 3-phenyl- or 3-α-naphthyl-2-(3-hydroxy-2-propyl)-carbamoyl-propionyl, 3-phenyl- or 3-α-naphthyl-2-(2,2-dimethoxyethyl)-carbamoylpropionyl, 3-phenyl- or 3-α-naphthyl-2-(5-amino-5-carboxypentyl)-carbamoyl-propionyl, 3-phenyl- or 3-α-naphthyl-2-cyano-propionyl, 3-phenyl- or 3-α-naphthyl-2-cyanomethyl-propionyl, 3-phenyl-2-phosphono- or -phosphonomethyl-propionyl, 3-phenyl-2-dimethoxyphosphoryl- or -dimethoxyphosphorylmethyl-propionyl, 3-phenyl-2-diethoxyphosphoryl- or -diethoxyphosphorylmethyl-propionyl, 3-phenyl-2-ethoxy- or -methoxyhydroxyphosphoryl-propionyl, 3-phenyl- or 3-α-naphthyl-2-acetonyl-propionyl, 3-phenyl- or 3-α-naphthyl-2-dimethylaminomethyl-propionyl, 2-benzyl- or 2-α-naphthylmethyl-4-cyano-butyryl, 4-phenyl- or 4-α-naphthyl-3-carboxy-butyryl, 4-phenyl- or 4-α-naphthyl-3-benzyloxycarbonyl-butyryl, 2-benzyl-4-(2-benzofuranyl)-4-oxo-butyryl, 2-benzyl- or 2-α-naphthylmethyl-4-oxo-pentanoyl, 2-benzyl- or 2-α-naphthylmethyl-4,4-dimethyl-3-oxo-pentanoyl, 2-benzyl- or 2-α-naphthylmethyl-5-dimethylamino-pentanoyl, 2-benzyl- or 2-α-naphthylmethyl-5-dimethylamino-4-oxo-pentanoyl, 2-benzyl- or 2-α-naphthylmethyl-5,5-dimethyl-4-oxo-hexanoyl, α,p-diamino-phenylacetyl, α,p-diacylaminophenylacetyl, such as α,p-dibenzyloxycarbonylaminophenylacetyl or α-pivaloylamino-p-benzyloxycarbonylamino-phenylacetyl, phenyl-lower alkenoyl, for example β-phenylacryloyl or β-phenylvinylacetyl, naphthylcarbonyl, for example α- or β-naphthylcarbonyl or 1,8-naphthalenedicarbonyl, indenylcarbonyl, for example 1-, 2- or 3-indenylcarbonyl, indanylcarbonyl, for example 1- or 2-indanylcarbonyl, phenanthrenylcarbonyl, for example 9-phenanthrenylcarbonyl, optionally substituted pyrrolylcarbonyl, for example 2- or 3-pyrrolylcarbonyl or 4- or 5-phenylpyrrolyl-2-carbonyl, furylcarbonyl, for example 2-furylcarbonyl, thienylcarbonyl, for example 2-thienylcarbonyl, pyridylcarbonyl, for example 2-, 3- or 4-pyridylcarbonyl, optionally substituted indolylcarbonyl, for example 2-, 3- or 5-indolylcarbonyl, 1-methyl-, 5-methyl-, 5-methoxy-, 5-benzyloxy-, 5-chloro- or 4,5-dimethylindolyl-2-carbonyl, 1-benzylindolyl-2- or -3-carbonyl, 4,5,6,7-tetrahydroindolyl-2-carbonyl, cyclohepta[b]pyrrolyl-5-carbonyl, optionally substituted quinolylcarbonyl, for example 2-, 3- or 4-quinolylcarbonyl or 4-hydroxyquinolyl-2-carbonyl, optionally substituted isoquinolylcarbonyl, for example 1-, 3- or 4-isoquinolylcarbonyl or 1-oxo-1,2-dihydroisoquinolyl-3-carbonyl, 2-quinoxalinylcarbonyl, 2-benzofuranylcarbonyl, benz[e]indolyl-2-carbonyl, β-carbolinyl-3-carbonyl, pyrrolidinyl-3-carbonyl, hydroxypyrrolidinylcarbonyl, for example 3- or 4-hydroxypyrrolidinyl-2-carbonyl, oxopyrrolidinylcarbonyl, for example 5-oxo-pyrrolidinyl-2-carbonyl, piperidinylcarbonyl, for example 2-, 3- or 4-piperidinylcarbonyl, indolinylcarbonyl, for example 2- or 3-indolinylcarbonyl, 1,2,3,4-tetrahydroquinolylcarbonyl, for example 1,2,3,4-tetrahydroquinolyl-2-, -3- or -4-carbonyl, 1,2,3,4-tetrahydroisoquinolylcarbonyl, for example 1,2,3,4-tetrahydroisoquinolyl-1-, -3- or -4-carbonyl or 1-oxo-1,2,3,4-tetrahydroisoquinolyl-3-carbonyl, lower alkoxycarbonyl, for example methoxy-, ethoxy- or tert.-lower alkoxy-carbonyl, such as tert.-butoxycarbonyl, 2-halo-lower alkoxycarbonyl, for example 2-chloro-, 2-bromo-, 2-iodo- or 2,2,2-trichloroethoxycarbonyl, aryl-lower alkoxycarbonyl, for example arylmethoxycarbonyl, in which aryl is phenyl, 1- or 2-naphthyl, or phenyl mono- or poly-substituted by lower alkyl, for example methyl or tert.-butyl, lower alkoxy, for example methoxy, ethoxy or tert.-butoxy, hydroxy, halogen, for example chlorine or bromine, and/or by nitro, for example benzyloxycarbonyl, 4-methoxybenzyloxycarbonyl, 4-nitrobenzyloxycarbonyl, diphenylmethoxycarbonyl, di-(4-methoxyphenyl)-methoxycarbonyl or trityloxycarbonyl, and also oxamoyl or lower alkyloxamoyl, for example methyl- or ethyl-oxamoyl.

A is a bivalent residue of an α-amino acid, for example of a natural α-amino acid having the L-configuration, as is normal in proteins, of a homologue of such an amino acid, for example in which the amino acid side chain is lengthened or shortened by one or two methylene groups and/or a methyl group has been replaced by hydrogen, of a substituted aromatic α-amino acid, for example a mono- or poly-substituted phenylalanine or phenylglycine in which the substituent(s) may be lower alkyl, for example methyl, halogen, for example fluorine, chlorine, bromine or iodine, hydroxy, lower alkoxy, for example methoxy, lower alkanoyloxy, for example acetoxy, amino, lower alkylamino, for example methylamino, di-lower alkylamino, for example dimethylamino, lower alkanoylamino, for example acetylamino or pivaloylamino, lower alkoxycarbonylamino, for example tert.-butoxycarbonylamino, arylmethoxycarbonylamino, for example benzyloxycarbonylamino, and/or nitro, of a benzo-annellated phenylalanine or phenylglycine, such as α-naphthylalanine, or of a hydrogenated phenylalanine or phenylglycine, such as cyclohexylalanine or cyclohexylglycine, of a five- or six-membered cyclic, benzo-annellated α-amino acid, for example indoline-2-carboxylic acid or 1,2,3,4-tetrahydroisoquinoline-3-carboxylic acid, of a natural or homologous α-amino acid in which a carboxy group of the side chain is in esterified or amidated form, for example in the form of a lower alkyl ester group, such as methoxycarbonyl or tert.-butoxycarbonyl, or in the form of a carbamoyl group, a lower alkylcarbamoyl group, such as methylcarbamoyl, or a di-lower alkylcarbamoyl group, such as dimethylcarbamoyl, in which an amino group of the side chain is in acylated form, for example in the form of a lower alkanoylamino group, such as acetylamino or pivaloylamino, in the form of a lower alkoxycarbonylamino group, such as tert.-butoxycarbonylamino, or in the form of an arylmethoxycarbonylamino group, such as benzyloxycarbonylamino, or in which a hydroxy group of the side chain is in etherified or esterified form, for example in the form of a lower alkoxy group, such as methoxy, in the form of an aryl-lower alkoxy group, such as benzyloxy, or in the form of a lower alkanoyloxy group, such as acetoxy, or A is a bivalent residue of an epimer of such an amino acid, that is to say having the non-naturally occurring D-configuration.

Such amino acids are, for example, glycine (H—Gly—OH), alanine (H—Ala—OH), valine (H—Val—OH), norvaline (α-aminovaleric acid), leucine, (H—Leu—OH), isoleucine (H—Ile—OH), norleucine (α-aminohexanoic acid, H—Nle—OH), serine (H—Ser—OH), homoserine (α-amino-γ-hydroxybutyric acid), threonine (H—Thr—OH), methionine (H—Met—OH), cysteine (H—Cys—OH), proline (H—Pro—OH), trans-3- and trans-4-hydroxyproline, phenylalanine (H—Phe—OH), tyrosine (H—Tyr—OH), 4-nitrophenylalanine, 4-aminophenylalanine, 4-chlorophenylalanine, β-phenylserine (β-hydroxyphenylalanine), phenylglycine, α-naphthylalanine, cyclohexylalanine (H—Cha—OH), cyclohexylglycine, tryptophan (H—Trp—OH), indoline-2-carboxylic acid, 1,2,3,4-tetrahydroisoquinoline-3-carboxylic acid, aspartic acid (H—Asp—OH), asparagine (H—Asn—OH), aminomalonic acid, aminomalonic acid monoamide, glutamic acid (H—Glu—OH), glutamic acid mono-tert.-butyl ester, glutamine (H—Gln—OH), $N^\delta$-dimethylglutamine, histidine (H—His—OH), arginine (H—Arg—OH), lysine (H—Lys—OH), $N^\epsilon$-tert.-butoxycarbonyl-lysine, δ-hydroxylysine, ornithine (α,δ-diaminovaleric acid), $N^\delta$-pivaloyl-ornithine, α,γ-diaminobutyric acid or α,β-diaminopropionic acid.

In order to increase the stability of the compound of the formula I towards enzymatic degradation, the amino acid residue A can be substituted N-terminally by lower alkyl, for example methyl or ethyl.

A is preferably the bivalent residue of alanine, valine, norvaline, leucine, norleucine, serine, etherified serine, proline, phenylalanine, β-phenylserine, α-naphthylalanine, cyclohexylalanine, indoline-2-carboxylic acid, 1,2,3,4-tetrahydroisoquinoline-3-carboxylic acid, aspartic acid, esterified aspartic acid, asparagine, aminomalonic acid, aminomalonic acid monoamide, glutamic acid, esterified glutamic acid, glutamine, di-lower alkylglutamine, histidine, lysine, acylated lycine, ornithine or acylated ornithine, if desired substituted N-terminally by lower alkyl, for example methyl. Very especially preferred as the group A is the bivalent residue of histidine.

Lower alkyl $R_2$ or $R_3$ has the meanings mentioned hereinbefore for lower alkyl $R^a$ or $R^b$. Lower alkyl $R_2$ is preferably methyl or ethyl. Lower alkyl $R_3$ is preferably isopropyl, isobutyl or tert.-butyl.

Hydroxy-lower alkyl $R_3$ or $R_5$ is preferably hydroxymethyl or hydroxyethyl and is optionally etherified or esterified by one of the groups indicated hereinafter for etherified or esterified hydroxy $R_4$.

Cycloalkyl $R_3$ or $R_5$ has the meanings mentioned hereinbefore for cycloalkyl $R^a$ or $R^b$ and is preferably cyclopentyl or cyclohexyl.

Cycloalkyl-lower alkyl $R_3$ or $R_5$ has the meanings mentioned hereinbefore for cycloalkyl-lower alkyl $R^a$ or $R^b$ and is preferably cyclohexylmethyl.

Bicycloalkyl-lower alkyl $R_3$ or $R_5$ contains, for example, from 6 to 14, especially from 7 to 12, carbon atoms and is, for example, methyl or ethyl substituted by the radicals mentioned hereinbefore for bicycloalkyl $R^a$ or $R^b$, for example bicyclo[2.2.1]-hept-2-ylmethyl.

Tricycloalkyl-lower alkyl $R_3$ or $R_5$ contains, for example from 9 to 14, especially from 10 to 12, carbon atoms and is, for example, methyl or ethyl substituted by the radicals mentioned hereinbefore for tricycloalkyl $R^a$ or $R^b$, preferably 1-adamantylmethyl.

Aryl $R_3$ or $R_5$ has the meanings mentioned hereinbefore for aromatic hydrocarbon radicals $R^a$ or $R^b$ and is preferably phenyl.

Aryl-lower alkyl $R_3$ or $R_5$ has the meanings mentioned hereinbefore for aryl-lower alkyl $R_a$ or $R_b$ and is preferably benzyl.

An etherified hydroxy group $R_4$ is preferably etherified by organic radicals that can be resolved under physiological conditions and that, after removal, produce cleavage products that are pharmacologically harmless in the concentration concerned.

Etherified hydroxy $R_4$ is, for example, acyloxy-lower alkoxy in which acyl is the acyl group of an optionally branched lower alkanecarboxylic acid or of carbonic acid mono-esterified by optionally branched lower alkyl, for example lower alkanoyloxy-lower alkoxy, such as acetoxymethoxy, 1-acetoxyethoxy, pivaloyloxymethoxy or 1-pivaloyloxyethoxy, or lower alkoxycarbonyloxy-lower alkoxy, such as ethoxycarbonyloxymethoxy, 1-ethoxycarbonyloxyethoxy, tert.-butoxycarbonyloxymethoxy oe 1-tert.-butoxycarbonyloxyethoxy.

Etherified hydroxy $R_4$ is also lower alkoxy, for example methoxy or ethoxy, aryloxy, for example phenoxy, or aryl-lower alkoxy, for example benzyloxy.

Esterified hydroxy $R_4$ is, for example, aliphatic acyloxy, for example lower alkanoyloxy, such as acetoxy or pivaloyloxy, cycloaliphatic acyloxy, for example cycloalkylcarbonyloxy, such as cyclohexylcarbonyloxy, or aromatic acyloxy, for example benzoyloxy.

Lower alkyl $R_5$ has 2 or more, preferably from 2 to 7, carbon atoms and is, for example, ethyl, n-propyl, isopropyl, n-butyl, isobutyl, tert.-butyl or isopentyl. Isopropyl, isobutyl and tert.-butyl are especially preferred.

Bicycloalkyl $R_5$ has the meanings mentioned hereinbefore for bicycloalkyl $R^a$ or $R^b$ and is preferably α-decahydronaphthyl.

Tricycloalkyl $R_5$ has the meanings mentioned hereinbefore for tricycloalkyl $R^a$ or $R^b$ and is preferably 1-adamantyl.

Optionally substituted carbamoyl $R_5$ is unsubstituted or substituted by one or two lower alkyl or hydroxy-lower alkyl groups and is, for example, carbamoyl, methylcarbamoyl, ethylcarbamoyl, n-propylcarbamoyl, isopropylcarbamoyl, n-butylcarbamoyl, dimethylcarbamoyl, 2-hydroxyethylcarbamoyl or di-(2-hydroxyethyl)-carbamoyl.

Optionally substituted amino $R_5$ is unsubstituted or substituted by one or two lower alkyl groups or by aryl-lower alkyl, lower alkanoyl, lower alkoxycarbonyl or arylmethoxycarbonyl and is, for example, amino, methylamino, ethylamino, n-butylamino, dimethylamino, benzylamino, acetylamino, pivaloylamino, methoxy-, ethoxy- or tert.-butoxy-carbonylamino or benzyloxycarbonylamino, preferably dimethylamino.

Optionally substituted hydroxy $R_5$ is unsubstituted or etherified or esterified by one of the groups mentioned hereinbefore for etherified or esterified hydroxy $R_4$ and is, for example, hydroxy, methoxy, ethoxy, acetoxymethoxy, phenoxy, benzyloxy, acetoxy, pivaloyloxy or benzoyloxy.

Optionally substituted mercapto $R_5$ is unsubstituted or substituted by lower alkyl, for example methyl or ethyl, aryl, for example phenyl, aryl-lower alkyl, for example benzyl, lower alkanoyl, for example acetyl, or arylcarbonyl, for example benzoyl, and is, for example, mercapto, methylthio, ethylthio, phenylthio, benzylthio, acetylthio or benzoylthio.

Substituted amino $R_6$ is, for example, an amino group that is substituted by one or optionally two unsubstituted or substituted, saturated or unsaturated, aliphatic hydrocarbon radicals having up to and including 18, preferably up to and including 10, carbon atoms or by an unsubstituted or substituted, aromatic, heteroaromatic, aromatic-aliphatic or heteroaromaticaliphatic hydrocarbon radical having up to 18, preferably up to and including 10, carbon atoms.

Excluded as substituted amino $R_6$ is the residue of an α-amino acid or its N-substituted, esterified or amidated derivatives.

An unsubstituted or substituted, saturated or unsaturated, aliphatic hydrocarbon radical that substitutes the amino group $R_6$ is, for example, optionally substituted alkyl having up to 10 carbon atoms, lower alkenyl or lower alkynyl having up to and including 7 carbon atoms, or cycloalkyl-lower alkyl having from 4 to 10 carbon atoms.

These radicals can be substituted, like lower alkyl $R^a$ or $R^b$, by one or more of the functional groups mentioned hereinbefore, and by sulpho, amino, lower alkylamino, for example methylamino, ethylamino or n-butylamino, di-lower alkylamino, for example dimethylamino, lower alkanoylamino, for example acetylamino or pivaloylamino, lower alkoxycarbonylamino, for example tert.-butoxycarbonylamino, arylmethoxycarbonylamino, for example benzyloxycarbonylamino, guanidino or by substituted amino in which the amino group is part of a five- or six-membered heterocycle containing one or two nitrogen atoms and, if desired, an oxygen or sulphur atom, for example 1-pyrrolidinyl, 1-piperidinyl, 1-pyridazinyl, 4-morpholinyl or 4-thiomorpholinyl.

Preferred substituents are hydroxy, lower alkoxy, for example methoxy, lower alkanoyloxy, for example acetoxy, substituted or unsubstituted phenoxy, for example carbamoylphenoxy or carbamoyl-hydroxyphenoxy, carboxy, esterified carboxy, for example lower alkoxycarbonyl, such as methoxycarbonyl, or tert.-butoxycarbonyl, or a physiologically cleavable esterified carboxy, for example 1-(lower alkanoyloxy)-lower alkoxycarbonyl, such as acetoxymethoxycarbonyl, pivaloyloxymethoxycarbonyl or 1-propionyloxyethoxycarbonyl, 1-(lower alkoxycarbonyloxy)-lower alkoxycarbonyl, such as 1-(ethoxycarbonyloxy)-ethoxycarbonyl, or α-amino-lower alkanoyloxymethoxycarbonyl, such as α-aminoacetoxymethoxycarbonyl or (S)-α-amino-β-methylbutyryloxymethoxycarbonyl, carbamoyl, substituted or unsubstituted lower alkylcarbamoyl, for example hydroxy-lower alkylcarbamoyl, such as 2-hydroxyethylcarbamoyl or tris-(hydroxymethyl)-methylcarbamoyl, amino, lower alkylamino, for example methylamino, di-lower alkylamino, for example dimethylamino, lower alkoxycarbonylamino, for example tert.-butoxycarbonylamino, guanidino, or a saturated five- or six-membered heterocyclyl that is bonded via a nitrogen atom and, if desired, substituted by oxo, for example 1-piperidyl, 4-morpholinyl or 2-oxo-1-pyrrolidinyl.

An aromatic or aromatic-aliphatic hydrocarbon radical in a group $R_6$ has the same meanings as those mentioned under $R^a$ or $R^b$ and is preferably phenyl or phenyl-lower alkyl.

These radicals may be substituted in the aromatic moiety, for example by lower alkyl, for example methyl or ethyl, hydroxy, etherified hydroxy, for example lower alkoxy, such as methoxy or tert.-butoxy, esterified hydroxy, for example lower alkanoyloxy, such as acetoxy, or halogen, for example fluorine or chlorine, carboxy, esterified carboxy, for example lower alkoxycarbonyl, such as tert.-butoxycarbonyl, carbamoyl, amino, lower alkylamino, for example methylamino, di-lower alkylamino, for example dimethylamino, acylated amino, for example lower alkoxycarbonylamino, such as tert.-butoxycarbonylamino, or also by nitro.

Lower alkyl in a phenyl-lower alkyl radical may be substituted by the same substituents as may alkyl in a radical $R_6$.

A heteroaromatic or heteroaromatic-aliphatic hydrocarbon radical in a group $R_6$ has the same meaning as those mentioned under $R^a$ and $R^b$ and is preferably pyridyl-lower alkyl, for example 2-, 3- or 4-pyridylmethyl, imidazolyl-lower alkyl, for example 2-(4-imidazolyl)-ethyl or also 2-(2-[4-imidazolyl]-ethylamino)-ethyl, or indolyl-lower alkyl, for example 3-indolylmethyl or 2-(3-indolyl)-ethyl.

Substituted amino $R_6$ is preferably alkylamino, for example methyl-, ethyl-, n-propyl-, isopropyl-, n-butyl-, isobutyl-, tert.-butyl-, n-pentyl-, isopentyl-, n-hexyl-, n-octyl- or n-decyl-amino, di-lower alkylamino, for example dimethylamino or diethylamino, hydroxy-lower alkylamino, for example 2-hydroxyethylamino, 1-hydroxybut-2-ylamino, 5-hydroxypentylamino or tris(hydroxymethyl)-methylamino, di-(hydroxy-lower alkyl)-amino, for example di-(2-hydroxyethyl)-amino, lower alkoxy-lower alkylamino, for example 2-methoxyethylamino, lower alkanoyloxy-lower alkylamino, for example 2-acetoxyethylamino, phenoxylower alkylamino or phenoxy-hydroxy-lower alkylamino in which phenoxy is optionally substituted by lower alkyl, lower alkoxy, hydroxy, carboxy, lower alkoxycarbonyl or by carbamoyl, for example 2-phenoxyethylamino, 2-(3-carbamoyl-4-hydroxyphenoxy)-ethylamino or 3-(3-carbamoylphenoxy)-2-hydroxy-propylamino, carboxyalkylamino or amino-carboxy-alkylamino in which the carboxy radical is not in the 1-position of the alkyl radical, for example 4-carboxy-n-butylamino, 5-carboxy-npentylamino, 5-amino-5-carboxy-n-pentylamino, 6-carboxy-n-hexylamino, 7-carboxy-n-heptylamino or 8-carboxy-noctylamino, also dicarboxymethylamino, lower alkoxycarbonylalkylamino or acylamino-lower alkoxycarbonylalkylamino in which the carbonyl radical is not in the 1-position of the alkyl radical, for example 4-tert.-butoxycarbonyl-n-butylamino, 5-tert.-butoxycarbonylamino-5-methoxycarbonyl-n-pentylamino, 7-tert.-butoxycarbonyl-n-heptylamino or 8-tert.-butoxycarbonyl-n-octylamino, also di-lower alkoxycarbonyl-methylamino, for example di-methoxycarbonyl-methylamino, physiologically cleavable esterified carboxyalkylamino in which the ester function is not in the 1-position of the alkyl radical, for example 4-pivaloyloxymethoxycarbonyl-n-butylamino, 7-(1-ethoxycarbonyloxyethoxycarbonyl)-n-heptylamino or 7-pivaloyloxymethoxycarbonyl-n-heptylamino, carbamoylalkylamino or hydroxy-lower alkylcarbamoylalkylamino in which the carbamoyl radical is not in the 1-position of the alkyl radical, for example 4-carbamoyl-n-butylamino, 7-carbamoyl-n-heptylamino or 4-(tris[hydroxymethyl]-methyl)-carbamoyl-n-butylamino, also dicarbamoyl-methylamino, di-(lower alkylcarbamoyl)-methylamino, for example di-(methylcarbamoyl)-methylamino, di-(hydroxy-lower alkylcarbamoyl)-methylamino, for example di-(2-hydroxyethylcarbamoyl)-methylamino, or bis-(di-lower alkylcarbamoyl)-methylamino, for example bis-(dimethylaminocarbamoyl)-methylamino, amino-lower alkylamino, for example 2-aminoethylamino or 3-aminopropylamino, lower alkylamino-lower alkylamino, for example 2-methylaminoethylamino, di-lower alkylamino-lower alkylamino, for example 2-dimethylaminoethylamino or 3-dimethylaminopropylamino, lower alkoxycarbonylamino-lower alkylamino, for example 2-(tert.-butoxycarbonylamino)-ethylamino, guanidino-lower alkylamino, for example 2-guanidinoethylamino, saturated five- or six-membered heterocyclyl-lower alkylamino that is bonded via a nitrogen atom, for example 2-(4-morpholinyl)ethylamino, 3-(4-morpholinyl)-propylamino or 3-(2-oxo-1-pyrrolidinyl)-propylamino, lower alkenylamino, for example allylamino or 2- or 3-butenylamino, lower alkynylamino, for example propargylamino, cycloalkyl-lower alkylamino, for example cyclopropylmethylamino or cyclohexylmethylamino, phenylamino or phenyl-lower alkylamino in which phenyl is optionally mono- or poly-substituted by lower alkyl, for example methyl, hydroxy, lower alkoxy, for example methoxy or tert.butoxy, lower alkanoyloxy, for example ethoxy, halogen, for example fluorine or chlorine, carboxy, lower alkoxycarbonyl, for example tert.-butoxycarbonyl, carbamoyl, amino, lower alkylamino, for example methylamino, di-lower alkylamino, for example dimethylamino, acylamino, for example tert.butoxycarbonylamino and/or by nitro, for example phenylamino, 2-, 3- or 4-methylphenylamino, 4-hydroxyphenylamino, 4-methoxyphenylamino, 2,3-, 2,4- or 2,5dimethoxyphenylamino, 4-chlorophenylamino, 2-, 3- or 4-carboxyphenylamino, 2-, 3- or 4-methoxy- or tert.-butoxy-carbonylphenylamino, 2-, 3- or 4-carbamoylphenylamino, 4-aminophenylamino, 4-tert.-butoxycarbonylaminophenylamino or 4-nitrophenylamino, also, for example, benzylamino, 4-methylbenzylamino, 4-methoxybenzylamino, 2-, 3- or 4-carboxybenzylamino, 2-, 3- or 4-tert.-butoxycarbonylamino, 2-, 3- or 4-carbamoylbenzylamino, 2-phenylethylamino or 3-phenylpropylamino, pyridyl-lower alkylamino, for example 2-, 3- or 4-pyridylmethylamino, 2-(2-, 3- or 4-pyridyl)-ethylamino or 3-(2-, 3- or 4-pyridyl)-propylamino, imidazolyl-lower alkylamino, for example 4-imidazolylmethylamino, 2-(4-imidazolyl)-ethylamino or 2-(2-[4-imidazolyl]-ethylamino)-ethylamino, or indolyl-lower alkylamino, for example 3-indolylmethylamino or 2-(3-indolyl)-ethylamino.

Salts are especially the pharmaceutically acceptable non-toxic salts of compounds of the formula I.

Such salts are formed, for example, by compounds of the formula I having an acidic group, for example a carboxy group, and are, especially, suitable alkali metal salts, for example sodium or potassium salts, or suitable alkaline earth metal salts, for example magnesium or calcium salts, and also zinc salts or ammonium salts, and also those salts which are formed with organic amines, such as optionally hydroxy-substituted mono-, di- or tri-alkylamines, for example diethylamine, di-(2-hydroxyethyl)-amine, triethylamine, N,N-dimethyl-N-(2-hydroxyethyl)-amine, tri-(2-hydroxyethyl)-amine or N-methyl-D-glucamine. The compounds of the formula I having a basic group, for example an amino group, can form acid addition salts, for example with inorganic acids, for example hydrochloric acid, sulphuric acid or phosphoric acid, or with organic carboxylic, sulphonic or sulpho acids, for example acetic acid, propionic acid, glycolic acid, succinic acid, maleic acid, hydroxymaleic acid, methylmaleic acid, fumaric acid, malic acid, tartaric acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and amino acids, such as, for example, the α-amino acids mentioned hereinbefore, and also methanesulphonic acid, ethanesulphonic acid, 2-hydroxyethanesulphonic acid, ethane-1,2-disulphonic acid, benzenesulphonic acid, 4-methylbenzenesulphonic acid or naphthalene-2sulphonic acid, or with other acidic organic compounds, such as ascorbic acid. Compounds of the formula I having acidic and basic groups can also form internal salts.

For the purposes of isolation or purification it is also possible to use pharmaceutically unsuitable salts.

The compounds of the present invention exhibit enzyme-inhibiting actions; in particular, they inhibit the action of the natural enzyme renin. The latter passes from the kidneys into the blood and there brings about the cleavage of angiotensinogen to form the decapeptide angiotensin I which is then cleaved in the lungs, the kidneys and other organs to form the octapeptide angiotensin II. The latter raises the blood pressure both directly through arterial constriction and indirectly through releasing from the adrenal glands the hormone aldosterone which retains sodium ions, which involves an increase in the extracellular fluid volume. This increase is to be attributed to the action of angiotensin II itself or of the heptapeptide angiotensin III formed therefrom as a cleavage product. Inhibitors of the enzymatic activity of renin bring about a reduction in the formation of angiotensin I. As a consequence of this, less angiotensin II is produced. The reduced concentration of this active peptide hormone is the direct cause of the blood pressure-reducing action of renin-inhibitors.

The action of renin-inhibitors is demonstrated experimentally inter alia by means of in vitro tests, the reduction in the formation of angiotensin I being measured in various systems (human plasma, purified human renin together with synthetic or natural renin substrate). The following in vitro test inter alia is used: An extract of human renin from the kidney (0.5 mGU [milli Goldblatt units]/ml) is incubated for one hour at 37° C. and pH 7.2 in 1 molar aqueous 2-N-(tris-hydroxymethyl-methyl)-amino-ethanesulphonic acid buffer solution with 23 ug/ml of synthetic renin substrate, the tetradecapeptide H-Asp-Arg-Val-Tyr-Ile-His-Pro-Phe-His-Leu-Leu-Val-Tyr-Ser-OH. The amount of angiotensin I formed is determined by a radioimmunoassay. The inhibiting substances according to the invention are each added to the incubation mixture in different concentrations. $IC_{50}$ denotes that concentration of the particular inhibiting substance which reduces the formation of angiotensin I by 50%. In the in vitro systems, the compounds of the present invention exhibit inhibiting actions at minimum concentrations of from approximately $10^{-6}$ to approximately $10^{-9}$ mol/liter.

In animals depleted of salt the renin-inhibitors bring about a fall in blood pressure. Human renin differs from renin of other species. For testing inhibitors of human renin primates (marmosets, *Callithrix jacchus*) are used since human renin and primate renin are to a great extent homologous in the enzymatically active range. The following in vivo test inter alia is used: The test compounds are tested in conscious normotensive marmosets of both sexes having a body weight of approximately 300 g. Blood pressure and heart rate are measured by means of a catheter in the femoral artery. The endogenous release of renin is stimulated by intravenous injection of furosemide (5 mg/kg). 30 minutes after the injection of furosemide, the test substances are administered via a catheter in the lateral caudal vein either by a single injection or by continuous infusion and their effect on the blood pressure and heart rate is evaluated. The compounds of the present invention are effective in the described in vivo test in doses of from approximately 0.1 to approximately 1.0 mg/kg i.v.

The compounds of the present invention can be used for the treatment of renin-associated hyperaldosteronism, hypertension and cardiac insufficiency.

The invention relates especially to compounds of the formula I in which $R_1$ represents hydrogen or acyl having the partial formula $R^b$—CO—, $R^a$—O—CO— or $(R^b)(R^b)N$—CO—CO—, in which $R_a$ represents an unsubstituted or substituted, saturated or unsaturated aliphatic, cycloaliphatic or cycloaliphatic-aliphatic hydrocarbon radical having up to and including 18, preferably up to and including 10, carbon atoms, or an unsubstituted or substituted aromatic, heteroaromatic, aromatic-aliphatic or heteroaromatic-aliphatic hydrocarbon radical having up to and including 18, preferably up to and including 10, carbon atoms, or an unsubstituted or substituted, saturated five- or six-membered heterocycle, and $R^b$ represents hydrogen or has the meanings of $R^a$, with the exception of an optionally N-substituted acyl residue of a natural amino acid, A represents an optionally N-alkylated α-amino acid residue that is bonded N-terminally to $R_1$ and C-terminally to the group —$NR_2$—, $R_2$ represents hydrogen or lower alkyl, $R_3$ represents hydrogen, lower alkyl, hydroxy-lower alkyl, cycloalkyl, cycloalkyl-lower alkyl, bicycloalkyl-lower alkyl, tricycloalkyl-lower alkyl, aryl or aryl-lower alkyl, $R_4$ represents hydroxy, $R_5$ represents lower alkyl having 2 or more carbon atoms, hydroxy-lower alkyl, cycloalkyl, cycloalkyl-lower alkyl, bicycloalkyl, bicycloalkyl-lower alkyl, tricycloalkyl, tricycloalkyl-lower alkyl, carbamoyl, lower alkylcarbamoyl, di-lower alkylamino, aryl or aryl-lower alkyl, and $R_6$ represents an amino group that is substituted by one or optionally two unsubstituted or substituted, saturated or unsaturated aliphatic hydrocarbon radical(s) having up to and including 18, preferably up to and including 10, carbon atoms, or by an unsubstituted or substituted aromatic, heteroaromatic, aromatic-aliphatic or heteroaromatic-aliphatic hydrocarbon radical having up to and including 18, preferably up to and including 10, carbon atoms, with the exception of an amino residue derived from an α-amino acid, and to pharmaceutically acceptable salts of such compounds having salt-forming groups.

The invention relates chiefly to compounds of the formula I in which $R_1$ represents hydrogen, lower alkanoyl having from 1 to 7 carbon atoms, for example formyl, acetyl, propionyl or pivaloyl, hydroxy-lower alkanoyl, for example β-hydroxypropionyl, lower alkoxy-lower alkanoyl, for example lower alkoxyacetyl or lower alkoxypropionyl, such as methoxyacetyl or β-methoxypropionyl, phenoxy-lower alkanoyl, for example phenoxyacetyl, naphthoxy-lower alkanoyl, for example α- or β-naphthoxyacetyl, lower alkanoyloxy-lower alkanoyl, for example lower alkanoyloxyacetyl or lower alkanoyloxypropionyl, such as acetoxyacetyl or β-acetoxypropionyl, carboxy-lower alkanoyl, for example carboxyacetyl or β-carboxypropionyl, lower alkoxycarbonyl-lower alkanoyl, for example lower alkoxycarbonylacetyl or lower alkoxycarbonylpropionyl, such as methoxycarbonylacetyl, β-methoxycarbonylpropionyl, ethoxycarbonylacetyl or β-ethoxycarbonylpropionyl, carbamoyl-lower alkanoyl, for example carbamoylacetyl or β-carbamoylpropionyl, lower alkylcarbamoyl-lower alkanoyl, for example methylcarbamoyl-lower alkanoyl, di-lower alkylcarbamoyl-lower alkanoyl, for example dimethylcarbamoylacetyl, α-naphthoxycarboxy-lower alkanoyl, for example 2-α-naphthoxy-4-carboxy-butyryl, α-naphthoxy-lower alkoxycarbonyl-lower alkanoyl, for example α-naphthoxy-ethoxycarbonyl-acetyl, 2-α-naphthoxy-3-ethoxycarbonyl-propionyl or 2-α-naphthoxy-4-tert.-butoxycarbonyl-butyryl, α-naphthoxy-benzyloxycarbonyl-lower alkanoyl, for example 2-α-naphthoxy-3-benzyloxycarbonyl-propionyl, α-naphthoxy-carbamoyl-lower alkanoyl, for example 2-α-naphthoxy-4-carbamoylbutyryl, α-naphthoxy-cyano-lower alkanoyl, for example α-naphthoxy-cyano-acetyl or 2-α-naphthoxy-4-cyanobutyryl, α-naphthoxy-di-lower alkylamino-lower alkanoyl, for example 2-α-naphthoxy-5-dimethylaminopentanoyl, α-naphthoxy-oxo-lower alkanoyl, for example 2-α-naphthoxy-4-oxopentanoyl, lower alkenoyl having from 3 to 7 carbon atoms, for example acryloyl, vinylacetyl, crotonoyl or 3- or 4-pentenoyl, lower alkynoyl having from 3 to 7 carbon atoms, for example propiolyl or 2- or 3-butynoyl, cycloalkylcarbonyl having from 4 to 9 carbon atoms, for example cyclopropylcarbonyl, cyclobutylcarbonyl, cyclopentylcarbonyl or cyclohexylcarbonyl, bicycloalkylcarbonyl having from 6 to 11 carbon atoms, for example endo- or exo-norbornyl-2-carbonyl, bicyclo[2.2.2]oct-2-ylcarbonyl or bicyclo[3.3.1]non-9ylcarbonyl, tricycloalkylcarbonyl having from 9 to 11 carbon atoms, for example 1- or 2-adamantylcarbonyl, cycloalkenylcarbonyl having from 4 to 9 carbon atoms, for example 1-cyclohexenylcarbonyl or 1,4-cyclohexadienylcarbonyl, bicycloalkenylcarbonyl having from 6 to 11 carbon atoms, for example 5-norbornen-2-ylcarbonyl or bicyclo[2.2.2]octen-2-ylcarbonyl, cycloalkyl-lower alkanoyl having from 5 to 11 carbon atoms, for example cyclopropylacetyl, cyclopentylacetyl or cyclohexylacetyl, cycloalkyl-lower alkenoyl having from 6 to 11 carbon atoms, for example cyclohexylacryloyl, cycloalkenyl-lower alkanoyl having from 5 to 11 carbon atoms, for example 1-cyclohexenylacetyl or 1,4-cyclohexadienylacetyl, benzoyl unsubstituted or mono- or poly-substituted by lower alkyl, for example methyl, halogen, for example chlorine, hydroxy, lower alkoxy, for example methoxy, and/or by nitro, for example 4chlorobenzoyl, 4-methoxybenzoyl or 4-nitrobenzoyl, phenyl-, α-naphthyl- or β-naphthyl-lower alkanoyl, in which phenyl may be unsubstituted or mono- or poly-substituted by lower alkyl, for example methyl, halogen, for example chlorine, hydroxy, lower alkoxy, for example methoxy, and/or by nitro and lower alkanoyl may be unsubstituted or substituted, for example, by hydroxy, lower alkoxy, acyloxy, carboxy, esterified carboxy, carbamoyl, substituted carbamoyl, cyano, phosphono, esterified phosphono, benzofuranyl and/or by oxo and is optionally branched, for example phenylacetyl, α-naphthylacetyl, β-naphthylacetyl, lower alkylphenylacetyl, such as 4-methylphenylacetyl, lower alkoxyphenylacetyl, such as 4-methoxyphenylacetyl, 3-phenylpropionyl, 3- (p-hydroxyphenyl)-propionyl, diphenylacetyl, di-(4-methoxyphenyl)-acetyl, triphenylacetyl, substituted anilinophenylacetyl, such as 2-(o,o-dichloroanilino)-phenylacetyl or 2-(o,o-dichloro-N-benzylanilino)-phenylacetyl, 3-α- or β-naphthylpropionyl, 3-phenyl- or 3-α-naphthyl-2-hydroxy-propionyl, 3-phenyl- or 3-α-naphthyl-2-lower alkoxy-propionyl, such as 3-phenyl- or 3-α-naphthyl-2-neopentyloxy-propionyl, 3-phenyl- or 3-α-naphthyl-2-acyloxy-propionyl, such as 3-phenyl-2-pivaloyloxy- or -2-acetoxy-propionyl, 3-α-naphthyl-2-pivaloyloxy- or -2-acetoxy-propionyl, 3-α-naphthyl-2-acetoacetoxypropionyl, 3-α-naphthyl-2-ethylaminocarbonyloxypropionyl or 3-α-naphthyl-2-(2-amino- or 2-benzyloxycarbonylamino-2-methyl-propionyloxy)-propionyl, 3-phenyl- or 3-α-naphthyl-2-carboxymethyl-propionyl, 3-phenyl- or 3-α-naphthyl-2-lower alkoxycarbonylpropionyl, such as 3-α-naphthyl-2-ethoxycarbonylpropionyl, 3-phenyl- or 3-α-naphthyl-2-benzyloxycarbonylmethyl-propionyl, 3-phenyl- or 3-α-naphthyl-2-carbamoyl-propionyl, 3-phenyl- or 3-α-naphthyl-2-tert.-butylcarbamoyl-propionyl, 3-phenyl- or 3-α-naphthyl-2(2-dimethylaminoethyl)-carbamoyl-propionyl, 3-phenyl-or 3-α-naphthyl-2-(carboxy- or tert.-butoxycarbonyl)-methylcarbamoyl-propionyl, 3-phenyl- or 3-α-naphthyl-2(3-hydroxy-2-propyl)-carbamoyl-propionyl, 3-phenyl- or 3-α-naphthyl-2-(2,2-dimethoxyethyl)-carbamoylpropionyl, 3-phenyl- or 3-α-naphthyl-2-(5-amino-5-carboxypentyl)-carbamoyl-propionyl, 3-phenyl- or 3-α-naphthyl-2-cyanopropionyl, 3-phenyl- or 3-α-naphthyl-2-cyanomethyl-propionyl, 3-phenyl-2-phosphono- or -phosphonomethyl-propionyl, 3-phenyl-2-dimethoxyphosphoryl- or -dimethoxyphosphorylmethyl-propionyl, 3-phenyl-2-diethoxyphosphoryl- or -diethoxyphosphorylmethyl-propionyl, 3-phenyl-2-ethoxy- or -methoxyhydroxyphosphoryl-propionyl, 3-phenyl- or 3-α-naphthyl-2-acetonyl-propionyl, 3-phenyl- or 3-α-naphthyl-2-dimethylaminomethyl-propionyl, 2-benzyl- or 2-α-naphthylmethyl-4-cyano-butyryl, 4-phenyl- or 4-α-naphthyl-3-carboxy-butyryl, 4-phenyl- or 4-α-naphthyl-3-benzyloxycarbonyl-butyryl, 2-benzyl-4-(2-benzofuranyl)-4-oxo-butyryl, 2-benzyl- or 2-α-naphthylmethyl-4-oxo-pentanoyl, 2-benzyl- or 2-α-naphthylmethyl-4,4-dimethyl-3-oxo-pentanoyl, 2-benzyl- or 2-α-naphthylmethyl-5-dimethylamino-pentanoyl, 2-benzyl- or 2-α-naphthylmethyl-5-dimethylamino-4-oxo-pentanoyl, 2-benzyl- or 2-α-naphthylmethyl-5,5-dimethyl-4-oxo-hexanoyl, α,p-diamino-phenylacetyl, α,p-diacylaminophenylacetyl, such as α,p-dibenzyloxycarbonylaminophenylacetyl or α-pivaloylamino-p-benzyloxycarbonylamino-phenylacetyl, phenyl-lower alkenoyl, for example β-phenylacryloyl or β-phenylvinylacetyl, napthylcarbonyl, for example α- or β-naphthylcarbonyl or 1,8-naphthalenedicarbonyl, indenylcarbonyl, for example 1-, 2- or 3-indenylcarbonyl, indanylcarbonyl, for example 1- or 2-indanylcarbonyl, phenanthrenylcarbonyl, for example 9-phenanthrenylcarbonyl, optionally substituted pyrrolylcarbonyl, for example 2- or 3-pyrrolylcarbonyl or 4- or 5-phenylpyrrolyl-2carbonyl, furylcarbonyl, for example 2-furylcarbonyl, thienylcarbonyl, for example 2-thienylcarbonyl, pyridylcarbonyl, for example 2-, 3- or 4-pyridylcarbonyl, optionally substituted indolylcarbonyl, for example 2-, 3- or 5-indolylcarbonyl, 1-methyl-, 5-methyl-, 5-methoxy-, 5-benzyloxy-, 5-chloro- or 4,5-dimethyl-indolyl-2-carbonyl, 1-benzylindolyl-2- or 3carbonyl, 4,5,6,7-tetrahydroindolyl-2-carbonyl, cyclohepta[b]pyrrolyl-5-carbonyl, optionally substituted quinolylcarbonyl, for example 2-, 3- or 4quinolylcarbonyl or 4-hydroxyquinolyl-2-carbonyl, optionally substituted isoquinolylcarbonyl, for example 1-, 3- or 4-isoquinolylcarbonyl or 1-oxo-1,2-dihydroisoquinolyl- 3-carbonyl, 2-quinoxalinylcarbonyl, 2-benzofuranylcarbonyl, benz[e]indolyl-2-carbonyl, β-carbolinyl-3-carbonyl, pyrrolidinyl-3-carbonyl, hydroxypyrrolidinylcarbonyl, for example 3- or 4-hydroxypyrrolidinyl-2-carbonyl, oxopyrrolidinylcarbonyl, for example 5-oxopyrrolidinyl-2-carbonyl, piperidinylcarbonyl, for example piperidinyl-2-, -3- or -4-carbonyl, indolinylcarbonyl, for example 2- or 3indolinylcarbonyl, 1,2,3,4-tetrahydroquinolylcarbonyl, for example 1,2,3,4-tetrahydroquinolyl-2-, -3- or -4carbonyl, 1,2,3,4-tetrahydroisoquinolylcarbonyl, for example 1,2,3,4-tetrahydroisoquinolyl-1-, -3- or -4carbonyl or 1-oxo-1,2,3,4-tetrahydroisoquinolyl-3carbonyl, aryl-lower alkoxycarbonyl, for example arylmethoxycarbonyl, in which aryl is phenyl, 1- or 2naphthyl, or phenyl mono- or poly-substituted by lower alkyl, for example methyl or tert.-butyl, lower alkoxy, for example methoxy, ethoxy or tert.-butoxy, hydroxy, halogen, for example chlorine or bromine, and/or by nitro, for example benzyloxycarbonyl, 4methoxybenzyloxycarbonyl, 4-nitrobenzyloxycarbonyl, diphenylmethoxycarbonyl, di-(4-methoxyphenyl)methoxycarbonyl or trityloxycarbonyl, and also oxamoyl or lower alkyloxamoyl, for example methyl- or ethyloxamoyl, A is a bivalent residue of an o-amino acid, for example of a natural α-amino acid having the L-configuration, as is normal in proteins, of a homologue of such an amino acid, for example in which the amino acid side chain is lengthened or shortened by one or two methylene groups and/or a methyl group has been replaced by hydrogen, of a substituted aromatic α-amino acid, for example a mono- or poly-substituted phenylalanine or phenylglycine in which the substituent(s) may be lower alkyl, for example methyl, halogen, for example fluorine, chlorine, bromine or iodine, hydroxy, lower alkoxy, for example methoxy, lower alkanoyloxy, for example acetoxy, amino, lower alkylamino, for example methylamino, di-lower alkylamino, for example dimethylamino, lower alkanoylamino, for example acetylamino or pivaloylamino, lower alkoxycarbonylamino, for example tert.-butoxycarbonylamino, arylmethoxycarbonylamino, for example benzyloxycarbonylamino, and/or nitro, of a benzo-annellated phenylalanine or phenylglycine, such as α-naphthylalanine, or of a hydrogenated phenylalanine or phenylglycine, such as cyclohexylalanine or cyclohexylglycine, of a five- or six-membered cyclic, benzoannellated α-amino acid, for example indoline-2carboxylic acid or 1,2,3,4-tetrahydroisoquinoline-3carboxylic acid, of a natural or homologous α-amino acid in which a carboxy group of the side chain is in esterified or amidated form, for example in the form of a lower alkyl ester group, such as methoxycarbonyl or tert.-butoxycarbonyl, or in the form of a carbamoyl group, a lower alkylcarbamoyl group, such as methylcarbamoyl, or a di-lower alkylcarbamoyl group, such as dimethylcarbamoyl, in which an amino group of the side chain is in acylated form, for example in the form of a lower alkanoylamino group, such as acetylamino or pivaloylamino, in the form of a lower alkoxycarbonylamino group, such as tert.-butoxycarbonylamino, or in the form of an arylmethoxycarbonylamino group, such as benzyloxycarbonylamino, or in which a hydroxy group of the side chain is in etherified or esterified form, for example in the form of a lower alkoxy group, such as methoxy, in the form of an aryl-lower alkoxy group, such as benzyloxy, or in the form of a lower alkanoyloxy group, such as acetoxy, or A is a bivalent residue of an epimer of such an amino acid, that is to say having the non-naturally occurring D-configuration, optionally substituted at the nitrogen atom by lower alkyl, for example methyl, R₂ represents hydrogen or lower alkyl, for example methyl, R₃ represents lower alkyl, for example isopropyl or isobutyl, cycloalkyl, for example cyclohexyl, cycloalkyl-lower alkyl, for example cyclohexylmethyl, tricycloalkyl-lower alkyl, for example 1-adamantylmethyl, phenyl-lower alkyl, for example benzyl, or phenyl, R₄ represents hydroxy, R₅ represents lower alkyl having 2 or more carbon atoms, for example isopropyl, isobutyl or tert.-butyl, cycloalkyl, for example cyclopentyl or cyclohexyl, cycloalkyl-lower alkyl, for example cyclohexylmethyl, bicycloalkyl, for example α-decahydronaphthyl, tricycloalkyl, for example 1-adamantyl, phenyl, phenyl-lower alkyl, for example benzyl, carbamoyl or lower alkylcarbamoyl, for example methylcarbamoyl, or di-lower alkylamino, for example dimethylamino, and R₆ represents alkylamino having from 1 to 10 carbon atoms, for example methyl-, ethyl-, n-propyl-, isopropyl-, n-butyl-, isobutyl-, tert.-butyl-, n-pentyl-, isopentyl-, n-hexyl-, n-octyl- or n-decyl-amino, di-lower alkylamino, for example dimethylamino or diethylamino, hydroxy-lower alkylamino, for example 2-hydroxyethylamino, 1-hydroxybut-2 ylamino, 5-hydroxypentylamino, or tris-(hydroxymethyl)methylamino, di-(hydroxy-lower alkyl)-amino, for example di-(2-hydroxyethyl)-amino, lower alkoxy-lower alkylamino, for example 2-methoxyethylamino, lower alkanoyloxy-lower alkylamino, for example 2-acetoxyethylamino, phenoxy-lower alkylamino or phenoxyhydroxy-lower alkylamino in which phenoxy is optionally substituted by lower alkyl, lower alkoxy, hydroxy, carboxy, lower alkoxycarbonyl or by carbamoyl, for example 2-phenoxyethylamino, 2-(3-carbamoyl-4-hydroxyphenoxy)-ethylamino or 3-(3-carbamoylphenoxy)-2-hydroxypropylamino, carboxyalkylamino or aminocarboxyalkylamino in which the carboxy radical is not in the 1-position of the alkyl radical, for example 4-carboxy-n-butyl-, 5-carboxy-n-pentyl-, 6-carboxy-n-hexyl-, 7-carboxy-n-heptyl- or 8-carboxy-n-octyl-amino or 5-amino-5-carboxy-n-pentylamino, also dicarboxymethylamino, lower alkoxycarbonylalkylamino or acylamino-lower alkoxycarbonyl-alkylamino in which the carbonyl radical is not in the 1-position of the alkyl radical, for example 4-tert.-butoxycarbonyl-n-butyl-, 7-tert.-butoxycarbonyl-n-heptyl- or 8-tert.-butoxycarbonyl-n-octyl-amino or 5-tert.-butoxycarbonylamino-5-methoxycarbonyl-n-pentylamino, also di-lower alkoxycarbonylmethylamino, for example dimethoxycarbonyl-methylamino, physiologically cleavable esterified carboxyalkylamino in which the ester function is not in the 1-position of the alkyl radical, for example 4-pivaloyloxymethoxycarbonyl-n-butylamino, 7-(1-ethoxycarbonyloxyethoxycarbonyl)-n-heptylamino or 7-pivaloyloxymethoxycarbonyl-n-heptylamino, carbamoyl- or hydroxy-lower alkylcarbamoyl-alkylamino in which the carbamoyl radical is not in the 1-position of the alkyl radical, for example 4-carbamoyl-n-butylamino, 7-carbamoyl-n-heptylamino or 4-(tris-[hydroxymethyl]-methyl)-carbamoyl-n-butylamino, also dicarbamoyl-methylamino, di-(lower alkylcarbamoyl)-methylamino, for example di-(methylcarbamoyl)-methylamino, di-(hydroxy-lower alkylcarbamoyl)-methylamino, for example di-(2-hydroxyethylcarbamoyl)-methylamino, or bis-(di-lower alkylcarbamoyl)-methylamino, for example bis-(dimethylcarbamoyl)-methylamino, amino-lower alkylamino, for example 2-aminoethylamino or 3-aminopropylamino, lower alkylamino-lower alkylamino, for example 2-methylaminoethylamino, di-lower alkylamino-lower alkylamino, for example 2-dimethylaminoethylamino or 3-dimethylaminopropylamino, lower alkoxycarbonylamino-lower alkylamino, for example 2-(tert.-butoxycarbonylamino)-ethylamino, guanidino-lower alkylamino, for example 2-guanidino-ethylamino, saturated five- or six-membered heterocyclyl-lower alkylamino that is bonded via a nitrogen atom, for example 2-(4-morpholinyl)-ethylamino, 3-(4-morpholinyl)-propylamino or 3-(2-oxopyrrolidin-1-yl)-propylamino, lower alkenylamino, for example allylamino or 2- or 3butenylamino, lower alkynylamino, for example propargylamino, cycloalkyl-lower alkylamino, for example cyclopropylmethylamino or cyclohexylmethylamino, phenylamino or phenyl-lower alkylamino in which phenyl is optionally mono- or poly-substituted by lower alkyl, for example methyl, hydroxy, lower alkoxy, for example methoxy or tert.-butoxy, lower alkanoyloxy, for example acetoxy, halogen, for example fluorine or chlorine, carboxy, lower alkoxycarbonyl, for example tert.-butoxycarbonyl, carbamoyl, amino, lower alkylamino, for example methylamino, di-lower alkylamino, for example dimethylamino, acylamino, for example tert.-butoxycarbonylamino and/or by nitro, for example phenyl-, 2-, 3- or 4-methylphenyl-, 4-hydroxyphenyl-, 4-methoxyphenyl-, 2,3-, 2,4- or 2,5-dimethoxyphenyl-, 4-chlorophenyl-, 2-, 3- or 4-carboxyphenyl-, 2-, 3- or 4-methoxy- or -tert.-butoxycarbonylphenyl-, 2-, 3- or 4-carbamoylphenyl-, 4-aminophenyl-, 4-tert.-butoxycarbonylaminophenyl- or 4-nitrophenyl-amino, also, for example, benzylamino, 4methylbenzylamino, 4-methoxybenzylamino, 2-, 3- or 4-carboxybenzylamino, 2-, 3- or 4-tert.-butoxycarbonylbenzylamino, 2-, 3- or 4-carbamoylbenzylamino, 2-phenylethylamino, or 3-phenylpropylamino, pyridyl-lower alkylamino, for example 2-, 3- or 4-pyridylmethyl-, 2(2-, 3- or 4-pyridyl)-ethyl- or 3-(2-, 3- or 4-pyridyl)-propyl-amino, imidazolyl-lower alkylamino, for example 4-imidazolylmethylamino, 2-(4-imidazolyl)-ethylamino or 2-(2-[4-imidazolyl]-ethylamino)-ethylamino, or indolyl-lower alkylamino, for example 3-indolylmethylamino or 2(3-indolyl)-ethylamino, and to pharmaceutically acceptable salts of these compounds having salt-forming groups.

The invention relates more especially to compounds of the formula I in which $R_1$ represents lower alkanoyl, for example formyl, acetyl, propionyl or pivaloyl, lower alkenoyl, for example acryloyl or crotonoyl, lower alkynoyl, for example propiolyl, cycloalkylcarbonyl, for example cyclopentyl- or cyclohexyl-carbonyl, benzoyl unsubstituted or mono- or poly-substituted by lower alkyl, for example methyl, halogen, for example chlorine, hydroxy, lower alkoxy, for example methoxy, and/or by nitro, for example 4-chlorobenzoyl, 4-methoxybenzoyl or 4-nitrobenzoyl, phenyl-lower alkanoyl in which phenyl may be unsubstituted or mono- or poly-substituted by lower alkyl, for example methyl, halogen, for example chlorine, hydroxy, lower alkoxy, for example methoxy, and/or by nitro and lower alkanoyl may be unsubstituted or substituted, for example by hydroxy, acyloxy, carboxy or esterified carboxy, for example phenylacetyl, lower alkylphenylacetyl, for example 4methylphenylacetyl, lower alkoxyphenylacetyl, for example 4-methoxyphenylacetyl, 3-phenylpropionyl, 5-phenyl-2-(phenylmethyl)-pentanoyl, 3-(p-hydroxyphenyl)-propionyl, 2-hydroxy-3-phenyl-propionyl, 2-acyloxy-3-phenyl-propionyl, for example 2-acetoxy-3-phenyl-propionyl, or 2-pivaloyloxy-3-phenyl-propionyl, diphenylacetyl, di-(4-methoxyphenyl)acetyl, triphenylacetyl, also substituted anilino-phenylacetyl, for example 2-(o,o-dichloroanilino)-phenylacetyl or 2-(o,o-dichloro-N-benzylanilino)-phenylacetyl, phenyl-lower alkenoyl, for example β-phenylacryloyl or β-phenylvinylacetyl, naphthylcarbonyl, for example 1- or 2-naphthylcarbonyl, naphthyl-lower alkanoyl in which lower alkanoyl may be substituted, for example, by hydroxy, acyloxy, carboxy or esterified carboxy, for example 1- or 2-naphthylacetyl, 2- or 3-α-naphthylpropionyl, 2- or 3-β-naphthyl-propionyl, 2-hydroxy-3-(α-or β-naphthyl)-propionyl, 2-acyloxy-3-(α- or β-naphthyl)-propionyl, for example 2-acetoxy-3-α-naphthylpropionyl or 2-pivaloyloxy-3-α-naphthyl-propionyl, 3-carboxy-4-α-naphthyl-butyryl, 3-carboxy-2-(α-naphthylmethyl)-propionyl, esterified carboxy-(α- or β-naphthyl)-butyryl, for example 3-benzyloxycarbonyl-4-onaphthylbutyryl, esterified carboxy-(α- or β-naphthylmethyl)-propionyl, for example 3-benzyloxycarbonyl-2-(α-naphthylmethyl)-propionyl, indenylcarbonyl, for example 1-, 2- or 3indenylcarbonyl, indanylcarbonyl, for example 1- or 2indanylcarbonyl, phenanthrenylcarbonyl, for example 9-phenanthrenylcarbonyl, optionally substituted pyrrolylcarbonyl, for example 2- or 3-pyrrolylcarbonyl or 4- or 5-phenylpyrrolyl-2-carbonyl, furylcarbonyl, for example 2-furylcarbonyl, thienylcarbonyl, for example 2-thienylcarbonyl, pyridylcarbonyl, for example 2-, 3- or 4-pyridylcarbonyl, optionally substituted indolylcarbonyl, for example 2-, 3- or 5-indolylcarbonyl, 1-methyl-, 5-methyl-, 5-methoxy-, 5-benzyloxy-, 5-chloro- or 4,5-dimethyl-indolyl-2carbonyl, 4,5,6,7-tetrahydroindolyl-2-carbonyl, optionally substituted quinolylcarbonyl, for example 2-, 3- or 4quinolylcarbonyl or 4-hydroxyquinolyl-2-carbonyl, optionally substituted isoquinolylcarbonyl, for example 1-, 3- or 4-isoquinolylcarbonyl or 1-oxo-1,2-dihydroisoquinolyl-3-carbonyl, 2-quinoxalinylcarbonyl, 2benzofuranylcarbonyl, benz[e]indolyl-2-carbonyl, β-carbolinyl-3-carbonyl, indolinylcarbonyl, for example 2or 3-indolinylcarbonyl, 1,2,3,4-tetrahydroquinolylcarbonyl, for example 1,2,3,4-tetrahydroquinolyl-2-, -3- or 4-carbonyl, 1,2,3,4-tetrahydroisoquinolylcarbonyl, for example 1,2,3,4-tetrahydroisoquinolyl-1-, -3- or -4carbonyl or 1-oxo-1,2,3,4-tetrahydroisoquinolyl-3carbonyl, or arylmethoxycarbonyl having one or two aryl radicals in which aryl is phenyl optionally mono-, di- or tri-substituted by lower alkyl, for example methyl or tert.-butyl, lower alkoxy, for example methoxy, hydroxy, halogen, for example chlorine, and/or by nitro, for example benzyloxycarbonyl, 4-nitrobenzyloxycarbonyl, diphenylmethoxycarbonyl or di-(4-methoxyphenyl)-methoxycarbonyl, oxamoyl or lower alkyloxamoyl, for example methyl- or ethyl-oxamoyl, and to pharmaceutically acceptable salts of these compounds having salt-forming groups.

The invention relates likewise to compounds of the formula I in which A represents the bivalent residue of the amino acids alanine, valine, norvaline, leucine, norleucine, serine, proline, phenylalanine, β-phenylserine, α-naphthylalanine, cyclohexylalanine, indoline-2-carboxylic acid, 1,2,3,4-tetrahydroisoquinoline-3-carboxylic acid, aspartic acid, asparagine, aminomalonic acid, aminomalonic acid monoamide, glutamic acid, glutamine, di-lower alkylglutamine, histidine, lysine or ornithine, it being possible for the carboxy group in the side chain of aspartic acid or glutamic acid to be esterified by a lower alkanol, for example methanol or tert.-butanol, for the hydroxy group in serine to be etherified by lower alkyl, for example methyl, or by benzyl, for the amino group in the side chain of lysine or ornithine to be acylated by lower alkanoyl, for example pivaloyl, by lower alkoxycarbonyl, for example tert.-butoxycarbonyl, or by arylmethoxycarbonyl, for example benzyloxycarbonyl, and/or for the α-nitrogen atom of the amino acids to be substituted by lower alkyl, for example methyl, and to pharmaceutically acceptable salts of these compounds having salt-forming groups.

Also especially preferred are compounds of the formula I in which $R_2$ represents hydrogen or lower alkyl, for example methyl, $R_3$ represents lower alkyl, for example isopropyl or isobutyl, cycloalkyl-lower alkyl, for example cyclohexylmethyl, or tricycloalkyl-lower alkyl, for example 1-adamantylmethyl, $R_4$ represents hydroxy and $R_5$ represents lower alkyl having 2 or more carbon atoms, for example isopropyl or tert.-butyl, cycloalkyl, for example cyclopentyl or cyclohexyl, cycloalkyl-lower alkyl, for example cyclohexylmethyl, 1-adamantyl, benzyl, carbamoyl or lower alkylcarbamoyl, for example methylcarbamoyl, and pharmaceutically acceptable salts of these compounds having salt-forming groups.

Likewise preferred are compounds of the formula I in which $R_6$ represents amino, alkylamino, for example methyl-, ethyl-, n-propyl-, isopropyl-, n-butyl-, isobutyl-, tert.-butyl-, n-pentyl-, isopentyl-, n-hexyl-, n-octyl- or n-decyl-amino, di-lower alkylamino, for example dimethylamino, hydroxy-lower alkylamino, for example 2-hydroxyethylamino, 1-hydroxybut-2-ylamino or tris(-hydroxymethyl)methylamino, carboxyalkylamino in which the carboxy radical is not in the 1-position of the alkyl radical, for example 4-carboxy-n-butyl-, 5-carboxy-n-pentyl-, 6-carboxy-n-hexyl-, 7-carboxy-n-heptyl- or 8-carboxy-n-octyl-amino, also dicarboxymethylamino, lower alkoxycarbonylalkylamino in which the carbonyl radical is not in the 1-position of the alkyl radical, for example 4-tert.-butoxycarbonyl-n-butyl-, 7-tert.-butoxycarbonyl-n-heptyl- or 8-tert.-butoxycarbonyl-n-octyl-amino, also di-lower alkoxycarbonyl-methylamino, for example di-methoxycarbonyl-methylamino, physiologically cleavable esterified carboxyalkylamino in which the ester function is not in the 1-position of the alkyl radical, for example 4-pivaloyloxymethoxycarbonyl-n-butylamino, 7-(1-ethoxycarbonyloxyethoxycarbonyl)-n-heptylamino or 7-pivaloyloxymethoxycarbonyl-n-heptylamino, carbamoyl or hydroxy-lower alkylcarbamoyl-alkylamino in which the carbamoyl radical is not in the 1-position of the alkyl radical, for example 4-carbamoyl-n-butylamino, 7-carbamoyl-n-heptylamino or 4-(tris-[hydroxymethyl]-methyl)-carbamoyl-n-butylamino, also dicarbamoylmethylamino, di-(lower alkylcarbamoyl)-methylamino, for example di-(methylcarbamoyl)-methylamino, di-(hydroxy-lower alkylcarbamoyl)-methylamino, for example di-(2-hydroxyethylcarbamoyl)-methylamino, or bis-(di-lower alkylcarbamoyl)-methylamino, for example bis-(dimethylcarbamoyl)-methylamino, amino-lower alkylamino, for example 2-aminoethylamino or 3-aminopropylamino, lower alkylamino-lower alkylamino, for example 2-methylaminoethylamino, di-lower alkylamino-lower alkylamino, for example 2-dimethylaminoethylamino, lower alkoxycarbonylamino-lower alkylamino, for example 2-(tert.-butoxycarbonylamino)-ethylamino, guanidino-lower alkylamino, for example 2-guanidinoethylamino, cycloalkyl-lower alkylamino, for example cyclopropylmethylamino, benzylamino, pyridyl-lower alkylamino, for example 2-, 3- or 4-pyridylmethylamino, 2-(2-, 3- or 4-pyridyl)-ethylamino or 3-(2-, 3- or 4-pyridyl)propylamino, imidazolyl-lower alkylamino, for example 4-imidazolylmethylamino or 2-(4-imidazolyl)-ethylamino, or indolyl-lower alkylamino, for example 3-indolylmethylamino or 2-(3-indolyl)-ethylamino, and to pharmaceutically acceptable salts of these compounds having salt-forming groups.

Preferred are compounds of the formula I in which $R_1$ represents lower alkanoyl, for example formyl, acetyl, propionyl or pivaloyl, 2-(o,o-dichloroanilino)-phenylacetyl, 2-(o,o-dichloro-n-benzylanilino)phenylacetyl, optionally substituted pyrrolylcarbonyl, for example 2- or 3-pyrrolylcarbonyl or 4- or 5-phenylpyrrolyl-2-carbonyl, furylcarbonyl, for example 2furylcarbonyl, thienylcarbonyl, for example 2-thienylcarbonyl, pyridylcarbonyl, for example 2-, 3- or 4-pyridylcarbonyl, optionally substituted indolylcarbonyl, for example 2-, 3- or 5-indolylcarbonyl, 1-methyl-, 5-methyl-, 5-methoxy-, 5-benzyloxy-, 5-chloro- or 4,5-dimethylindolyl-2-carbonyl, 4,5,6,7-tetrahydroindolyl-2-carbonyl, optionally substituted quinolylcarbonyl, for example 2-, 3- or 4-quinolylcarbonyl or 4-hydroxyquinolyl-2-carbonyl, optionally substituted isoquinolylcarbonyl, for example 1-, 3- or 4-isoquinolylcarbonyl or 1-oxo-1,2-dihydroisoquinolyl-3carbonyl, 2-quinoxalinylcarbonyl, 2-benzofuranylcarbonyl, benz[e]indolyl-2-carbonyl, β-carbolinyl-3carbonyl, indolinylcarbonyl, for example 2- or 3-indolinylcarbonyl, 1,2,3,4-tetrahydroquinolylcarbonyl, for example 1,2,3,4-tetrahydroquinolyl-2-, -3- or -4-carbonyl, 1,2,3,4-tetrahydroisoquinolylcarbonyl, for example 1,2,3,4-tetrahydroisoquinolyl-1-, -3- or -4carbonyl or 1-oxo-1,2,3,4-tetrahydroisoquinolyl-3carbonyl, A represents the bivalent residue of the amino acids norleucine, phenylalanine, cyclohexylalanine, glutamic acid, glutamine, $N^\delta$-dimethyl-glutamine, ornithine or $N^\delta$-pivaloyl-ornithine, $R_2$ represents hydrogen, $R_3$ represents isobutyl, cyclohexylmethyl or 1-adamantylmethyl, $R_4$ represents hydroxy, $R_5$ represents isopropyl, cyclohexyl, cyclohexylmethyl or methylcarbamoyl and $R_6$ represents lower alkylamino, for example methyl-, ethyl-, n-propyl-, isopropyl-, n-butyl- or isopentylamino, di-lower alkylamino, for example dimethylamino, hydroxy-lower alkylamino, for example 2-hydroxyethylamino or 1-hydroxybut-2-ylamino, carboxyalkylamino in which the carboxy radical is not in the 1-position of the alkyl radical, for example 4-carboxy-n-butylamino, 7-carboxy-n-heptylamino or 8-carboxy-n-octylamino, lower alkoxycarbonylalkylamino, in which the carbonyl radical is not in the 1-position of the alkyl radical, for example 4-tert.-butoxycarbonyl-n-butylamino or 7-tert.-butoxycarbonyl-n-hexylamino, amino-lower alkylamino, for example 2-ethylaminoethylamino, guanidino-lower alkylamino, for example 2-quanidinoethylamino, benzylamino or pyridyl-lower alkylamino, for example 2-pyridylmethylamino, and pharmaceutically acceptable salts of these compounds having salt-forming groups.

The invention relates especially to compounds of the formula I in which $R_1$ represents lower alkanoyl having from 1 to 7 carbon atoms, for example formyl, acetyl, propionyl or pivaloyl, phenoxy-lower alkanoyl, for example phenoxyacetyl, naphthoxy-lower alkanoyl, for example α- or β-naphthoxyacetyl, α-naphthoxycarboxy-lower alkanoyl, for example 2-α-naphthoxy-4 carboxy-butyryl, α-naphthoxy-lower alkoxycarbonyl-lower alkanoyl, for example α-naphthoxy-ethoxycarbonylacetyl, 2-α-naphthoxy-3-ethoxycarbonyl-propionyl or 2-α-naphthoxy-4-tert.-butoxycarbonyl-butyryl, α-naphthoxy-benzyloxycarbonyl-lower alkanoyl, for example 2-α-naphthoxy-3-benzyloxycarbonyl-propionyl, α-naphthoxy-carbamoyl-lower alkanoyl, for example 2-α-naphthoxy-4-carbamoyl-butyryl, α-naphthoxy-cyano-lower alkanoyl, for example α-naphthoxy-cyanoacetyl or 2-α-naphthoxy-4-cyano-butyryl, α-naphthoxy-di-lower alkylamino-lower alkanoyl, for example 2-α-naphthoxy-5-dimethylamino-pentanoyl, α-naphthoxy-oxo-lower alkanoyl, for example 2-α-naphthoxy-4-oxo-pentanoyl, phenyl-, α-naphthyl- or β-naphthyl-lower alkanoyl in which lower alkanoyl may be unsubstituted or substituted, for example, by hydroxy, lower alkoxy, acyloxy, carboxy, esterified carboxy, carbamoyl, substituted carbamoyl, cyano, phosphono, esterified phosphono, benzofuranyl and/or by oxo and is optionally branched, for example phenylacetyl, α-naphthylacetyl, β-naphthylacetyl, 3-phenylpropionyl, 3-α- or -β-naphthylpropionyl, 3-phenyl- or 3-α-naphthyl-2-hydroxy-propionyl, 3-phenyl- or 3-α-naphthyl-2-lower alkoxy-propionyl, such as 3-phenyl- or 3-α-naphthyl-2-neopentyloxypropionyl, 3-phenyl- or 3-α-naphthyl-2-acyloxypropionyl, such as 3-phenyl-2-pivaloyloxy- or -2-acetoxy-propionyl, 3-α-naphthyl-2-pivaloyloxy- or -2-acetoxy-propionyl, 3-α-naphthyl-2-acetoacetoxypropionyl, 3-α-naphthyl-2-ethylaminocarbonyloxypropionyl or 3-α-naphthyl-2-(2-amino- or 2-benzyloxycarbonylamino-2-methyl-propionyloxy)-propionyl, 3-phenyl- or 3-α-naphthyl-2-carboxymethyl-propionyl, 3-phenyl- or 3-α-naphthyl-2-lower alkoxycarbonylpropionyl, such as 3-α-naphthyl-2-ethoxycarbonylpropionyl, 3-phenyl- or 3-α-naphthyl-2benzyloxycarbonylmethyl-propionyl, 3-phenyl- or 3-α-naphthyl-2-carbamoyl-propionyl, 3-phenyl- or 3-α-naphthyl-2-tert.-butylcarbamoyl-propionyl, 3-phenyl- or 3-α-naphthyl-2-(2-dimethylaminoethyl)-carbamoyl-propionyl, 3-α-naphthyl-2-(carboxy- or tert.-butoxycarbonyl)-methylcarbamoyl-propionyl, 3-phenyl- or 3-α-naphthyl-2-(3-hydroxy-2-propyl)-carbamoyl-propionyl, 3-phenyl- or 3-α-naphthyl-2-(2,2-dimethoxyethyl)-carbamoyl-propionyl, 3-phenyl- or 3-α-naphthyl-2-(5-amino-5-carboxypentyl)-carbamoyl-propionyl, 3-phenyl- or 3-α-naphthyl-2-cyanopropionyl, 3-phenyl- or 3-α-naphthyl-2-cyanomethylpropionyl, 3-phenyl-2-phosphono- or -phosphonomethylpropionyl, 3-phenyl-2-dimethoxyphosphoryl- or -dimethoxyphosphorylmethyl-propionyl, 3-phenyl-2-diethoxyphosphoryl- or -diethoxyphosphorylmethylpropionyl, 3-phenyl-2-ethoxy- or -methoxy-hydroxyphosphoryl-propionyl, 3-phenyl- or 3-α-naphthyl-2-acetonylpropionyl, 3-phenyl- or 3-α-naphthyl-2-dimethylaminomethyl-propionyl, 2-benzyl- or 2-α-naphthylmethyl-4-cyano-butyryl, 4-phenyl- or 4-naphthyl-3-carboxybutyryl, 4-phenyl- or 4-α-naphthyl-3-benzyloxycarbonylbutyryl, 2-benzyl-4-(2-benzofuranyl)-4-oxo-butyryl, 2-benzyl- or 2-α-naphthylmethyl-4-oxopentanoyl, 2-benzyl- or 2-α-naphthylmethyl-4,4-dimethyl-3-oxo-pentanoyl, 2-benzyl- or 2-α-naphthylmethyl-5-dimethylaminopentanoyl, 2-benzyl- or 2-α-naphthylmethyl-5-dimethylamino-4-oxo-pentanoyl, 2-benzyl- or 2-α-naphthylmethyl-5,5-dimethyl-4-oxo-hexanol, α,p-diaminophenylacetyl, α,p-diacylamino-phenylacetyl, such as α,p-dibenzyloxycarbonylamino-phenylacetyl or α-pivaloylamino-p-benzyloxycarbonylaminophenylacetyl, also 2-(o,o-dichloroanilino)-phenylacetyl or 2-(o,o-dichloro-N-benzylanilino)-phenylacetyl, naphthylcarbonyl, for example α- or β-naphthylcarbonyl or 1,8-naphthalenedicarbonyl, pyrrolylcarbonyl, for example 2- or 3-pyrrolylcarbonyl, cyclohepta[b]pyrrolyl-5-carbamoyl, indolylcarbonyl, for example 2-, 3- or 5-indolylcarbonyl, 1-benzylindolyl-3-carbonyl, 4,5,6,7-tetrahydroindolyl-2-carbonyl, quinolylcarbonyl, for example 2-, 3- or 4-quinolylcarbonyl, or oxamoyl, A represents the bivalent residue of the amino acids leucine, norleucine, phenylalanine, n-methyl-phenylalanine, β-phenylserine, cyclohexylalanine, glutamine, histidine or N-methyl-histidine, $R_2$ represents hydrogen, $R_3$ represents isobutyl or cyclohexylmethyl, $R_4$ represents hydroxy, $R_5$ represents isopropyl, cyclohexylmethyl, α-decahydronaphthyl or dimethylamino and $R_6$ represents lower alkylamino having from 1 to 7 carbon atoms, for example methyl-, ethyl-, n-propyl-, isopropyl-, n-butyl-, isobutyl-, n-pentyl- or isopentylamino, di-lower alkylamino, for example dimethylamino, hydroxy-lower alkylamino, for example 2-hydroxyethylamino, 1-hydroxybut-2-ylamino or 5-hydroxypentylamino, 2-phenoxyethylamino, 2-(3-carbamoyl-4-hydroxyphenoxy)-ethylamino, carboxyalkylamino or amino-carboxy-alkylamino in which the carboxy radical is not in the 1-position of the alkyl radical, for example 4-carboxy-n-butylamino, 5-amino-5-carboxy-n-pentylamino, 7-carboxy-n-heptylamino or 8-carboxy-n-octylamino, lower alkoxycarbonylalkylamino or acylamino-lower alkoxycarbonylalkylamino in which the carbonyl radical is not in the 1-position of the alkyl radical, for example 4-tert.-butoxycarbonyl-n-butylamino, 5-tert.-butoxycarbonylamino-5-methoxycarbonyl-n-pentylamino or 7-tert.-butoxycarbonyl-n-heptylamino, 4-tris-(hydroxymethyl)methylcarbamoyl-n-butylamino, amino-lower alkylamino, for example 2-aminoethylamino, di-lower alkylamino-lower alkylamino, for example 2-dimethylaminoethylamino or 3-dimethylaminopropylamino, lower alkoxycarbonylamino-lower alkylamino, for example 2-tert.-butoxycarbonylaminoethylamino, morpholino-lower alkylamino, for example 2-morpholinoethylamino, cycloalkyl-lower alkylamino, for example cyclopropylmethylamino or cyclohexylmethylamino, benzylamino, pyridyl-lower alkylamino, for example 2-pyridylmethylamino, or imidazolyl-lower alkylamino, for example 2-(4-imidazolyl)-ethylamino or 2-(2-[4-imidazolyl]-ethylamino)-ethylamino, and to pharmaceutically acceptable salts of these compounds having salt-forming groups.

The invention relates more especially to compounds of the formula I in which $R_1$ represents phenoxy-lower alkanoyl, for example phenoxyacetyl, naphthoxy-lower alkanoyl, for example α- or β-naphthoxyacetyl, phenyl-lower alkanoyl in which lower alkanoyl may be unsubstituted or substituted, for example, by acyloxy, such as lower alkanoyloxy, carboxy, esterified carboxy, such as lower alkoxycarbonyl, carbamoyl, substituted carbamoyl, such as lower alkylcarbamoyl, cyano, esterified phosphono, such as di-lower alkoxyphosphoryl, or by lower alkyl and oxo or by benzofuranyl and oxo and is optionally branched, for example 3-phenylpropionyl, 2-acetoxy-3-phenyl-propionyl, 2-pivaloyloxy-3-phenylpropionyl, 2-ethoxy- or -methoxy-carbonyl-3-phenylpropionyl, 2-tert.-butylcarbamoyl-3-phenylpropionyl, 2-benzyl-3-cyano-propionyl, 2-dimethoxyphosphoryl-3-phenyl-propionyl, 2-benzyl-5,5-dimethyl-4-oxo-hexanoyl, 2-benzyl-4,4-dimethyl-3-oxo-pentanoyl or 4-(2-benzofuranyl)-2-benzyl-4-oxo-butyryl, naphthyl-lower alkanoyl in which lower alkanoyl may be unsubstituted or substituted, for example by acyloxy, such as lower alkanoyloxy, carboxy, esterified carboxy, such as lower alkoxycarbonyl, unsubstituted or substituted carbamoyl, cyano or by lower alkyl and oxo and is optionally branched, for example 3-α- or β-naphthyl-propionyl, 2-acetoxy-3-α-naphthyl-propionyl, 2-pivaloyloxy-3-α-naphthyl-propionyl, 2-ethoxy- or methoxy-carbonyl-3-α-naphthyl-propionyl, 2-carbamoyl-3-α-naphthyl-propionyl, 2-tert.-butylcarbamoyl-3-α-naphthyl-propionyl, 2-carboxymethylcarbamoyl-3-α-naphthyl-propionyl, 3-cyano-2-α-naphthylmethylpropionyl, 5,5-dimethyl-2-α-naphthylmethyl-4-oxo-hexanoyl or 4,4-dimethyl-2-α-naphthylmethyl-3-oxo-pentanoyl, indolyl-2-carbonyl or cyclohepta[b]pyrrolyl5-carbonyl, A represents the bivalent residue of the amino acid L-histidine, $R_2$ represents hydrogen, $R_3$ represents isobutyl or cyclohexylmethyl, $R_4$ represents hydroxy, $R_5$ represents isopropyl or cyclohexylmethyl and $R_6$ represents lower alkylamino, for example methyl-, ethyl-, n-propyl-, isopropyl-, n-butyl-, isobutyl-, n-pentyl- or isopentyl-amino or aminocarboxy-lower alkylamino in which the substituents are not in the 1-position of the lower alkyl radical, for example 5-amino-5-carboxy-pentylamino, and the carbon atoms carrying the radicals $R_3$ and $R_4$ have the S-configuration, and also to pharmaceutically acceptable salts of these compounds.

The invention relates more especially to compounds of the formula I in which $R_1$ represents phenyl- or α-naphthyl-lower alkanoyl that is substituted in the lower-alkanoyl radical by lower alkanoyloxy, lower alkoxycarbonyl, lower alkylcarbamoyl, di-lower alkoxyphosphoryl or by lower alkyl and oxo and in which lower alkyl has from 1 to 7 carbon atoms, for example 2(S)-pivaloyloxy-3-phenyl-propionyl, 2(R)- and 2(S)-dimethoxyphosphoryl-3-phenyl-propionyl, 2(R)- and 2(S)-benzyl-5,5-dimethyl-4-oxo-hexanoyl, 2(R)- and 2(S)-benzyl-4,4-dimethyl-3-oxo-pentanoyl, 2(R)- and 2(S)-tert.-butylcarbamoyl-3-α-naphthyl-propionyl or 2(R)- and 2(S)-ethoxycarbonyl-3-α-naphthyl-propionyl, also indolyl-2-carbonyl or cyclohepta[b]pyrrolyl-5-carbonyl, A represents the bivalent residue of the amino acid L-histidine, $R_2$ represents hydrogen, $R_3$ represents cyclohexylmethyl, $R_4$ represents hydroxy, $R_5$ represents isopropyl and $R_6$ represents lower alkylamino having from 1 to 7 carbon atoms, for example methyl-, ethyl-, n-propyl-, isopropyl-, n-butyl-, isobutyl-, n-pentyl- or isopentyl-amino, and the carbon atoms carrying the radicals $R_3$, $R_4$ and $R_5$ have the S-configuration, and also to pharmaceutically acceptable salts of these compounds.

The invention relates first and foremost to the compounds mentioned in the Examples and to their pharmaceutically acceptable salts, especially the compound of the formula I in which $R_1$ represents 2(S)-pivaloyloxy-3-phenyl-propionyl, A represents the bivalent residue of the amino acid L-histidine, $R_2$ represents hydrogen, $R_3$ represents cyclohexylmethyl, $R_4$ represents hydroxy, $R_5$ represents isopropyl and $R_6$ represents n-butylamino, and the carbon atoms carrying the radicals $R_3$, $R_4$ and $R_5$ have the S-configuration, and its pharmaceutically acceptable salts, the compounds of the formula I in which $R_1$ represents 2(R,S)-, 2(R)- or 2(S)-dimethoxyphosphoryl-3-phenylpropionyl, A represents the bivalent residue of the amino acid L-histidine, $R_2$ represents hydrogen, $R_3$ represents cyclohexylmethyl, $R_4$ represents hydroxy, $R_5$ represents isopropyl and $R_6$ represents n-butylamino, and the carbon atoms carrying the radicals $R_3$, $R_4$ and $R_5$ have the S-configuration, and their pharmaceutically acceptable salts, the compounds of the formula I in which $R_1$ represents 2(R,S)-, 2(R)- or 2(S)-benzyl-5,5-dimethyl-4-oxohexanoyl, A represents the bivalent residue of the amino acid L-histidine, $R_2$ represents hydrogen, $R_3$ represents cyclohexylmethyl, $R_4$ represents hydroxy, $R_5$ represents isopropyl and $R_6$ represents n-butylamino, and the carbon atoms carrying the radicals $R_3$, $R_4$ and $R_5$ have the S-configuration, and their pharmaceutically acceptable salts, the compound of the formula I in which $R_1$ represents 2(R,S)-benzyl-4,4-dimethyl-3-oxo-pentanoyl, A represents the bivalent residue of the amino acid L-histidine, $R_2$ represents hydrogen, $R_3$ represents cyclohexylmethyl, $R_4$ represents hydroxy, $R_5$ represents isopropyl and $R_6$ represents n-butylamino and the carbon atoms carrying the radicals $R_3$, $R_4$ and $R_5$ have the S-configuration, and its pharmaceutically acceptable salts, the compound of the formula I in which $R_1$ represents 2(R,S)-ethoxycarbonyl-3-α-naphthyl-propionyl, A represents the bivalent residue of the amino acid L-histidine, $R_2$ represents hydrogen, $R_3$ represents cyclohexylmethyl, $R_4$ represents hydroxy, $R_5$ represents isopropyl and $R_6$ represents n-butylamino, and the carbon atoms carrying the radicals $R_3$, $R_4$ and $R_5$ have the S-configuration, and its pharmaceutically acceptable salts, the compound of the formula I in which $R_1$ represents cyclohepta[b]pyrrolyl-5-carbonyl, A represents the bivalent residue of the amino acid L-histidine, $R_2$ represents hydrogen, $R_3$ represents cyclohexylmethyl, $R_4$ represents hydroxy, $R_5$ represents isopropyl and $R_6$ represents n-butylamino, and the carbon atoms carrying the radicals $R_3$, $R_4$ and $R_5$ have the S-configuration, and its pharmaceutically acceptable salts, and the compound of the formula I in which $R_1$ represents 2(S)-pivaloyloxy-3-phenyl-propionyl, A represents the bivalent residue of the amino acid L-histidine, $R_2$ represents hydrogen, $R_3$ represents isobutyl, $R_4$ represents hydroxy, $R_5$ represents cyclohexylmethyl and $R_6$ represents n-butylamino, and the carbon atoms carrying the radicals $R_3$ and $R_4$ have the S-configuration, and its pharmaceutically acceptable salts.

Processes

The compounds of the formula I according to the invention and salts of such compounds having at least one salt-forming group are obtained according to processes that are known per se, for example as follows:

(a) a fragment of a compound of the formula I having a terminal carboxy group or a reactive acid derivative of that fragment is condensed with a fragment that is complementary to the compound of the formula I and has a free amino group or with a reactive derivative thereof having an activated amino group to form an amide bond, any free functional groups present in the reactants, with the exception of the groups participating in the reaction, optionally being in protected form, or (b) for the manufacture of a compound of the formula I in which $R_4$ represents hydroxy, the keto group in a compound of the formula

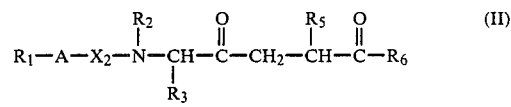

in which the substituents have the meanings mentioned and free functional groups, with the exception of the keto group participating in the reaction, are optionally in protected form, is reduced to a hydroxy group by reaction with a suitable reducing agent, or (c) for the manufacture of a compound of the formula I in which $R_4$ represents hydroxy, an aldehyde compound of the formula

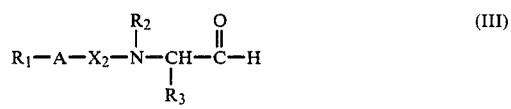

in which the substituents have the meanings mentioned and free functional groups, with the exception of the aldehyde group, are optionally in protected form, is reacted with an organometal compound of the formula

in which the substituents have the meanings mentioned and M represents a metal radical, and the resulting addition product is hydrolysed, or (d) in a compound of the formula

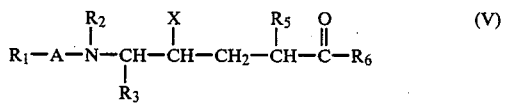
(V)

in which X represents a nucleofugal leaving group, the other substituents have the meanings mentioned above and free functional groups are optionally in protected form, the substituent X is exchanged for $R_4$ with a reagent that introduces the substituent $R_4$ in nucleophilic form, or (e) in a compound of the formula

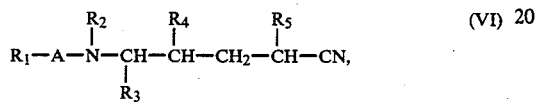
(VI)

in which the substituents have the meanings mentioned and any functional groups present are optionally in protected form, the cyano group is converted into an N-substituted carboxamido group —(C=O)$R_6$, or (f) for the manufacture of a compound of the formula I in which $R_4$ represents free hydroxy, an epoxide of the formula

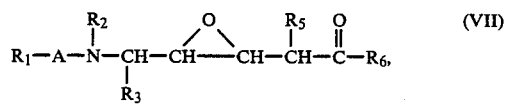
(VII)

in which the substituents have the meanings mentioned and free functional groups are optionally in protected form, is reduced to the corresponding alcohol with a regioselective reducing agent and, if desired, (g) any protecting groups present in a resulting compound are removed and/or, if desired, after carrying out one of the processes (a)–(f) mentioned above or any other process for the manufacture of a compound of the formula I, a resulting compound of the formula I having a salt-forming group is converted into its salt or a resulting salt is converted into the free compound or into a different salt and/or resulting isomeric mixtures are optionally separated and/or, in a resulting compound of the formula I, the configuration of a chiral carbon atom is reversed and/or a compound of the formula I according to the invention is converted into a different compound of the formula I according to the invention.

The invention relates also to the compounds other than compounds of the formula I, obtainable according to any one of the processes mentioned above (by-product), and to compounds of the formula I and salts thereof that have been manufactured by a process other than one of those mentioned hereinbefore.

Process (a) (Production of an amide bond):

Fragments of a compound of the formula I having a terminal carboxy group that can be condensed with a fragment complementary to a compound of the formula I to form an amide bond are, for example, compounds of the formulae: $R_1$—OH, $R_1$—A—OH or

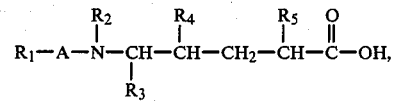

the activated esters or reactive anhydrides derived from these compounds, and also reactive cyclic amides. The reactive acid derivatives can also be formed in situ.

Activated esters are especially esters that are unsaturated at the linking carbon atom of the esterifying radical, for example of the vinyl ester type, such as vinyl esters (obtainable, for example, by transesterification of a corresponding ester with vinyl acetate; activated vinyl ester method), carbamoylvinyl esters (obtainable, for example, by treatment of the corresponding acid with an isoxazolium reagent; 1,2-oxazolium or Woodward method), or 1-lower alkoxyvinyl esters (obtainable, for example, by treatment of the corresponding acid with a lower alkoxyacetylene; ethoxyacetylene method), or esters of the amidino type, such as N,N'-disubstituted amidino esters (obtainable, for example, by treatment of the corresponding acid with a suitable N,N'-disubstituted carbodiimide, for example N,N'-dicyclohexyl carbodiimide; carbodiimide method), or N,N-disubstituted amidino esters (obtainable, for example, by treatment of the corresponding acid with an N,N-disubstituted cyanamide; cyanamide method), suitable aryl esters, especially phenyl esters suitably substituted by electron-attracting substituents (obtainable, for example, by treatment of the corresponding acid with a suitably substituted phenol, for example 4-nitrophenol, 4-methylsulphonylphenol, 2,4,5-trichlorophenol, 2,3,4,5,6-pentachlorophenol or 4-phenyldiazophenol, in the presence of a condensation agent, such as N,N'-dicyclohexyl carbodiimide; activated aryl esters method), cyanomethyl esters (obtainable, for example, by treatment of the corresponding acid with chloroacetonitrile in the presence of a base; cyanomethyl esters method), thio esters, especially phenylthio esters optionally substituted, for example, by nitro (obtainable, for example, by treatment of the corresponding acid with thiophenols that are optionally substituted, for example, by nitro, inter alia with the aid of the anhydride or carbodiimide method; activated thio esters method), or especially amino or amido esters (obtainable, for example, by treatment of the corresponding acid with an N-hydroxyamino or N-hydroxyamido compound, for example N-hydroxysuccinimide, N-hydroxypiperidine, N-hydroxyphthalimide, N-hydroxy-5-norbornene-2,3-dicarboxylic acid imide, 1-hydroxybenzotriazole or 3-hydroxy-3,4-dihydro-1,2,3-benzotriazin-4-one, for example according to the anhydride or carbodiimide method; activated N-hydroxyesters method).

Anhydrides of acids may be symmetric or preferably mixed anhydrides of these acids, for example anhydrides with inorganic acids, such as acid halides, especially acid chlorides (obtainable, for example, by treating the corresponding acid with thionyl chloride, phosphorus pentachloride or oxalyl chloride; acid chloride method), azides (obtainable, for example, from a corresponding acid ester by way of the corresponding hydrazide and the treatment of the latter with nitrous acid; azide method), anhydrides with carbonic acid semi-esters, for example carbonic acid lower alkyl semi-esters (obtainable, for example, by treating the corresponding acid with chloroformic acid lower alkyl esters, or with a 1-lower alkoxycarbonyl-2-lower alkoxy-1,2-dihydroquinoline, for example 1-lower alkoxycarbonyl-2-ethoxy-1,2-dihydroquinoline; mixed -alkylcarbonic acid anhydrides method), or anhydrides with dihalogenated, especially dichlorinated, phosphoric acid (obtainable, for example, by treating the corresponding acid with phosphorus oxychloride; phosphorus oxychloride method), anhydrides with other phosphoric acid derivatives (for example those which can be obtained with phenyl-N-phenylphosphoramidochloridate) or with phosphorous acid derivatives, or anhydrides with organic acids, such as mixed anhydrides with organic carboxylic acids (obtainable, for example, by treating the corresponding acid with an optionally substituted lower alkanecarboxylic acid halide or phenyl-lower alkanecarboxylic acid halide, for example phenylacetic acid chloride, pivalic acid chloride or trifluoroacetic acid chloride; mixed carboxylic acid anhydrides method) or with organic sulphonic acids (obtainable, for example, by treating a salt, such as an alkali metal salt, of the corresponding acid with a suitable organic sulphonic acid halide, such as a lower alkanesulphonic acid chloride or arylsulphonic acid chloride, for example methane- or p-toluene-sulphonic acid chloride; mixed sulphonic acid anhydrides method), and symmetric anhydrides (obtainable, for example, by condensing the corresponding acid in the presence of a carbodiimide or of 1-diethylaminopropyne; symmetric anhydrides method).

Suitable cyclic amides are especially amides having five-membered diazacycles of aromatic character, such as amides with imidazoles, for example imidazole (obtainable, for example, by treating the corresponding acid with N,N'-carbonyldiimidazole; imidazole method), or pyrazole, for example 3,5-dimethylpyrazole (obtainable, for example, by way of the acid hydrazide by treatment with acetylacetone; pyrazolide method).

Fragments having a free amino group that are complementary to the compound of the formula I are, for example, depending on the meaning of $R_6$, a primary or secondary amine, or also compounds of the formula:

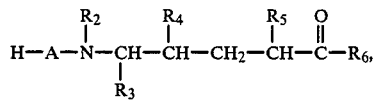

or

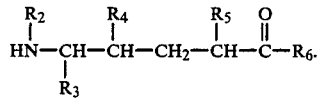

The amino group participating in the reaction in a fragment complementary to a compound of the formula I is preferably in free form, especially if the carboxy group reacting therewith is in reactive form; it can also, however, itself be derivatised, for example by reaction with a phosphite, such as diethylchlorophosphite, 1,2-phenylenechlorophosphite, ethyldichlorophosphite, ethylenechlorophosphite or tetraethylpyrophosphite. A derivative of such a complementary fragment having an amino group is, for example, also a carbamic acid halide or an isocyanate, the amino group participating in the reaction being substituted by halocarbonyl, for example chlorocarbonyl, or modified as the isocyanate group, it being possible in the latter case to obtain only compounds of the formula I that have a hydrogen atom at the nitrogen atom of the amide group formed by the reaction.

If the complementary fragment having an amino group is an amine mono- or di-substituted by lower alkyl or aryl-lower alkyl then a corresponding urea compound also constitutes a reactive derivative. For example, on heating equimolar amounts of this urea compound and the component having a free carboxy group, corresponding compounds of the formula I are obtained.

If the complementary fragment is dimethylamine then dimethylformamide is also a reactive derivative.

Functional groups in starting materials, the reaction of which is to be avoided, especially carboxy, amino, hydroxy and mercapto groups, can be protected by suitable protecting groups (conventional protecting groups) that are customarily used in the synthesis of peptide compounds and also of cephalosporins and penicillins. These protecting groups may already be present in the precursors and are intended to protect the functional groups in question against undesired side-reactions, such as acylation, etherification, esterification, oxidation, solvolysis, etc.. Protecting groups may, however, also be present in the end products. Compounds of the formula I having protected functional groups can have a higher metabolic stability than can the corresponding compounds having free functional groups.

The protection of functional groups by such protecting groups, the protecting groups themselves and deprotection reactions are described, for example, in standard works, such as in J. F. W. McOmie, "Protective Groups in Organic Chemistry", Plenum Press, London and New York 1973, in Th. W. Greene, "Protective Groups in Organic Synthesis", Wiley, New York 1981, in "The Peptides", volume 3 (edited by E. Gross and J. Meienhofer), Academic Press, London and New York 1981, and in "Methoden der organischen Chemie", Houben-Weyl, 4th edition, vol. 15/1, Georg Thieme Verlag, Stuttgart 1974.

A carboxy group is protected, for example, in the form of an ester group that is selectively cleavable under mild conditions. A carboxy group protected in esterified form is esterified especially by a lower alkyl group that is branched in the 1-position of the lower alkyl group or substituted by suitable substituents in the 1- or 2-position of the lower alkyl group.

A protected carboxy group esterified by a lower alkyl group that is branched in the 1-position of the lower alkyl group is, for example, tert.-lower alkoxycarbonyl, for example tert.-butoxycarbonyl, arylmethoxycarbonyl having one or two aryl radicals in which aryl is unsubstitued phenyl or phenyl mono-, di- or tri-substituted, for example, by lower alkyl, for example tert.-lower alkyl, such as tert.-butyl, lower alkoxy, for example methoxy, hydroxy, halogen, for example chlorine, and/or by nitro, for example benzyloxycarbonyl, benzyloxycarbonyl substituted by the mentioned substituents, for example 4-nitrobenzyloxycarbonyl or 4-methoxybenzyloxycarbonyl, diphenylmethoxycarbonyl or diphenylmethoxycarbonyl substituted by the mentioned substituents, for example di-(4-methoxyphenyl)-methoxycarbonyl.

A protected carboxy group esterified by a lower alkyl group that is substituted by suitable substituents in the 1- or 2-position of the lower alkyl group is, for example, 1-lower alkoxy-lower alkoxycarbonyl, for example methoxymethoxycarbonyl, 1-methoxyethoxycarbonyl or 1-ethoxyethoxycarbonyl, 1-lower alkylthiolower alkoxycarbonyl, for example 1-methylthiomethoxycarbonyl or 1-ethylthioethoxycarbonyl, aroylmethoxycarbonyl, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, and also 2-tri-lower alkylsilyl-lower alkoxycarbonyl, for example 2-trimethylsilylethoxycarbonyl.

A carboxy group can also be protected as an organic silyloxycarbonyl group. An organic silyloxycarbonyl group is, for example, a tri-lower alkylsilyloxycarbonyl group, for example trimethylsilyloxycarbonyl. The silicon atom of the silyloxycarbonyl group may also be substituted by two lower alkyl groups, for example methyl groups, and by the amino group or the carboxy group of a second molecule of the formula I. Compounds having such protecting groups can be manufactured, for example, with dimethylchlorosilane as the silylating agent.

A protected carboxy group is preferably tert.-lower alkoxycarbonyl, for example tert.-butoxycarbonyl, benzyloxycarbonyl, 4-nitrobenzyloxycarbonyl or diphenylmethoxycarbonyl.

An amino group can be protected, for example, in the form of an acylamino, arylmethylamino, etherified mercaptoamino or silylamino group or in the form of an azido group.

In a corresponding acylamino group, acyl is, for example, the acyl radical of an organic carboxylic acid having, for example, up to 18 carbon atoms, especially of a lower alkanecarboxylic acid that is optionally substituted, for example, by halogen or aryl, or of benzoic acid that is optionally substituted, for example, by halogen, lower alkoxy or nitro, or preferably of a carbonic acid semi-ester. Such acyl groups are, for example, lower alkanoyl, such as formyl, acetyl, propionyl or pivaloyl, halo-lower alkanoyl, for example 2-haloacetyl, such as 2-chloro-, 2-bromo-, 2-iodo-, 2,2,2-trifluoro- or 2,2,2-trichloroacetyl, benzoyl optionally substituted, for example, by halogen, lower alkoxy or nitro, for example benzoyl, 4-chlorobenzoyl, 4-methoxybenzoyl or 4-nitrobenzoyl, or lower alkoxycarbonyl that is branched in the 1-position of the lower alkyl radical or suitably substituted in the 1- or 2-position, for example tert.-lower alkoxycarbonyl, such as tert.-butoxycarbonyl, arylmethoxycarbonyl having one or two aryl radicals which are phenyl optionally mono- or poly-substituted, for example, by lower alkyl, for example tert.-lower alkyl, such as tert.-butyl, lower alkoxy, such as methoxy, hydroxy, halogen, such as chlorine, and/or by nitro, for example benzyloxycarbonyl, 4-nitrobenzyloxycarbonyl, diphenylmethoxycarbonyl or di-(4-methoxyphenyl)-methoxycarbonyl, aroylmethoxycarbonyl, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, 2-tri-lower alkylsilyl-lower alkoxycarbonyl, for example 2-trimethylsilylethoxycarbonyl, or 2-triarylsilyl-lower alkoxycarbonyl, for example 2-triphenylsilylethoxycarbonyl.

An arylmethylamino group is, for example, mono-, di- or especially tri-phenylmethylamino, for example benzyl-, diphenylmethyl- or trityl-amino.

In an etherified mercaptoamino group, the etherified mercapto group is especially substituted arylthio, for example 4-nitrophenylthio.

A silylamino group is, for example, a tri-lower alkylsilylamino group, for example trimethylsilylamino. The silicon atom of the silylamino group can also be substituted by only two lower alkyl groups, for example methyl groups, and by the amino group or carboxy group of a second molecule of the formula I. Compounds having such protecting groups can be manufactured, for example, with dimethylchlorosilane as the silylating agent.

Preferred amino-protecting groups are acyl radicals of carbonic acid semi-esters, especially tert.-butoxycarbonyl, optionally substituted benzyloxycarbonyl, for example 4-nitrobenzyloxycarbonyl, diphenylmethoxycarbonyl, 2-halo-lower alkoxycarbonyl, for example 2,2,2-trichloroethoxycarbonyl, and also trityl or formyl.

A hydroxy group can be protected, for example, by an acyl group, for example by halo-substituted, for example chloro-substituted, lower alkanoyl, for example 2,2-dichloroacetyl, or especially by an acyl radical of a carbonic acid semi-ester mentioned for protected amino groups. A preferred hydroxy-protecting group is, for example, 2,2,2-trichloroethoxycarbonyl, 4-nitrobenzyloxycarbonyl, diphenylmethoxycarbonyl or trityl. A hydroxy group can also be protected by tri-lower alkylsilyl, for example trimethylsilyl or dimethyltert.-butylsilyl, a readily removable alkyl group, such as tert.-lower alkyl, for example tert.-butyl, an oxa- or a thia-aliphatic or -cycloaliphatic hydrocarbon radical, for example 1-lower alkoxy-lower alkyl or 1-lower alkylthio-lower alkyl, for example methoxymethyl, 1-methoxyethyl, 1-ethoxyethyl, methylthiomethyl, 1-methylthioethyl or 1-ethylthioethyl, or 2-oxa- or 2-thia-cycloalkyl having from 5 to 7 ring atoms, for example 2-tetrahydrofuryl or 2-tetrahydropyranyl, or a corresponding thia analogue, or also by 1-phenyl-lower alkyl, for example benzyl, diphenylmethyl or trityl, it being possible for the phenyl radicals to be substituted, for example, by halogen, for example chlorine, lower alkoxy, for example methoxy, and/or by nitro.

Two adjacent hydroxy groups can be protected, for example, by a preferably substituted methylene group, for example by lower alkylidene, for example isopropylidene, cycloalkylidene, for example cyclohexylidene, or benzylidene.

A mercapto group, such as, for example, in cysteine, can be protected especially by S-alkylation with optionally substituted alkyl radicals, thioacetal formation, S-acylation or by the formation of asymmetric disulphide groupings. Preferred mercaptoprotecting groups are, for example, benzyl optionally substituted in the phenyl radical, for example by methoxy or nitro, such as 4-methoxybenzyl, diphenylmethyl optionally substituted in the phenyl radical, for example by methoxy, such as 4,4'-dimethoxydiphenylmethyl, triphenylmethyl, trimethylsilyl, benzylthiomethyl, tetrahydropyranyl, acylaminomethyl, benzoyl, benzyloxycarbonyl or lower alkylaminocarbonyl, such as ethylaminocarbonyl.

The condensation for the production of the amide bond can be carried out in a manner known per se, for example as described in standard works, such as Houben-Weyl, "Methoden der organischen Chemie", 4th edition, vol. 15/II, Georg Thieme Verlag, Stuttgart 1974, "The Peptides" (edited by E. Gross and J. Meienhofer), volumes 1 and 2, Academic Press, London and New York 1979/1980, or M. Bodanszky, "Principles of Peptide Synthesis", Springer-Verlag, Berlin 1984.

The condensation can be carried out in the presence of one of the customary condensation agents. Customary condensation agents are, for example, carbodiimides, for example diethyl, dipropyl or N-ethyl-N'-(3-dimethylaminopropyl) carbodiimide or especially dicyclohexyl carbodiimide, also suitable carbonyl compounds, for example carbonyldiimidazole, 1,2-oxazolium compounds, for example 2-ethyl-5-phenyl-1,2-oxazolium 3'-sulphonate and 2-tert.-butyl-5-methylisoxazolium perchlorate, or a suitable acylamino compound, for example 2-ethoxy-1-ethoxycarbonyl-1,2-dihydroquinoline, or activated phosphates, for example diphenylphosphoryl azide, diethylphosphoryl cyanide or phenyl-N-phenylphosphoramidochloridate.

If desired, an organic base is added, for example a tri-lower alkylamine having voluminous radicals, for example ethyldiisopropylamine, or a heterocyclic base, for example pyridine, 4-dimethylaminopyridine or preferably N-methylmorpholine.

The condensation of acid anhydrides with amines can be effected, for example, in the presence of inorganic carbonates, for example alkali metal carbonates or bicarbonates, such as sodium or potassium carbonate or sodium or potassium bicarbonate (customarily together with a sulphate).

The condensation is preferably carried out in an inert, polar, aprotic, preferably anhydrous solvent or solvent mixture, for example in a carboxylic acid amide, for example formamide or dimethylformamide, a halogenated hydrocarbon, for example methylene chloride, carbon tetrachloride or chlorobenzene, a ketone, for example acetone, a cyclic ether, for example tetrahydrofuran, an ester, for example ethyl acetate, or a nitrile, for example acetonitrile, or in mixtures thereof, optionally at reduced or elevated temperature, for example within a temperature range of from approximately −40° C. to approximately +100° C., preferably from approximately −10° C. to approximately +50° C., and optionally under an inert gas atmosphere, for example a nitrogen atmosphere.

Reactive acid derivatives can also be formed in situ. Thus, for example, N,N'-disubstituted amidino esters can be formed in situ by reacting the mixture of the fragment having a free carboxy group and the complementary fragment having an amino group in the presence of a suitable disubstituted carbodiimide, for example dicyclohexyl carbodiimide. Amino or amido esters of such acids can also be formed in the presence of the amino component to be acylated, by reacting the mixture of the corresponding acid and amino starting materials in the presence of a disubstituted carbodiimide, for example dicyclohexyl carbodiimide, and an N-hydroxylamine or N-hydroxyamide, for example N-hydroxybenzotriazole, N-hydroxysuccinimide or N-hydroxy-5-norbornene-2,3-dicarboxylic acid imide, optionally in the presence of a suitable base, for example 4-dimethylaminopyridine, N-methylmorpholine or ethyldiisopropylamine.

Process (b) Reduction of a keto group):

In a starting material of the formula II functional groups, with the exception of the keto group to be reduced, are optionally protected by one of the protecting groups mentioned under process (a).

For the reduction of the keto group in a compound of the formula II there are suitable those reducing agents which, under the reaction conditions of the process, reduce an isolated keto group selectively or more rapidly than the amide groups present in compounds of the formula I.

These are to be mentioned, especially, suitable borohydrides, such as alkali metal borohydrides, especially sodium borohydride, lithium borohydride or sodium cyanoborohydride, or suitable aluminium hydrides, such as alkali metal lower alkoxyaluminium hydrides having voluminous radicals, for example lithium tris-tert.-butoxyaluminium hydride.

The reduction can also be carried out with hydrogen in the presence of suitable heavy metal catalysts, for example Raney nickel or platinum or palladium catalysts, for example platinum on active carbon or palladium on active carbon, or according to the Meerwein-Pondorf-Verley method with the aid of aluminium alkoxides, preferably aluminium 2-propoxide or 2-ethoxide.

The reduction can preferably be carried out with stoichiometric amounts or with a reasonably proportioned excess of the reducing agent, in an inert solvent at temperatures of from −80° C. to the boiling point of the solvent, preferably from −20° C. to +100° C., if necessary under a protective gas, for example nitrogen or argon. An excess of the reducing agent is necessary especially in cases where that agent also reacts with the solvent, for example with the protons of a protic solvent.

Suitable solvents when using sodium borohydride are polar, protic solvents, for example methanol, ethanol or isopropanol, and, when using the other reducing agents, the polar, aprotic solvents mentioned under process (a), for example tetrahydrofuran.

Process (c) (Addition of an organometal compound):

In a starting material of the formula III functional groups, with the exception of the aldehyde group, are optionally protected by the protecting groups mentioned under process (a). Functional groups present in a compound of the formula IV are likewise protected.

In a compound of the formula IV a metal radical —M is, for example, —Li or —MgHal, for example —MgCl, —MgBr or —MgI.

The reaction of a compound of the formula III with a compound of the formula IV is effected in customary manner in an anhydrous, inert, aprotic solvent, for example in an ether, such as diethyl ether or tetrahydrofuran, or a hydrocarbon, such as benzene or toluene, or mixtures thereof, optionally while cooling, especially after the beginning of the reaction, for example to approximately −30° C., or while heating, for example to the boiling temperature of the reaction mixture, optionally under an inert gas atmosphere, for example a nitrogen atmosphere. A preferred form of the process is the reaction of the aldehyde of the formula III with an excess of the lithium compound of the formula IV.

The hydrolysis of the addition product is effected with solvents that yield H+ ions, for example water (ice-water mixture) or dilute, aqueous acids, for example dilute mineral acids, such as dilute, aqueous sulphuric acid, or dilute organic acids, for example dilute, aqueous acetic acid.

The reaction of a compound of the formula III can also be effected with a compound of the formula IV that has been manufactured in situ and that is obtained, for example, from the corresponding halide, for example chloride, by reaction with a metallating agent, for example magnesium, lithium or tert.-butyllithium.

Process (d) Nucelophilic substitution):

In a starting material of the formula V functional groups are optionally protected by the protecting groups mentioned under process (a).

In a compound of the formula V the nucleofugal leaving group X is especially hydroxy esterified by a strong inorganic or organic acid, such as a mineral acid, for example a hydrohalic acid, such as hydrochloric, hydrobromic or hydriodic acid, or also sulphuric acid or halosulphuric acid, for example fluorosulphuric acid, or hydroxy esterified by a strong organic sulphonic acid, such as a lower alkanesulphonic acid optionally substituted, for example, by halogen, such as fluorine, or an aromatic sulphonic acid, for example a benzenesulphonic acid optionally substituted by lower alkyl, such as methyl, halogen, such as bromine, and/or by nitro, for example a methanesulphonic, trifluoromethanesulphonic or p-toluenesulphonic acid, or hydroxy esterified by hydrazoic acid.

A reagent that introduces the substituent $R_4$ in nucleophilic form is, depending on the meaning of $R_4$, a hydroxide-containing base, for example sodium or potassium hydroxide ($R_4$=OH), an alcohol, for example methanol or ethanol ($R_4$=etherified hydroxy) or the salt of a carboxylic acid, for example silver acetate ($R_4$=esterified hydroxy).

The reaction conditions are preferably so chosen that the reaction proceeds substantially as a second-order nucleophilic substitution ($S_N2$). For example, a compound of the formula V in which X represents a leaving group having high polarisability of the electron shell, for example iodine, can be reacted in a polar aprotic solvent, for example acetone, acetonitrile, nitromethane, dimethyl sulphoxide or dimethylformamide, with the silver salt of a carboxylic acid, for example silver acetate. The reaction with a hydroxide-containing base is preferably carried out in water to which there has optionally been added as solution aid an organic solvent, for example ethanol, tetrahydrofuran or acetone, and the reaction with an alcohol preferably in an excess of that alcohol, optionally in the presence of one of the polar aprotic solvents mentioned above. The substitution reaction is carried out optionally at reduced or elevated temperature, for example within a temperature range of from approximately $-40°$ C. to approximately $+100°$ C., preferably from approximately $-10°$ C. to approximately $+50°$ C., and optionally under an inert gas atmosphere, for example a nitrogen atmosphere.

Process (e) (Conversion of a cyano group into an amide group:

In a starting material or the formula VI functional groups are optionally protected by the protecting groups mentioned under (a).

The conversion of a compound of the formula VI into a compound of the formula I can be effected by a Ritter reaction or by way of carboxylic acid ester imide salts.

In the Ritter reaction, the nitriles are reacted in the presence of a strong acid, for example 85–90% sulphuric acid, or also polyphosphoric acid, hydrofluoric acid, formic acid, boron trifluoride or other Lewis acids but not aluminium chloride, with compounds that are capable of forming carbenium ions in the acidic medium, that is to say, for example, with olefins, such as propylene, or alcohols, such as benzyl alcohol, in most cases without solvent or, for example, in glacial acetic acid.

In a variant of the Ritter reaction, a nitrile of the formula VI is reacted with an olefin and mercury(II) nitrate and the organomercury compound is subsequently reduced with sodium borohydride to an N-substituted compound of the formula I.

By the acid-catalysed, preferably hydrochloric acid-catalysed, addition of alcohols to the nitriles of the formula VI, there are obtained carboxylic acid ester imides which yield amides of the formula I by thermal rearrangement at temperatures above approximately 80° C.

Process (f) (Reduction of the epoxide):

In a starting material of the formula VII functional groups are optionally protected by the protecting groups mentioned under process (a).

It is possible to use those reducing agents which, under the reaction conditions of the process, reduce the epoxy group selectively or more rapidly than the amide groups present and which open the epoxide in such a manner that a sufficient, and as large as possible, proportion of the reaction products carries the newly formed hydroxy group in the position corresponding to that of the formula I. Examples of such selective reducing agents are lithium borohydride or sodium cyanoborohydride/boron trifluoride etherate. Using the last-mentioned reagent the reaction can be carried out, for example, by adding a solution of boron trifluoride etherate, $BF_3.O(C_2H_5)_2$, in tetrahydrofuran to 1 mole of the compound of the formula VII and an excess, for example 1.4–3 moles, of sodium cyanoborohydride in tetrahydrofuran at elevated temperature, for example under reflux, in such a manner that the pH of the solution is maintained close to the turning point of the indicator bromocresol green which has also been added. The reduction with lithium borohydride is preferably carried out in an ether, for example tetrahydrofuran, 1,2-dimethoxyethane or diethylene glycol dimethyl ether, at temperatures of from room temperature to the reflux temperature.

Process (g) (Subsequent operations):

In a resulting compound of the formula I in which $R_1$, A, $R_2$, $R_3$, $R_4$, $R_5$ and $R_6$ have the meanings mentioned, a carboxamide group can be substituted, a carboxy group present in free or reactive form can be esterified, and an esterified carboxy group can be converted into a carboxy group or into a carboxamide group.

Substitution of a carboxamide group or another amino group is effected, for example, by alkylation.

Suitable agents for alkylating a carboxamide group in a compound of the formula I are, for example, diazo compounds, for example diazomethane. Diazomethane can be decomposed in an inert solvent and the free methylene formed in so doing reacts with the carboxamide group in the compound of the formula I. The decomposition of diazomethane is preferably carried out by catalysis, for example in the presence a noble metal in finely divided form, for example copper, or a noble metal salt, for example copper(I) chloride or copper(II) sulphate.

Further alkylating agents are those mentioned in German Offenlegungsschrift 2 331 133, for example alkyl halides, sulpho acid esters, Meerwein salts or 1-substituted 3-aryltriazenes, which can be reacted with a compound of the formula I having a carboxamide group under the reaction conditions mentioned in that specification.

For the esterification of a carboxy group in a compound of the formula I the free acid can be used or the free acid can be converted into one of the reactive derivatives mentioned under process a) and reacted with an alcohol, or the free acid or a reactive salt, for example the caesium salt, ca=be reacted with a reactive derivative of an alcohol. For example, the caesium salt of a carboxylic acid can be reacted with the halide of an alcohol.

The esterification of a carboxy group can be effected with the alkylating agents mentioned above for the substitution of the carboxamide group and under the same reaction conditions, for example with diazomethane, alkyl halides, sulphonic acid esters, Meerwein salts, 1-substituted 3-aryltriazenes, etc.

One of the methods described under process (a), removal of the carboxy-protecting groups, or, if desired, alkaline hydrolysis under the reaction conditions mentioned in "Organikum", 15th edition, VEB Deutscher Verlag der Wissenschaften, Berlin (East) 1976, can be used to convert an esterified carboxy group in a compound of the formula I into a free carboxy group.

In a compound of the formula I an esterified carboxy group can be converted into an optionally substituted carboxamide group by aminolysis with ammonia or a primary or secondary amine. The aminolysis can be effected under the reaction conditions mentioned for such reactions in "Organikum", 15th edition, VEB Deutscher Verlag der Wissenschaften, Berlin (East), 1976.

In a resulting compound of the formula I in which the substituents have the meanings mentioned and at least one free hydroxy group is present and the other functional groups are optionally in protected form, the free hydroxy group, for example the hydroxy group $R_4$, can be etherified or esterified.

The etherification of this hydroxy group can be effected with the alkylating agents mentioned above and under the same reaction conditions, for example with diazomethane, alkyl halides, sulphonic acid esters, Meerwein salts, 1-substituted 3-aryltriazenes, etc..

The esterification of the free hydroxy group can be effected with the customary acylating agents and the customary reaction conditions indicated in "Organikum", for example with acetic anhydride.

The mentioned alkylating reactions, etherifications, esterifications etc. can also be carried out in corresponding manner in a starting material instead of in the end product.

In a resulting compound of the formula I in which one or more functional groups are protected, these groups, for example carboxy, amino, hydroxy and/or mercapto groups, can be freed in a manner known per se, optionally in stages or simultaneously, by means of solvolysis, especially hydrolysis, optionally enzymatic hydrolysis, alcoholysis or acidolysis, or by means of reduction, especially hydrogenolysis, or chemical reduction. The removal of protecting groups is described in the standard works mentioned hereinbefore in the section "protecting groups".

For example, protected carboxy, for example tert.-lower alkoxycarbonyl, lower alkoxycarbonyl substituted in the 2-position by an organic silyl group or in the 1-position by lower alkoxy or lower alkylthio, or optionally substituted diphenylmethoxycarbonyl, can be converted into free carboxy, for example, by treatment with a suitable acid, such as formic acid or trifluoroacetic acid, optionally with the addition of a nucleophilic compound, such as phenol or anisole. Optionally substituted benzyloxycarbonyl can be freed, for example, by means of hydrogenolysis, that is to say by treatment with hydrogen in the presence of a metallic hydrogenation catalyst, such as a palladium catalyst. Suitably substituted benzyloxycarbonyl, such as 4-nitrobenzyloxycarbonyl, can also be converted into free carboxy by reduction, for example by treatment with an alkali metal dithionite, for example sodium dithionite, or with a reducing metal, for example zinc, or a reducing metal salt, such as a chromium(II) salt, for example chromium(II) chloride, customarily in the presence of a hydrogen-yielding agent that together with the metal is capable of producing nascent hydrogen, such as an acid, especially a suitable carboxylic acid, such as an optionally substituted, for example hydroxy-substituted, lower alkanecarboxylic acid, for example acetic acid, formic acid, glycolic acid, diphenylglycolic acid, lactic acid, mandelic acid, 4-chloromandelic acid or tartaric acid, or an alcohol or thiol, with water preferably being added. It is also possible to convert 2-halo-lower alkoxycarbonyl (optionally after converting a 2-bromo-lower alkoxycarbonyl group into a corresponding 2-iodo-lower alkoxycarbonyl group) or aroylmethoxycarbonyl into free carboxy by treatment with a reducing metal or a reducing metal salt, as described above. Aroylmethoxycarbonyl can also be cleaved by treatment with a nucleophilic, preferably salt-forming, reagent, such as sodium thiophenolate or sodium iodide. 2-tri-lower alkylsilyl-lower alkoxycarbonyl can also be converted into free carboxy by treatment with a salt of hydrofluoric acid yielding the fluoride anion, such as an alkali metal fluoride, for example sodium or potassium fluoride, optionally in the presence of a macrocyclic polyether ("Crown ether"), or with a fluoride of an organic quaternary base, such as tetra-lower alkylammonium fluoride or tri-lower alkylarylammonium fluoride, for example tetraetylammonium fluoride or tetrabutylammonium fluoride, in the presence of an aprotic, polar solvent, such as dimethyl sulphoxide or N,N-dimethylacetamide. Carboxy esterified by an organic silyl group, such as tri-lower alkylsilyl, for example trimethylsilyl, can be freed in customary manner by solvolysis, for example by treatment with water, an alcohol or an acid, or also a fluoride, as described above. Esterified carboxy can also be cleaved enzymatically, for example esterified arginine or lysine, such as lysine methyl ester, can be cleaved by means of trypsin.

A protected amino group is freed in a manner known per se and, depending on the nature of the protecting groups, by various methods, but preferably by solvolysis or reduction. 2-halo-lower alkoxycarbonylamino (optionally after converting a 2-bromo-lower alkoxycarbonylamino group into a 2-iodo-lower alkoxycarbonylamino group), aroylmethoxycarbonylamino or 4-nitrobenzyloxycarbonylamino can be cleaved, for example, by treatment with a suitable reducing agent, such as zinc, in the presence of a suitable carboxylic acid, such as aqueous aectic acid. Aroylmethoxycarbonylamino can also be cleaved by treatment with a nucleophilic, preferably salt-forming, reagent, such as sodium thiophenolate, and 4-nitrobenzyloxycarbonylamino also by treatment with an alkali metal dithionite, for example sodium dithionite. Optionally substituted diphenylmethoxycarbonylamino, tert.-lower alkoxycarbonylamino or 2-tri-lower alkylsilyl-lower alkoxycarbonylamino can be freed by treatment with a suitable acid, for example formic acid or trifluoroacetic acid, optionally substituted benzyloxycarbonylamino can be freed, for example, by hydrogenolysis, i.e. by treatment with hydrogen in the presence of a suitable hydrogenation catalyst, such as a palladium catalyst, optionally substituted triarylmethylamino or formylamino can be freed, for example, by treatment with an acid, such as a mineral acid, for example hydrochloric acid, or an organic acid, for example formic acid, acetic acid or trifluoroacetic acid, optionally in the presence of water, and an amino group protected by an organic silyl group can be freed, for example, by hydrolysis or alcoholysis. An amino group protected by 2-haloacetyl, for example 2-chloroacetyl, can be freed by treatment with thiourea in the presence of a base, or with a thiolate salt, such as an alkali metal thiolate, of thiourea and by subsequent solvolysis, such as alcoholysis or hydrolysis, of the resulting condensation product. An amino group protected by 2-tri-lower alkylsilyl-lower alkoxycarbonyl can also be converted into the free amino group by treatment with a salt of hydrofluoric acid yielding fluoride anions, as indicated above in connection with the freeing of a correspondingly protected carboxy group. Silyl, such as trimethylsilyl, that is bonded directly to a hetero atom, such as nitrogen, can also be removed by means of fluoride ions.

Amino protected in the form of an azido group is converted into free amino, for example, by reduction, for example by catalytic hydrogenation with hydrogen in the presence of a hydrogenation catalyst, such as platinum oxide, palladium or Raney nickel, or also by treatment with zinc in the presence of an acid, such as acetic acid. The catalytic hydrogenation is preferably carried out in an inert solvent, such as a halogenated hydrocarbon, for example methylene chloride, or alternatively in water or a mixture of water and an organic solvent, such as an alcohol or dioxan, at approximately from 20° C. to 25° C., or alternatively while cooling or heating.

A hydroxy or mercapto group protected by a suitable acyl group, an organic silyl group or by optionally substituted 1-phenyl-lower alkyl is freed analogously to a correspondingly protected amino group. A hydroxy or mercapto group protected by 2,2-dichloroacetyl is freed, for example, by basic hydrolysis, while a hydroxy or mercapto group protected by tert.-lower alkyl or by a 2-oxa- or 2-thia-aliphatic or -cycloaliphatic hydrocarbon radical is freed by acidolysis, for example by treatment with a mineral acid or a strong carboxylic acid, for example trifluoroacetic acid. Two hydroxy groups that are protected together by means of a preferably substituted methylene group, such as by lower alkylidene, for example isopropylidene, cycloalkylidene, for example cyclohexylidene, or benzylidene, can be freed by acid solvolysis, especially in the presence of a mineral acid or a strong organic acid.

Salts of compounds of the formula I having salt-forming groups can be manufactured in a manner known per se. For example, salts of compounds of the formula I having acidic groups can be formed, for example, by treatment with metal compounds, such as alkali metal salts of suitable organic carboxylic acids, for example the sodium salt of 2-ethylhexanoic acid, or with inorganic alkali metal or alkaline earth metal salts, for example sodium bicarbonate, or with ammonia or a suitable organic amine, preferably stoichiometric amounts or only a small excess of the salt-forming agent being used. Acid addition salts of compounds of the formula I are obtained in customary manner, for example by treatment with an acid or a suitable anion exchange reagent. Internal salts of compounds of the formula I that contain, for example, a free carboxy group and a free amino group can be formed, for example, by neutralising salts, such as acid addition salts, to the isoelectric point, for example with weak bases, or by treatment with ion exchangers.

Salts can be converted in customary manner into the free compounds: metal and ammonium salts, for example, by treatment with suitable acids, and acid addition salts, for example, by treatment with a suitable basic agent.

Stereoisomeric mixtures, especially diastereoisomeric mixtures, can be separated into the individual isomers in a manner known per se, for example by fractional crystallisation, chromatography, etc..

Racemates can be split in a manner known per se, for example after converting the optical antipodes into diastereoisomers, for example by reaction with optically active acids or bases.

At individual chirality centres in a compound of the formula I, for example at the CH-$R_4$ C-atom, the configuration can be deliberately reversed. For example, the configuration at the CH-$R_4$ atom can be reversed by second order nucleophilic substitution according to process (d) after converting the group $R_4$ into a nucleofugal leaving group X and reaction with a reagent that introduces the same substituent $R_4$.

The invention relates also to those forms of the process in which a compound obtainable as intermediate at any stage is used as starting material and the remaining steps are carried out or in which the process is interrupted at any stage or in which a compound obtainable in accordance with the process according to the invention is produced under the process conditions and further processed in situ.

Pharmaceutical Preparations

The pharmacologically acceptable compounds of the present invention can be used, for example, for the manufacture of pharmaceutical preparations that contain an effective amount of the active ingredient together or in admixture with a significant amount of inorganic or organic, solid or liquid, pharmaceutically acceptable carriers.

The pharmaceutical preparations according to the invention are those for enteral, such as nasal, rectal or oral, administration or for parenteral, such as intramuscular or intravenous, administration to warm-blooded animals (humans and animals), which contain an effective dose of the pharmacological active ingredient on its own or together with a significant amount of a pharmaceutically acceptable carrier. The dosage of the active ingredient depends on the species, body weight, age and individual conditon of the warm-blooded animal, on the disease to be treated and also on the mode of administration.

The dosages to be administered to warm-blooded animals, for example humans, of approximately 70 kg body weight are from approximately 3 mg to approximately 3 g, preferably from approximately 10 mg to approximately 1 g, for example approximately 300 mg per person per day, preferably distributed over from 1 to 3 single doses which may, for example, be of equal size. Children usually receive half the adult dose.

The novel pharmaceutical preparations contain from approximately 1% to approximately 95%, preferably from approximately 20% to approximately 90%, active ingredient. Pharmaceutical preparations according to the invention may, for example, be in dosage unit form, such as ampoules, phials, suppositories, dragées, tablets or capsules.

The pharmaceutical preparations of the present invention are produced in a manner known per se, for example by means of conventional dissolving, lyophilising, mixing, granulating or confectioning processes.

There are preferably used solutions of the active ingredient, and also suspensions, especially isotonic aqueous solutions or suspensions, it being possible, for example in the case of lyophilised preparations which contain the active ingredient on its own or together with a carrier, for example mannitol, to prepare these before use. The pharmaceutical preparations may be sterilised and/or contain adjuncts, for example preservatives, stabilisers, wetting agents and/or emulsifiers, solubilisers, salts for regulating the osmotic pressure and/or buffers, and are prepared in a manner known per se, for example by means of conventional dissolving or lyophilising processes. The solutions or suspensions mentioned may contain substances that increase the viscosity, such as sodium carboxymethylcellulose, carboxymethylcellulose, dextran, polyvinylpyrrolidone or gelatine.

Suspensions in oil contain as oily component the vegetable, synthetic or semi-synthetic oils customary for injection purposes. There may be mentioned as such especially liquid fatty acid esters that contain as acid component a long-chained fatty acid having from 8 to 22, especially from 12 to 22, carbon atoms, such as, for example, lauric acid, tridecylic acid, myristic acid, pentadecylic acid, palmitic acid, margaric acid, stearic acid, arachidic acid, behenic acid, or corresponding unsaturated acids, such as, for example, oleic acid, elaidic acid, erucic acid, brassidic acid or linoleic acid. The alcohol component of these fatty acid esters has at most 6 carbon atoms and is a mono- or poly-hydric, for example mono-, di- or tri-hydric, alcohol, for example methanol, ethanol, propanol, butanol or pentanol or their isomers, but above all glycol or glycerine. There may therefore be mentioned by way of example as fatty acid esters: ethyl oleate, isopropyl myristate, isopropyl palmitate, "Labrafil M 2735" (polyoxyethylene glycerine trioleate manufactured by Gattefossé, Paris), "Myglyol 812" (triglyceride of saturated fatty acids of chain length $C_8$ to $C_{12}$, manufactured by Chemische Werke Witten/Ruhr, Germany), but especially vegetable oils, such as cotton seed oil, almond oil, olive oil, castor oil, sesame oil, soya bean oil and, above all, groundnut oil.

The manufacture of the injection preparations is effected in customary manner under sterile conditions, as is the introduction thereof into ampoules or phials and the sealing of the containers.

Pharmaceutical preparations for oral administration can be obtained by combining the active ingredient with solid carriers, optionally granulating a resulting mixture and, if desired or necessary after the addition of suitable adjuncts, processing the mixture or granulate into tablets or dragée cores. They can also be incorporated into plastics carriers which release the active ingredients, or allow them to diffuse, in a controlled manner.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starch pastes using, for example, corn, wheat, rice or potato starch, gelatine, tragacanth, methylcellulose, hydroxypropylmethylcellulose, sodium carboxymethylcellulose and/or polyvinylpyrrolidone, and/or, if desired, disintegrators, such as the above-mentioned starches, also carboxymethyl starch, crosslinked polyvinylpyrrolidone, agar, alginic acid or a salt thereof, such as sodium alginate. Adjuncts are especially flow-regulating agents and lubricants, for example silica, talc, stearic acid or salts thereof, such as magnesium stearate or calcium stearate, and/or polyethylene glycol. Dragée, cores are provided with suitable coatings that may be resistant to gastric juices, there being used, inter alia, concentrated sugar solutions which may contain gum arabic, talc, polyvinylpyrrolidone, polyethylene glycol and/or titanium dioxide, lacquer solutions in suitable organic solvents or solvent mixtures or, for the production of coatings that are resistant to gastric juices, solutions of suitable cellulose preparations, such as ethylcellulose phthalate or hydroxypropylmethylcellulose phthalate. Dyes or pigments can be added to the tablets or dragée coatings, for example for indentification purposes or to indicate different doses of active ingredient.

Starting Materials

The present invention relates also to novel starting materials and/or intermediates and to processes for the manufacture thereof. The starting materials and the reaction conditions are preferably so chosen that the compounds mentioned as being preferred are obtained.

The starting materials for carrying our process (a) can be manufactured according to processes that are known per se, for example from the relevant amino acids by condensation in a manner analogous to that of process (a) described hereinbefore.

For example, a compound of the formula

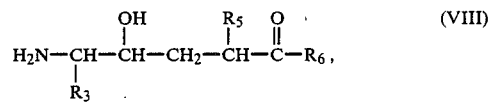

(VIII)

in which $R_3$, $R_5$ and $R_6$ have the meanings mentioned under formula I, can be manufactured by converting a compound of the formula

(IX)

in which $R_3$ has the meaning mentioned and $Z_1$ is an amino-protecting group, with a sulphur-ylide compound into an epoxide of the formula

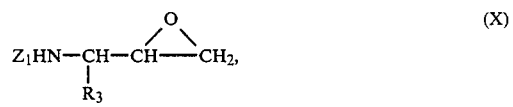

(X)

in which $R_3$ and $Z_1$ have the meanings mentioned, and, optionally after separating the isomers, reacting the resulting compound (X) with a reagent that introduces a nucleofugal leaving group X, and reacting the resulting compound of the formula

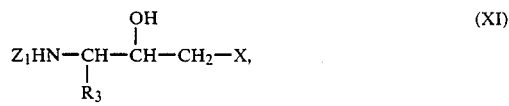

(XI)

in which R₃ and Z₁ have the meanings mentioned and X is a nucleofugal leaving group, with a carbonyl compound of the formula

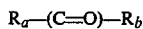  (XII), in which each of the radicals $R_a$ and $R_b$, independently of the other, represents hydrogen, lower alkyl, aryl or aryl-lower alkyl, $R_a$ and $R_b$ together represent optionally bridged alkylidene having from 4 to 12 carbon atoms, or with a reactive derivative of that carbonyl compound, in the presence of an acidic reagent, and reacting the resulting compound of the formula

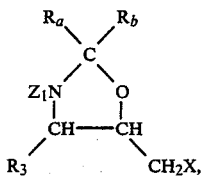  (XIII)

in which the substituents have the meanings mentioned, with a carboxylic acid ester salt of the formula

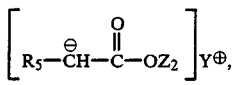  (XIV)

in which $R_5$ has the meaning given under formula I, $Z_2$ is a carboxy-protecting group and $Y^{\oplus}$ is a cation, for example an alkali metal ion, for example the sodium, or preferably the lithium, ion, and, in a resulting compound of the formula

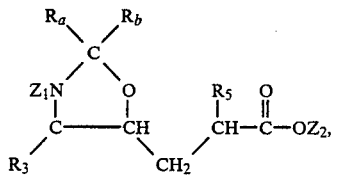  (XV)

in which the substituents have the meanings mentioned, removing the carboxy-protecting group $Z_2$ and/or separating a resulting isometric mixture into the individual isomers, amidating the resulting compound having a free carboxy group ($Z_2$=H) with and amine $R_6$—H, and, in a resulting compound of the formula

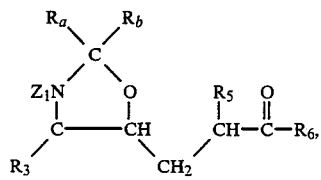  (XVI)

in which the substituents have the meanings mentioned, opening the ring with a suitable solvolysis reagent and optionally removing the protecting group $Z_1$.

The process is carried out analogously to the process described in European Patent Application 143 746.

The entire reaction sequence for the manufacture of the intermediates of the formula VIII can be effected in situ or after isolation of some or all of the preliminary products obtainable in accordance with the process.

Compounds of the formula II are manufactured, for example, by reacting a carboxylic acid of the formula

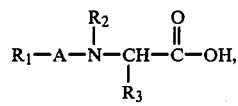  (XVII)

or a suitable functional derivative thereof, in which the substituents have the meanings mentioned and free functional groups, with the exception of the optionally modified carboxy group, are optionally in protected form, with an organometal compound of the formula IV in which $R_5$ and $R_6$ have the meanings mentioned and M represents a metal radical, for example —Li or —MgHal, for example —MgCl, —MgBr or —MgI, and solvolysing the addition product formed.

Suitable functional derivatives of carboxylic acids of the formula XVII are, for example, the corresponding lithium salt of the carboxylic acid, a carboxylic acid halide, for example carboxylic acid chloride, an anhydride, for example the symmetrical carboxylic acid anhydride or a mixed carboxylic acid anhydride with a sterically hindered carboxylic acid, for example with pivalic acid, or a thio ester, for example 2-pyridylthio ester.

The reaction of a carboxylic acid of the formula XVII or a suitable functional derivative thereof with a compound of the formula IV is carried out in the customary manner, for example under the reaction conditions indicated in process (c), but optionally while cooling, for example at temperatures of from approximately −50° C. to approximately 0° C. In a preferred embodiment of the process, a 2-pyridyl-thio ester of the carboxylic acid of the formula XVII is reacted with a bromomagnesium compound of the formula IV.

Compounds of the formula III can be manufactured according to processes that are known per se, for example by, in a compound of the formula XVII in which the subsitutents have the meanings mentioned and free functional groups are optionally in protected form, reducing the carboxy group to the aldehyde function according to methods that are known per se, for example via the corresponding methyl or ethyl ester, via an imidazolide or via an N-methoxy-N-methylamide.

Compounds of the formula IV can be manufactured, for example, by reacting a known halide, or a halide that can be manufactured according to methods known per se, of the formula

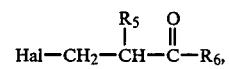  (XVIII)

for example the chloride, with a metallating agent, for example magnesium, lithium or tert.-butyllithium.

Compounds of the formula V are manufactured, for example, by reacting an aldehyde of the formula III with an organometal compound of the formula IV according to process (c) and esterifying the resulting hydroxy compound of the formula I, optionally after separating the isomers, with a strong organic or inorganic acid corresponding to the definition of X, for example as described above for the manufacture of a compound of the formula XI from the corresponding diol.

Nitriles of the formula VI are manufactured, for example, by reacting a compound of the formula

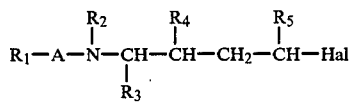  (XIX)

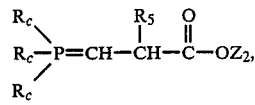  (XX)

in which the substituents have the meanings mentioned, with a salt of hydrocyanic acid.

Suitable salts of hydrocyanic acid should be sufficiently soluble in the chosen inert solvent for a reaction to take place. Such salts are, for example, ammonium cyanide, alkali metal cyanides or alkaline earth metal cyanides, for example sodium or potassium cyanide, or transition metal cyanides, for example copper cyanide. Owing to their lower basicity as compared with the alkali metal cyanides, the transition metal cyanides are especially suitable.

Depending on the nature of the cyanide used and the solvent, an equilibrium is established between the isomeric nitrile form and the isonitrile form. The nitrile form is preferentially formed if, for example, the reaction is effected with those metal cyanides of which the metal cations have a lower atomic weight than that of copper.

Suitable inert solvents are above all polar, aprotic solvents, for example carboxylic acid amides, for example dimethylformamide or dimethylacetamide, nitriles, for example acetonitrile or propionitrile, or di-lower alkyl sulphoxides, for example dimethyl sulphoxide.

The reaction is effected at room temperature, at reduced or at elevated temperature, for example within a temperature range of from approximately −40° C. to approximately +100° C., preferably from approximately −10° C. to approximately +50° C. and, if desired, under an inert gas atmosphere, for example a nitrogen atmosphere.

Epoxides of the formula VII are manufactured, for example, by reacting a compound of the formula IX with a phosphoranylidene compound of the formula in which $R_c$ represents an optionally substituted hydrocarbon radical, $R_5$ has the meanings mentioned and $Z_2$ is a carboxy-protecting group, and converting a resulting compound of the formula

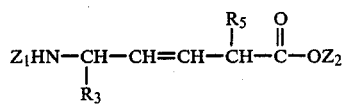  (XXI)

into an epoxide with an oxidising agent containing the peroxo group and, in a resulting compound, removing the protecting groups $Z_1$ and $Z_2$ and replacing them by the groups $R_1S—A—$ and $R_6$ in any desired sequence of the reaction steps.

$R_c$ is preferably phenyl. The reaction of a compound of the formula IX with a phosphoranylidene compound of the formula XX is effected under the reaction conditions known for Wittig reactions and described, for example, in "Organikum". The olefin of the formula XXI which is obtainable in so doing is optionally reacted in situ with the oxidising agent, for example peracetic acid or m-chloroperbenzoic acid. The removal of the protecting groups $Z_1$ and $Z_2$ and the introduction of the groups $R_1$-A- and $R_6$ is described hereinbefore under process (a).

The following Examples serve to illustrate the invention but do not limit the scope thereof in any way.

Temperatures are given in degrees Centigrade. The $R_f$-values are determined on silica gel thin-layer plates in the following solvent systems:

| | | |
|---|---|---|
| N1 | chloroform/methanol | 9:1 |
| N2 | chloroform/methanol | 19:1 |
| N3 | ethyl acetate/n-hexane | 1:1 |
| N4 | ethyl acetate/n-hexane | 1:4 |
| N5 | ethyl acetate/n-hexane | 1:9 |
| N6 | methylene chloride/ether | 4:1 |
| N7 | methylene chloride/ether | 1:1 |
| N8 | methylene chloride/methanol | 9:1 |
| N9 | methylene chloride/methanol | 6:1 |
| N10 | methylene chloride/methanol | 20:1 |
| N11 | methylene chloride/methanol | 10:1 |
| N12 | methylene chloride/methanol | 5:1 |
| N13 | ethyl acetate/n-hexane | 4:1 |
| N14 | ethyl acetate/n-hexane | 2:1 |
| N15 | ethyl acetate/n-hexane | 1:2 |
| N16 | methylene chloride/methanol/water | 300:10:1 |
| N17 | ethyl acetate/n-hexane | 1:6 |
| N18 | ethyl acetate/methanol | 1:1 |
| N19 | ethyl acetate/methanol | 4:1 |
| N20 | methylene chloride/methanol | 3:1 |
| N21 | methylene chloride/methanol | 4:1 |
| N22 | methylene chloride/methanol/water | 40:10:1 |
| B1 | chloroform/methanol/conc. ammonia | 40:10:1 |
| B2 | chloroform/methanol/conc. ammonia | 350:50:1 |
| B3 | methylene chloride/methanol/conc. ammonia | 1000:50:1 |
| B4 | methylene chloride/methanol/conc. ammonia | 350:50:1 |
| B5 | methylene chloride/methanol/conc. ammonia | 140:10:1 |
| B6 | methylene chloride/methanol/conc. ammonia | 105:50:1 |
| B7 | methylene chloride/methanol/conc. ammonia | 90:10:1 |
| B8 | methylene chloride/methanol/conc. ammonia | 80:10:1 |
| B9 | methylene chloride/methanol/conc. ammonia | 65:10:1 |
| B10 | methylene chloride/methanol/conc. ammonia | 50:10:1 |
| B11 | methylene chloride/methanol/conc. ammonia | 40:10:1 |

| | | |
|---|---|---|
| B12 | methylene chloride/methanol/conc. ammonia | 40:25:1 |
| B13 | methylene chloride/methanol/conc. ammonia | 30:10:1 |
| B14 | methylene chloride/methanol/conc. ammonia | 25:10:1 |
| B15 | methylene chloride/methanol/conc. ammonia | 20:5:1 |
| B16 | methylene chloride/methanol/conc. ammonia | 10:10:1 |
| B17 | ethyl acetate/pyridine/glacial acetic acid/water | 62:21:6:11 |
| B18 | n-butanol/pyridine/glacial acetic acid/water | 38:24:8:30 |
| B19 | pyridine/n-butanol/n-amyl alcohol/methyl ethyl ketone/glacial acetic acid/formic acid/water | 25:20:15:10:3:3:25 |
| B20 | n-butanol/pyridine/formic acid/water | 42:24:4:20 |
| B21 | n-butanol/pyridine/glacial acetic acid/water | 42:24:4:30 |
| B22 | n-butanol/pyridine/formic acid/water | 44:24:2:20 |
| B23 | methylene chloride/methanol/conc. ammonia | 700:50:1 |
| B24 | methylene chloride/methanol/conc. ammonia | 60:10:1 |
| B25 | methylene chloride/methanol/conc. ammonia | 370:30:1 |
| B26 | methylene chloride/methanol/conc. ammonia | 300:10:1 |
| B27 | methylene chloride/methanol/conc. ammonia | 70:10:1 |
| B28 | methylene chloride/methanol/conc. ammonia | 800:50:1 |
| B29 | methylene chloride/methanol/conc. ammonia | 500:50:1 |
| B30 | methylene chloride/methanol/conc. ammonia | 750:50:1 |
| B31 | methylene chloride/methanol/conc. ammonia | 200:10:1 |
| B32 | methylene chloride/methanol/conc. ammonia | 5:3:1 |
| B33 | methylene chloride/methanol/conc. ammonia | 100:10:1 |
| S1 | ethyl acetate/pyridine/glacial acetic acid/water | 62:21:6:11 |
| S2 | ethyl acetate/methanol/glacial acetic acid/water | 67:10:12:23 |
| S3 | chloroform/methanol/water/glacial acetic acid | 300:108:20:2 |
| S4 | chloroform/methanol/water/glacial acetic acid | 150:54:10:1 |
| S5 | chloroform/methanol/water/glacial acetic acid | 140:80:20:1 |
| S6 | chloroform/methanol/water/glacial acetic acid | 180:20:2:1 |
| S7 | chloroform/methanol/water/glacial acetic acid | 110:94:26:1 |
| S8 | chloroform/methanol/water/glacial acetic acid | 80:20:3:3 |
| S9 | chloroform/methanol/water/glacial acetic acid | 70:3:3:3 |
| S10 | methylene chloride/methanol/water/glacial acetic acid | 750:270:50:5 |
| S11 | n-butanol/glacial acetic acid/water | 67:10:23 |
| S12 | methylene chloride/methanol/water/glacial acetic acid | 160:30:3:9 |
| S13 | ethyl acetate/n-hexane/glacial acetic acid | 40:60:1 |

For example, the abbreviation "$R_f(N1)$" denotes that the $R_f$ value has been determined in system N1. The ratio of the solvents to one another is given in parts by volume.

The same abbreviations are used for the eluant systems in the flash chromatography and the medium-pressure chromatography.

Abbreviations for amino acids and amino acid derivatives:

| | |
|---|---|
| H—Ala—OH | L-alanine |
| H—Arg—OH | L-arginine |
| H—Cha—OH | L-cyclohexylalanine |
| H—Gln—OH | L-glutamine |
| H—Glu—OH | L-glutamic acid |
| H—Glu(OR)—OH | L-glutamic acid in which the carboxylic acid function of the side chain has been esterified by the radical R |
| H—Gly—OH | glycine |
| H—His—OH | L-histidine |
| H—(N-methyl-His)—OH | Nα-methyl-L-histidine |
| H—Ile—OH | L-isoleucine |
| H—Leu—OH | L-leucine |
| H—Lys—OH | L-lysine |
| H—Lys(R)—OH | L-lysine in which the amino function of the side chain has been substituted by the radical R |
| H—Nle—OH | L-norleucine, (S)-α-aminohexanoic acid |
| H—Orn—OH | L-ornithine, (S)-α,δ-valeric acid |
| H—Orn(R)—OH | L-ornithine in which the amino function of the side chain has been substituted by the radical R |
| H—Phe—OH | L-phenylalanine |
| H—(N-methyl-Phe)—OH | N-methyl-L-phenylalanine |
| H—(p-amino-Phe)—OH | L-p-aminophenylalanine |
| H—Val—OH | L-valine |
| —NH$_2$ instead of —OH: | C-terminal (carboxylic acid) amide |
| —OMe instead of —OH: | C-terminal (carboxylic acid) methyl ester |
| —NHMe instead of —OH: | C-terminal (carboxylic acid) methyl amide |

The fragment referred to as —Leu≃Val— denotes the bivalent radical of (2S,4S,5S)-5-amino-2-isopropyl-4-hydroxy-7-methyloctanoi acid and has the formula

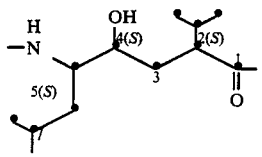

The fragment referred to as —Leu$^{cx}$Val— is derived from the fragment —Leu$^c$Val— by bridging NH and OH by an isopropylidene group and has the formula

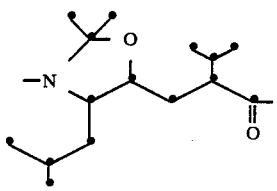

The fragment referred to as —Cha$^c$Val— denotes the bivalent radical of (2S,4S,5S)-5-amino-6-cyclohexyl-2-isopropyl-4-hydroxyhexanoic acid and has the formula

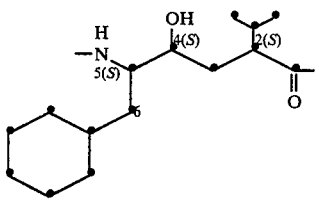

The fragment referred to as —Cha$^{cx}$Val— is derived from the fragment —Cha$^c$Val— by bridging NH and OH by an isopropylidene group.

The fragment referred to as Gly($R_3$)$^c$Gly($R_5$) represents the bivalent radical of 2—$R_5$—4—(S)hydroxy-5-amino-5-$R_3$-pentanoic acid having the (R)- or (S)-configuration at the c-atom 2 or 5 and has the formula

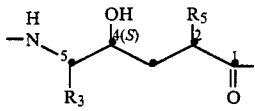

The fragment referred to as —Gly($R_3$)$^{cx}$Gly($R_5$)— is derived from the fragment —Gly($R_3$)$^c$Gly($R_5$)— by bridging NH and OH by an isopropylidene group.

Other Abbreviations

Ac=acetyl
BOC=tert.-butoxycarbonyl
DCCI=dicyclohexyl carbodiimide
DCH=dicyclohexylurea
DMF=dimethylformamide
DMSO=dimethyl sulphoxide
HOBt=1-hydroxybenzotriazole
b.p.=boiling point
m.p.=melting point
THF=tetrahydrofuran
Z=benzyloxycarbonyl Example 1:
N-(Quinolyl-2-carbonyl)-Phe-Leu$^c$Val-NHMe 54 mg of N-(quinolyl-2-carbonyl)-L-phenylalanine, 41 mg of H-Leu$^c$Val-NHMe and 26 mg of HOBt (Fluka purum, contains 11-13% water) are cooled to 0° C. in 2.5 ml of DMF. After the addition of 45 mg of DCCI the whole is stirred for 15 hours while cooling with ice and then for 2 days at room temperature. The crystalline DCH is filtered off with suction and the filtrate is concentrated in a high vacuum. The residue is stirred in a mixture of methanol/water/glacial acetic acid (94:3:3) for 30 minutes at 60° C. and then concentrated. The residue is separated by means of flash chromatography (35 g of silica gel 60, 40-63 um, eluant system N10). The product-containing fractions are concentrated by evaporation. After drying in a high vacuum, the title compound is obtained in the form of a slightly yellowish powder. $R_f$(N10)=0.33; $R_f$(N13)=0.08.

The starting material H-Leu$^c$Val-NHMe may be produced in accordance with the following reaction scheme:

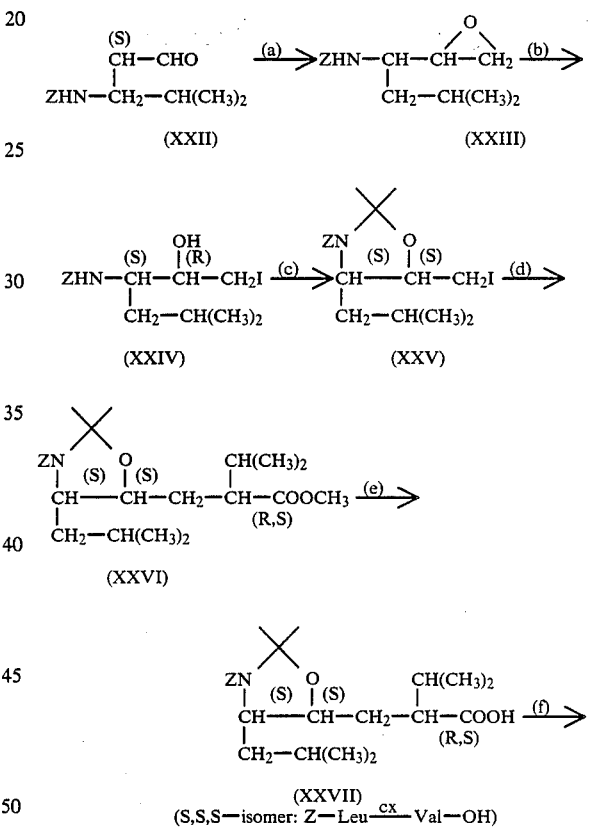

(a) 8.75 g of sodium hydride dispersion (55% in oil) are freed of oil in a dry sulphonating flask under argon by stirring three times in 85 ml of petroleum ether (b.p. 40°-60°) and subsequently decanting off the solvent in each case. After drying in a high vacuum, a grey powder is obtained to which there is added dropwise a solution of 44.1 g of trimethylsulphoxonium iodide in 180 ml of dimethyl sulphoxide, the temperature rising to approximately 40°. The grey suspension is stirred for 1 hour at room temperature and then, over a period of 50 minutes at 10°, a solution of 43.4 g of (S)-2-benzyloxycarbonylamino-4-methylpentanal (XXII) (manufacture: Helvetica Chimica Acta 66, 450 (1983)) in 180 ml of DMSO is added. The yellow suspension is stirred for 15 minutes at 10° and then for 1.5 hours at room temperature. The yellowish turbid solution is poured onto 500 g of ice. The aqueous solution is extracted with ether and the organic phase is washed with water and, after being dried over sodium sulphate, concentrated by evaporation. The oily residue is separated by means of flash chromatography on 2 kg of silica gel (40–63 um) with a mixture of methylene chloride/n-hexane/ethyl acetate (5:10:3). The product-containing fractions are combined, concentrated by evaporation and dried in a high vacuum. The epoxide (XXIII) (diastereoisomeric mixture, approximately 3:1) is obtained in the form of a slightly yellowish oil. $R_f(B1)=0.57$; $R_f(N4)=0.16$.

(b) 33.8 g of compound (XXIII) are taken up in 225 ml of acetonitrile and the resulting solution is cooled to 0°. After the addition of 19.24 g of sodium iodide, 16.27 ml of trimethylchlorosilane are added dropwise at 0° over a period of 30 minutes. The mixture is stirred at from 0° to 3° for 40 minutes and then poured onto 250 ml of ice-cold water. The aqueous mixture is extracted with ether and the organic phase is washed with 10% strength aqueous sodium thiosulphate solution and saturated aqueous sodium chloride solution. After being dried over sodium sulphate and concentrated by evaporation an oily mixture of the desired alcohol (XXIV) and the corresponding trimethylsilyl ether (both diastereoisomeric mixtures) is obtained. The free alcohol is removed by means of flash chromatography (2 kg of silica gel 60, 40–63 um, eluant N4). Concentration by evaporation of the combined product-containing fractions yields the alcohol (XXIV) in the form of an oil. After combining and concentrating by evaporation the fractions that contain the trimethylsilyl ether, the residue is taken up in THF, a solution of 2.67 g of tetrabutylammonium fluoride in water is added and the resulting mixture is stirred for 3 days at room temperature. The solution is then extracted by shaking between water and ether. The organic phase is washed with water, dried over sodium sulphate and concentrated by evaporation. After drying in a high vacuum an additional amount of the diastereoisomeric mixture of compound (XXIV) is obtained in the form of an oil. The total amount of diastereoisomeric mixture (XXIV) is, for the purpose of further purification, separated into two portions by medium-pressure chromatography (1.4 kg of Lichroprep® Si 60, 25–40 um, eluant: ethyl acetate/n-hexane (1:8), fractions of approximately 220 ml). By crystallisation from petroleum ether (b.p. 40°–60°) the more strongly polar component can be concentrated to some extent from the crude material and the mixed fractions (m.p. 104°–106°). The two diastereoisomers are obtained in a ratio of approximately 3:1. The less polar, oily component is the desired compound (XXIV). $R_f(N4)=0.16$; $R_f(B1)=0.54$.

(c) 66.6 g of compound (XXIV) and 1.62 g of p-toluenesulphonic acid monohydrate are heated under reflux for 3 hours in 1500 ml of 2,2-dimethoxypropane. After cooling to room temperature the mixture is extracted by shaking between 1000 ml of ether and 500 ml of saturated, aqueous sodium bicarbonate solution. The organic phase is washed with water, dried over sodium sulphate and concentrated by evaporation. The semi-crystalline crude product is purified by flash chromatography (2 kg of silica gel 60, 40–63 um, eluant N17, fractions of approximately 400 ml). Concentration by evaporation of the combined product-containing fractions yields compound (XXV) in the form of slightly yellowish crystals. $R_f(N4)=0.48$; $R_f(N5)=0.26$.

(d) 10.82 ml of diisopropylamine are dissolved in 100 ml of absolute tetrahydrofuran under argon and cooled to 0°. Subsequently, at from 0°–5°, a 1.6M solution of n-butyllithium in hexane is added dropwise for 20 minutes to the mixture and the whole is stirred for 15 minutes. Then, at from −70° to −75°, 10.1 ml of isovaleric acid methyl ester are added dropwise and the mixture is stirred for 1.5 hours at −75°. At from −60° to −75° 190 ml of hexamethylphosphoric acid triamide are added dropwise while stirring. The resulting suspension is stirred for 10 minutes and eventually, at from −70° to −75°, a solution of 30.0 g of compound (XXV) in 50 ml of tetrahydrofuran is added dropwise over a period of 5 minutes. The reaction mixture is stirred at room temperature for 2.5 hours and eventually poured onto a mixture of 450 ml of saturated aqueous ammonium chloride solution and 500 g of ice. The aqueous phase is extracted with ether and the organic phase is washed with water and dried over sodium sulphate. Concentration by evaporation yields the diastereoisomeric mixture of compound (XXVI) in the form of a yellow oil. $R_f(N5)=0.20$; $R_f(N4)=0.40$ (values for the less polar component).

(e) 1.07 ml of water are added at approximately 5° to 10.7 g of potassium tert.-butoxide in 80 ml of ether. The white suspension is stirred for 10 minutes in an ice bath and then 10.0 g of compound (XXVI) (diastereoisomeric mixture) in 80 ml of ether are added, the temperature being maintained below 10°. The reaction mixture is then stirred for 18 hours at room temperature and eventually poured onto 1600 ml of saturated aqueous ammonium chloride solution. The aqueous phase is extracted with ether and the organic phase is washed with saturated aqueous sodium chloride solution, dried over sodium sulphate and concentrated by evaporation. The oily crude product is separated by medium-pressure chromatography (740 g Lichroprep® Si 60, 25–40 um, eluant ethyl acetate/n-hexane 1 5). Z—Leu$^{cx}$Val—OH, the less polar component of compound (XXVII) with the desired configuration of the carbon atom bonded to the isopropyl group (S-configuration) is obtained in the form of a yellow oil. $R_f$ (methylene chloride/methanol/water 500:10:1)=0.13; $R_f$ (N6)=0.58.

(f) Z—Leu$^{cx}$Val—NHMe: A mixture of 500 mg of Z—Leu$^{cx}$Val—OH, 10 ml of DMF, 245 mg of HOBt and 330 mg of DCCI is left to stand for 24 hours at 0°. Excess methylamine is added to the mixture, which is stirred for 2 hours at 0° and for 2 hours at room temperature. The crystallised DCH is filtered off and the filtrate is concentrated and dried in a high vacuum. The title compound is obtained in the form of a colourless oil by flash chromatography (eluant system N3) of the residue. $R_f$ (methylene chloride/ether 2:1=0.45.

(g) H—Leu$^{cx}$Val—NHMe: 352 mg of Z—Leu$^{cx}$Val—NHMe are hydrogenated in 30 ml of methanol/water 9:1 in the presence of 70 mg of palladium-on-carbon (10% Pd) at normal pressure and room temperature until saturation is reached. The reaction mixture is filtered and the filtrate is stirred with 75 ml of water at room temperature. After evaporating off the solvent the title compound is obtained in the form of a colourless oil. $R_f(B4)=0.08$; $R_f(S4)=0.27$.

(h) N-(Quinolyl-2-carbonyl)-L-phenylalanine: 4.5 ml of 1N sodium hydroxide solution and 0.78 g of quinolyl2-carboxylic acid chloride (quinaldic acid chloride, m.p. 91°–94°, manufactured according to the directions of D. L. Hammick and W. P. Dickinson, J. Chem. Soc. 1929, 214) in 10 ml of methylene chloride are simultaneously added dropwise at 0°, over a period of 10 minutes, to a solution of 0.50 g of L-phenylalanine in 3 ml of 1N sodium hydroxide solution. The mixture is stirred for 30 minutes at room temperature, then 7.5 ml of 1N hydrochloric acid are added and the whole is extracted with ethyl acetate. The extracts are dried over sodium sulphate and concentrated. The title compound crystallises from a methylene chloride/hexane mixture in the form of a slightly pink powder, m.p. 160°–162°. $R_f(B11)=0.25$.

Example 2:
N-(Quinolyl-2-carbonyl)-Phe-Leu$^c$Val-7-tert.-butoxycarbonyl-n-heptylamide The title compound is obtained analogously to Example 1 using as starting materials 96 mg of N-(quinolyl-2-carbonyl)-L-phenylalanine (Example 1h), 128 mg of H-Leu$^c$Val-7-tert -butoxycarbonyl-n-heptylamide in 5 ml of DMF, 46 mg of HOBt and 80 mg of DCCI and carrying out purification by flash chromatography (35 g of silica gel 60, 40–63 um, eluant system N3). $R_f(N10)=0.31$.

The starting materials are manufactured in the following manner:

(a) H-Leu$^c$Val-7-tert.-butoxycarbonyl-heotylamide is obtained by hydrogenating 213 mg of Z-Leu$^{cx}$Val-7-tert.-butoxycarbonyl-heptylamide in the presence of 40 mg of palladium-on-carbon (10%) analogously to Example 1g). $R_f(B2)=0.13$.

(b) Z-Leu$^{cx}$Val-7-tert.-butoxycarbonyl-heptylamide is obtained analogously to Example 1 using as starting materials 162 mg of Z-Leu$^{cx}$Val-OH and 103 mg of 8-aminooctanoic acid tert.-butyl ester and adding 61 mg of HOBt, 53 ul of 4-methylmorpholine and 107 mg of DCCI. $R_f(N4)=0.20$.

(c) 8-Aminooctanoic acid tert.-butyl ester is obtained analogously to Example 1g) in the form of a colourless oil by hydrogenating 1.5 g of benzyloxycarbonylaminooctanoic acid tert.-butyl ester in 15 ml of methanol after the addition of 0.10 g of palladium-on-carbon (10%). $R_f(B3)=0.08$.

(d) 8-Benzyloxycarbonylaminooctanoic acid tert.-butyl ester: In an autoclave, 2 g of 8-benzyloxycarbonylaminooctanoic acid in 12 ml of dioxan are reacted in the presence of 1.2 ml of sulphuric acid with 7.5 g of isobutylene and the whole is left to stand at room temperature for 48 hours. Ice and 40 ml of 1.8N aqueous ammonia solution are added to the reaction mixture. The reaction mixture is extracted with ether. The organic phase is washed with water and saturated aqueous sodium chloride solution, dried over sodium sulphate and concentrated in vacuo. The title compound is obtained in the form of a clear yellow oil. $R_f(N8)=0.44$.

(e) 8-Benzyloxycarbonylaminooctanoic acid: 25 ml of 2N NaOH solution are added to 7 g of 8-aminooctanoic acid. Then, 17.1 g of chloroformic acid benzyl ester (50% in toluene) and 12.5 ml of 4N NaOH solution are simultaneously added at from approximately 0°–5° over a period of 30 minutes. A voluminous white precipitate is observed. 150 ml of ether and 60 ml of water are added to the reaction mixture. The aqueous phase is extracted with ether, ice is added and, while stirring, the pH is slowly adjusted to 2 with dilute aqueous HCl solution. The resulting suspension is extracted twice with ethyl acetate. The organic phases are combined, washed with water and saturated aqueous sodium chloride solution, dried over sodium sulphate and concentrated by evaporation in vacuo. The title compound having a melting point of 63°–64° is obtained, $R_f(N1)=0.53$.

Example 3:
N-Quinolyl-2-carbonyl)-Phe-Leu$^c$Val-7-carboxy-n-heptylamide 124 mg of N-(quinolyl-2-carbonyl)-Phe-Leu$^c$Val-7-tert.-butoxycarbonyl-n-heptylamide (Example 2) and 2.5 ml of trifluoroacetic acid are stirred at room temperature for 10 minutes. The solution is concentrated and the residue is purified by flash chromatography (35 g of silica gel 60, 40–63 um, eluant system B11). The product-containing fractions are concentrated by evaporation. After drying in a high vacuum at 40°, the title compound is obtained in the form of an amorphous powder. $R_f(B11)=0.30$.

Example 4:
N-(Indolyl-2-carbonyl)-Nle-Leu$^c$Val-n-butylamide 56 mg of indole-2-carboxylic acid, 140 mg of H-Nle-Leu$^c$Val-n-butylamide and 54 mg of HOBt (Fluka purum, contains 11–13% water) are cooled to 0° C. in 4 ml of DMF. After the addition of 95 mg of DCCI the whole is stirred for 24 hours while cooling with ice and then for 2 days at room temperature. The crystalline DCH is filtered off with suction and the filtrate is concentrated in a high vacuum. The residue is stirred in 4 ml of a mixture of methanol/water/glacial acetic acid (94:3:3) for 30 minutes at 60° C. and then concentrated. The residue is separated by means of flash chromatography (100 g of silica gel 60, 40–63 um, eluant system N10). The product-containing fractions are concentrated by evaporation. The title compound is obtained in the form of a white powder from the residue by crystallisation from acetonitrile. M.p. 243°–244° C.; $R_f(N14)=0.17$.

The starting material is manufactured in the following manner:

(a) H-Nle-Leu$^c$Val-n-butylamide: 188 mg of Z-Nle-Leu$^c$Val-n-butylamide are hydrogenated in 10 ml of methanol/water 9:1 in the presence of 30 mg of palladium-on-carbon (10% Pd) at normal pressure and room temperature until saturation is reached. The reaction mixture is filtered. After evaporating off the solvent, the residue is dried in a high vacuum and the title compound is obtained in the form of a colourless oil. $R_f(B4)=0.41$.

(b) Z-Nle-Leu$^c$Val-n-butylamide: The title compound is obtained analogously to Example 1 using as starting materials 138 mg of Z-Nle-OH, 150 mg of H-Leu$^c$Val-n-butylamide in 6 ml of DMF, 80 mg of HOBt and 140 mg of DCCI and carrying out purification by flash chromatography (100 g of silica gel 60, 40–63 um, eluant N3). $R_f(N3)=0.15$.

(c) H-Leu$^c$Val-n-butylamide: 595 mg of Z-Leu$^{cx}$Val-n-butylamide are hydrogenated in 40 ml of methanol/water 9:1 in the presence of 100 mg of palladium-on-carbon (10% Pd) at normal pressure and room temperature until saturation is reached. The reaction mixture is filtered and the filtrate is stirred at room temperature for 75 minutes with 40 ml of water. After evaporating off the solvent the title compound is obtained in the form of a slightly yellowish oil. $R_f(B11)=0.57$; $R_f(S4)=0.42$.

(d) Z-Leu$^c$Val-n-butylamide: A mixture of 122 mg of Z-Leu$^{cx}$Val-OH (Example 1e), 2 ml of DMF, 60 mg of HOBt and 80 mg of DCCI is left to stand at 0° C. for 3 days. 120 ml of n-butylamine are added to the mixture while stirring, and the whole is stirred for 2 hours while cooling with ice and for 24 hours at room temperature. The crystalline DCH is filtered off with suction and the filtrate is concentrated in a high vacuum. The title compound is obtained in the form of a slightly yellowish oil by flash chromatography of the residue (30 g of silica gel 60, 40–63 um, eluant N4). $R_f(N3)=0.52$.

Example 5

The following are produced analogously to Example 4:

(a) N-(Indolyl-2-carbonyl)-Nle-Leu$^c$Val-NHMe, flash chromatography with eluant N10; $R_f(B4)=0.61$; $R_f(N8)=0.46$.

(b) N-(Indolyl)-2-carbonyl)-Nle-Leu$^c$Val-isopropylamide, flash chromatography with eluant N14; $R_f(N14)=0.11$; m.p. 241°–243°.

(c) N-(Indolyl-2-carbonyl)-Nle-Leu$^c$Val-n-propylamide, flash chromatography with eluant N14; $R_f(N14)=0.14$; m.p. 220°–224°.

(d) N-(Indolyl-2-carbonyl)-Nle-Leu$^c$Val-2-hydroxyethylamide, flash chromatography with eluant N10; $R_f(B4)=0.55$; m.p. 241°–242°.

(e) N-(Indolyl-2-carbonyl)-Nle-Leu$^c$Val-benzylamide, flash chromatography with eluant N3; $R_f(N10)=0.35$; m.p. 231°–234°.

(f) N-(Indolyl-2-carbonyl)-Nle-Leu$^c$Val-2-pyridylmethylamide, $R_f(B5)=0.23$; $R_f(B7)=0.46$.

(g) N-(Indolyl-2-carbonyl)-Nle-Leu$^c$Val-1-hydroxy-2(S)-butylamide; $R_f(B23)=0.243$.

(h) N-(Indolyl-2-carbonyl)-Nle-Leu$^c$Val-ethylamide, flash chromatography with eluant N14; $R_f(N14)=0.08$; m.p. 236°–238°.

(i) N-(Indolyl-2-carbonyl)-Nle-Leu$^c$Val-2-(tert.-butoxycarbonylamino)-ethylamide, flash chromatography with eluant N10; $R_f(N10)=0.20$; m.p. 225°–226°.

Example 6:
N-(Indolyl-2-carbonyl)-Nle-Leu$^c$Val-2-aminoethylamide 30 mg of N-(indolyl-2-carbonyl)-Nle-Leu$^c$Val-tert.-butoxycarbonylaminoethylamide (Example 5i) and 3 ml of trifluoroacetic acid are stirred at room temperature for 20 minutes. The reaction solution is concentrated and the residue is separated by flash chromatography (35 g of silica gel 60, 40–63 um, eluant system B8). The product-containing fractions are concentrated by evaporation. The title compound is obtained in the form of a white lyophilisate by lyophilising the residue in 5 ml of tert.-butanol. $R_f(B11)=0.47$.

Example 7:
N-(Indolyl-2-carbonyl)-Phe-Leu$^c$Val-2-(3-carbamoyl-4-hydroxyphenoxy)-ethylamide 25 mg of 2-indolecarboxylic acid, 71 mg of H-Phe-Leu$^c$Val-2-(3-carbamoyl-4-hydroxyphenoxy)ethylamide, 23 mg of HOBt and 40 mg of DCCI are reacted analogously to Example 1. After chromatography in system B7 the title compound is obtained in the form of a yellowish powder. $R_f(B7)=0.27$; $R_f(B9)=0.46$.

The starting materials are manufactured in the following manner:

(a) H-Phe-Leu$^c$Val-2-(3-carbamoyl-4-hydroxyphenoxy)ethylamide is obtained by hydrogenating 236 mg of Z-Phe-Leu$^c$Val-2-(3-carbamoyl-4-hydroxyphenoxy)-ethylamide in the presence of 40 mg of palladium-on-carbon (10%) analogously to Example 1g). $R_f(N11)=0.23$.

(b) Z-Phe-Leu$^c$Val-2-(3-carbamoyl-4-hydroxyphenoxy)-ethylamide is obtained analogously to Example 1 using as starting materials 113 mg of Z-L-phenylalanine, 140 mg of H-Leu$^c$Val-2-(3-carbamoyl-4-hydroxyphenoxy)ethylamide and 58 mg of HOBt and adding 99 mg of DCCI. The product is purified by flash chromatography in system N11. $R_f(N11)=0.39$.

(c) H-Leu$^c$Val-2-(3-carbamoyl-4-hydroxyphenoxy)-ethylamide is obtained, analogously to Example 1g), by hydrogenating 240 ml of Z-Leu$^{cx}$Val-2-(3-carbamoyl-4-hydroxyphenoxy)-ethylamide in the presence of 40 mg of palladium-on-carbon (10%). Purification by flash chromatography in system B11. $R_f B(11)=0.40$; $R_f(B7)=0.15$.

(d) Z-Leu$^{cx}$Val-2-(3-carbamoyl-4-hydroxyphenoxy)-ethylamide is obtained analogously to Example 1 using as starting materials 147 mg of Z-Leu$^{cx}$Val-OH (Example 1e), 107 mg of 2-(3-carbamoyl-4-hydroxyphenoxy)-ethylamine [J. Med. Chem. 27, 831 (1984)] and 61 mg of HOBt and adding 97 mg of DCCI. The product is purified by flash chromatography in system N11. $R_f(N11)=0.38$; $R_f(B7)=0.46$.

Example 8:
N-(Indolyl-2-carbonyl)-His-Leu$^c$Val-n-butylamide 29 mg of indole-2-carboxylic acid, 75 mg of H-His-Leu$^c$Val-n-butylamide and 27 mg of HOBt (Fluka purum, contains 11–13% water) are cooled to 0° C. in 2 ml of DMF. After the addition of 48 mg of DCCI, the whole is stirred for 24 hours while cooling with ice and then for 2 days at room temperature. The crystalline DCH is filtered off with suction and the filtrate is concentrated in a high vacuum. The residue is stirred for 60 minutes at 60° C. in 2 ml of a mixture of methanol/water/glacial acctic acid (94:3:3) and then concentrated. The residue is separated by flash chromatography (100 g of silica gel 60, 40–63 um, eluant system B23). The product-containing fractions are concentrated by evaporation. The title compound is obtained in the form of a white lyophilisate by lyophilising the residue in 6 ml of tert.-butanol. $R_f(B4)=0.40$.

The starting material is manufactured in the following manner:

(a) H-His-Leu$^c$Val-n-butylamide: 98 mg of Z-His-Leu$^c$Val-n-butylamide are hydrogenated in 10 ml of methanol/water 9:1 in the presence of 20 mg of palladium-on-carbon (10% Pd) at normal pressure and room temperature until saturation is reached. The reaction mixture is filtered. After evaporating off the solvent, the residue is dried in a high vacuum and the title compound is obtained in the form of a slightly yellowish oil. $R_f(B11)=0.39$.

(b) Z-His-Leu$^c$Val-n-butylamide: The title compound is obtained analogously to Example 1 using as starting materials 72 mg of Z-His-OH, 72 mg of H-Leu$^c$Val-n-butylamide (Example 4c) in 3 ml of DMF, 38 mg of HOBt and 68 mg of DCCI and carrying out purification by flash chromatography (100 g of silica gel 60, 40–63 um, eluant B23). $R_f(B4)=0.46$.

Example 9

The following are manufactured analogously to Example 8:

(a) N-(Indolyl-2-carbonyl)-His-Leu$^c$Val-NHMe, flash chromatography with eluant B8; $R_f$(S4)=0.60; $R_f$(B4)=0.27.

(b) N-(Indolyl-2-carbonyl)-His-Leu$^c$Val-benzylamide, flash chromatography with eluant B23; $R_f$(B4)=0.36.

(c) N-(Indolyl-2-carbonyl)-His-Leu$^c$Val-isoamylamide, flash chromatography with eluant B23; $R_f$(B4)=0.48.

(d) N-(Indolyl-2-carbonyl)-His-Leu$^c$Val-cyclopropylmethylamide, flash chromatography with eluant B23; $R_f$(B4)=0.39.

Example 10:
N-(N-Benzylindolyl-2-carbonyl)-His-Leu$^c$Val-NHMe 29 mg of N-benzylindole-2-carboxylic acid, 40 mg of H-His-Leu$^c$Val-NHMe, 18 mg of HOBt and 28 mg of DCCI are stirred at room temperature for 1.5 days in 1.5 ml of DMF. After evaporating off the solvent in a high vacuum, the residue is stirred for 1 hour at 60° in 4 ml of a mixture of methanol/water/glacial acetic acid (94:3:3). After concentration to dryness by evaporation, the product is obtained in the form of a colourless amorphous powder by medium-pressure chromatography (Lobar ® prefabricated column size B, 40–60 um particle size, Merck No. 10401, eluant B8). $R_f$(B24)=0.4.

The starting materials are manufactured in the following manner:

(a) N-Benzylindole-2-carboxylic acid is obtained by treating 300 mg of the corresponding ethyl ester (for manufacture see Synthesis 1984, 738) with 2 ml of 1N NaOH in 2 ml of THF at room temperature for 2 days. After the addition of 2 ml of 1N HCl, the whole is concentrated to dryness by evaporation, extracted by shaking between ether and water, the organic phase is dried, and the crude product obtained by concentration by evaporation is separated by medium-pressure chromatography (Lobar ® column Merck No. 10401, eluant ethyl acetate/n-hexane 1:19). $R_f$(N4)=0.03; $^1$H-NMR (TMS, DMSO-d$_6$): 11 ppm (1H), 7.7 (d, 1H), 7.54 (d, 1H), 7.34–7.0 (8H), 5.9 (s, 2H).

(b) H-His-Leu$^c$Val-NHMe is obtained by hydrogenating 410 mg of Z-His-Leu$^c$Val-NHMe in the presence of 50 mg of palladium-on-carbon (10%) in 20 ml of methanol/water (95:5) under normal pressure and CO$_2$ absorption for 4 hours at room temperature. After filtering off the catalyst and concentration to dryness by evaporation, the product is obtained in the form of an amorphous powder by lyophilisation from tert.-butanol. $R_f$(B24)=0.09.

(c) Z-His-Leu$^c$Val-NHMe: 274 mg of DCCI are added at ice bath temperature to 326 mg of Z-His-OH, 250 mg of H-Leu$^c$Val-NHMe and 172 mg of HOBt in 7 ml of DMF. The whole is stirred overnight at 0° and then for 24 hours at room temperature. After evaporating off the solvent, the residue is stirred at 60° for 1 hour in 5 ml of a mixture of methanol/water/glacial acetic acid (94:3:3). The solvent mixture is evaporated off in vacuo and the product is obtained in the form of an amorphous powder by medium-pressure chromatography (1 Lobar ® column size B, Merck No. 10401, eluant B7). $R_f$(B8)=0.35.

Example 11

The following are manufactured analogously to Example 10:

(a) N-(2-[N-Benzyl-o,o'-dichloroanilino]-phenylacetyl)-His-Leu$^c$Val-NHMe, $R_f$(N8)=0.35.

(b) N-(Quinolyl-2-carbonyl)-His-Leu$^c$Val-NHMe, flash chromatography with eluant B4; $R_f$(B4)=0.31.

(c) N-Oxamoyl-His-Leu$^c$Val-NHMe, flash chromatography with eluant B4; $R_f$(B4)=0.28; $R_f$(S8)=0.27.

Example 12:
N-(3-(R,S)-Benzyloxycarbonyl-4-α-naphthylbutyryl)-His-Leu$^c$Val-NHMe Using as starting materials 40.2 mg of 2(R,S)-(α-naphthylmethyl)-succinic acid 1-benzyl ester and 44 mg of H-His-Leu$^c$Val-NHMe, the title compound is obtained analogously to Example 10 in the form of a white solid substance after flash chromatography (100 g of silica gel 60, 40–63 um, eluant system B25). $R_f$(B4)=0.30; $R_f$(S12)=0.40.

The starting material is manufactured in the following manner:

(a) 2(R,S)-(α-Naphthylmethyl)-succinic acid 1-benzyl ester: A solution of 480.5 mg of α-naphthylmethylsuccinic acid anhydride (for manufacture see J. Chem. Soc. 1956, 355–358) and 216.3 mg of benzyl alcohol in 5 ml of toluene is boiled for 6½ hours and then concentrated by evaporation. The residue is dissolved in 10 ml of diisopropyl ether, 362 mg of dicyclohexylamine are added and the whole is stirred overnight. The white crystals of the dicyclohexylammonium salt which have formed are filtered off and recrystallised from diisopropyl ether, m.p. 120°–122°. The mother liquor is used for the manufacture of the isomeric 4-benzyl ester (Example 13a). The recrystallised dicyclohexylammonium salt is dissolved in 10 ml of THF, acidified with 0.5 ml of 1N HCl, filtered and the filtrate is concentrated by evaporation, then dissolved in 20 ml of toluene, filtered and concentrated by evaporation again. Crystallisation of the residue from cyclohexanone yields the title compound in the form of white needles, m.p. 122°–124°; $R_f$(S13)=0.30.

Example 13:
N-(3-Benzyloxycarbonyl-2(R,S)-α-naphthylmethylpropionyl)-His-Leu$^c$Val-NHMe Using as starting materials 36 mg of 2(R,S)-(α-naphthylmethyl)-succinic acid 4-benzyl ester and 38.5 mg of H-His-Leu$^c$Val-NHMe, the title compound is obtained analogously to Example 10 in the form of a white solid substance after flash chromatography in system B25. $R_f$(B4)=0.40; $R_f$(S12)=0.51.

The starting material is manufactured in the following manner:

(a) 2(R,S)-(α-Naphthylmethyl)-succinic acid 4-benzyl ester: The mother liquor of the dicyclohexylammonium salt of example 12a) is concentrated by evaporation, dissolved in 10 ml of THF, acidified with 1.5 ml of 1N HCl, filtered and the filtrate is concentrated by evaporation. The residue is dissolved in ether, washed with 1N HCl and brine, dried over Na$_2$SO$_4$ and concentrated by evaporation, yielding the title compound in the form of a colourless oil. $R_f$(S13)=0.30.

Example 14:
N-(Indolyl-2-carbonyl)-Leu-Leu≗Val-NHMe 39 mg of indole-2-carboxylic acid, 78 mg of H-Leu-Leu≗Val-NHMe, 37 mg of HOBt and 59 mg of DCCI are stirred at room temperature for 2 days in 1.5 ml of DMF. After evaporating off the solvent in a high vacuum, the product is obtained in the form of an amorphous powder by medium-pressure chromatography (Lobar® column size B, Merck No. 10401, eluant B26). $R_f$(B24)=0.53.

The starting material is manufactured in the following manner:

(a) H-Leu-Leu≗al-NHMe is obtained by hydrogenating 115 mg of Z-Leu-Leu≗Val-NHMe in 10 ml of methanol/water (95:5) in the presence of 40 mg of palladium-on-carbon (10%) under normal pressure and $CO_2$ absorption for 5 hours at room temperature. After filtering off the catalyst and concentration to dryness by evaporation, the product is obtained in the form of an amorphous powder. $R_f$(B11)=0.8.

(b) Z-Leu-Leu≗Val-NHMe: 82 mg of DCCI are added to 151 mg of Z-Leu-OH (dicyclohexylammonium salt), 75 mg of H-Leu≗Val-NHMe and 52 mg of HOBt in 3 ml of DMF at ice bath temperature. The whole is stirred for 8 hours in an ice bath and for 10 hours at room temperature. After evaporating off the solvent in a high vacuum, the product is obtained in the form of an amorphous powder by medium-pressure chromatography (Lobar® column, Merck No. 10401, eluant B8). $R_f$(B27)=0.38.

Example 15

The following are manufactured analogously to Example 14:

(a) N-(Indolyl-2-carbonyl)-Cha-Leu≗Val-NHMe, $R_f$(B24)=0.56.

(b) N-(Indolyl-2-carbonyl)-Gln-Leu≗Val-NHMe, $R_f$(B9)=0.23.

(c) N-(N-[Indolyl-2-carbonyl]-L-threo-$\beta$-phenylseryl)-Leu≗Val-NHMe, $R_f$(B8)=0.47.

Example 16:
N-(Indolyl-2-carbonyl)-His-Cha≗Val-NHMe

A mixture of 98.6 mg of H-His-Cha≗Val-NHMe, 37.7 mg of indole-2-carboxylic acid, 35.8 mg of HOBt, 63.9 mg of DCCI and 5.2 ml of DMF is stirred at room temperature for 50 hours. The crystallised DCH is filtered off and the filtrate is concentrated by evaporation. The crude product is purified by flash chromatography (110 g of silica gel 60, 40-63 um, eluant B4). The title compound is obtained by concentrating by evaporation the combined product-containing fractions; $R_f$(B4)=0.22.

The starting material is manufactured in the following manner:

(a) H-His-Cha≗Val-NHMe: 130 mg of Z-His-Cha≗Val-NHMe are hydrogenated in 5 ml of methanol/water 9:1 in the presence of 20 mg of palladium-on-carbon (10% Pd) at normal pressure and room temperature until saturation is reached. The reaction mixture is filtered and the filtrate is stirred with 5 ml of water at room temperature. After evaporating off the solvent, the title compound is obtained in the form of a colourless oil. $R_f$(B11)=0.38.

(b) Z-His-Cha≗Val-NHMe: A mixture of 150.8 mg of H-Cha≗Val-NHMe, 6 ml of DMF, 81.1 mg of HOBt, 153.3 mg of Z-His-OH and 144.2 mg of DCCI is stirred at room temperature for 48 hours. The DCH is filtered off and the filtrate is concentrated and dried in a high vacuum. The residue is separated by flash chromatography (145 g of silica gel 60, 40-63 um, eluant: B23). The title compound is obtained by concentrating by evaporation the combined productcontaining fractions. $R_f$(B4)=0.35; $R_f$(S4)=0.65.

H-Cha≗Val-NHMe is manufactured analogously to the scheme shown in Example 1 as follows:

(c) 2(S)-Benzyloxycarbonylamino-3-cyclohexylpropionic acid ethyl ester: 243 g of 2(S)-benzyloxycarbonylamino-3-cyclohexylpropionic acid (for manufacture see Helvetica Chimica Acta 57, 2131 (1974)) are placed in 600 ml of toluene and 900 ml of ethanol. The reaction is cooled to 0° and 88.3 g of thionyl chloride are added dropwise within a period of 30 minutes. Cooling is discontinued and the reaction mixture is stirred for 18 hours. The reaction mixture is filtered and the filtrate is concentrated. The residue is separated by flash chromatography (2 kg of silica gel 60, 40-63 um, eluant N5). The product-containing fractions are combined, concentrated by evaporation and dried in a high vacuum. The title compound is obtained in the form of a slightly yellowish oil. $R_f$(N5)=0.2; $R_f$(N15)=0.52.

(d) 2(S)-Benzyloxycarbonylamino-3-cyclohexylpropanal: 116.1 g of 2(S)-benzyloxycarbonylamino-3-cyclohexylpropionic acid ethyl ester are placed in 2.2 l of toluene and the whole is cooled to −65°. 836 ml of diisobutylaluminium hydride are added dropwise at −65° within a period of 30 minutes and the mixture is then stirred for 20 minutes. Subsequently 84.2 ml of methanol are added dropwise at −65° within a period of 10 minutes, followed by 825 ml of aqueous potassium-sodium tartrate solution without cooling. The reaction mixture is poured onto 3 of potassium-sodium tartrate solution/ice and extracted with 5 of ether. The ethereal phase is washed with 2 of water, then immediately poured into a solution consisting of 106 g of semicarbazide-hydrochloride and 156.5 g of sodium acetate in 620 ml of water and 620 ml of ethanol. The reaction mixture is subsequently stirred for 1 hour at room temperature, then separated in a separating funnel, and the aqueous phase is extracted twice with 1.5 of ether each time. The organic phase is dried over magnesium sulphate and concentrated by evaporation. The crude product is purified by flash chromatography (2 kg of silica gel 60, 40-63 um, eluant N3). Concentration by evaporation of the combined product-containing fractions yields the semicarbazone of the title compound, $R_f$(N8)=0.51. 130 g of this semicarbazone are dissolved in 1 of THF, and 282 ml of 37% formaldehyde solution and then, at 10°, 143 ml of 0.5N HCl are added. The reaction mixture is stirred for 2 hours at room temperature, filtered and the filtrate is washed with 0.5 of water, 0.5 of $NaHCO_3$ and 0.5 of water. The aqueous phases are extracted with 600 ml of ether. The ethereal phases are dried over magnesium sulphate and concentrated by evaporation. 100 ml of toluene are added to the residue and the whole is concentrated by evaporation, yielding the title compound. This is immediately further processed.

(e) (1(S)-Benzyloxycarbonylamino-2-cyclohexylethyl)-oxirane: 18.9 g of sodium hydride dispersion (55% in oil) are freed of oil in a dry sulphonating flask under argon by stirring three times in 50 ml of petroleum ether (b.p. 40°-60°) and subsequently decanting off the solvent in each case. After drying in a high vacuum, a grey powder is obtained which is introduced into 500 ml of THF and to which 55.6 g of trimethylsulphoxonium iodide are added, the temperature rising to approximately 40°. The grey suspension is boiled under reflux for 1 hour and then, within a period of 50 minutes at −70°, a solution of 108.6 g of 2(S)-benzyloxycarbonylamino-3-cyclohexylpropanal in 250 ml of THF are added. The yellow suspension is stirred for 2 hours at 0°. The yellowish-turbid solution is poured onto 500 g of ice. The aqueous solution is extracted with 2.5 of ether, the organic phase is washed with water and, after drying over sodium sulphate, concentrated by evaporation. The oily residue is separated by flash chromatography (2.5 kg of silica gel 60, 40–63 um, eluant N4). The product-containing fractions are combined, concentrated by evaporation and dried in a high vacuum. The title compound (diastereoisomeric mixture, approximately 4:1) is obtained in the form of a slightly yellowish oil. $R_f$(N16)=0.71; $R_f$(N4)=0.16.

(f) 3(S)-Benzyloxycarbonylamino-4-cyclohexyl-1-iodobutan-2(R,S)-ol: 42.3 g of (1(S)-benzyloxycarbonylamino-2-cyclohexylethyl)-oxirane are taken up in 200 ml of acetonitrile and the resulting solution is cooled to 0°. After the addition of 20.9 g of sodium iodide, 17.7 ml of trimethylchlorosilane are added dropwise at 0° over a period of 30 minutes. The mixture is stirred for 40 minutes at 0°–3° and then poured onto 700 ml of ice-cold water. The aqueous mixture is extracted with ether and the organic phase is washed with 750 ml of 5% strength aqueous sodium thiosulphate solution and 750 ml of saturated aqueous sodium chloride solution. After drying over sodium sulphate and concentration by evaporation, an oily mixture of the title compound is obtained, which is directly further processed.

(g) 3-Benzyloxycarbonyl-4(S)-cyclohexylmethyl-2,2-dimethyl-5(R)-iodomethyl-1,3-oxazolidine: 49.3 g of the compound of Example 16f) and 1.07 g of p-toluenesulphonic acid monohydrate are stirred at room temperature for 3 hours in 140 ml of 2,2-dimethoxypropane and 450 ml of methylene chloride. The mixture is extracted by shaking between 1 of methylene chloride and 500 ml of saturated aqueous sodium bicarbonate solution. The organic phase is washed with water, dried over sodium sulphate and concentrated by evaporation. The crude product is purified by flash chromatography (3 kg of silica gel 60, 40–63 um, eluant N17). The title compound is obtained in the form of a slightly yellowish oil by concentrating by evaporation the combined product-containing fractions. $R_f$(N4)=0.55; $R_f$(N17)=0.46.

(h) 2(R,S)-(3-Benzyloxycarbonyl-4(S)-cyclohexylmethyl-2,2-dimethyl-1,3-oxazolidinyl-5(S)-methyl)-3-methylbutyric acid methyl ester: 14.3 ml of diisopropylamine are dissolved in 200 ml of absolute tetrahydrofuran under argon and cooled to 0°. Then, at 0°–5°, 65.8 ml of a 1.6M solution of n-butyllithium in hexane are added dropwise to the mixture over a period of 20 minutes and stirring is carried out for 20 minutes. Then, at from −70° to 31 75°, 13.3 ml of isovaleric acid methyl ester are added dropwise and the mixture is stirred for 1.5 hours at −75°. At from −60° to −75°, 320 ml of hexamethylphosphoric acid triamide are added dropwise while stirring. The resulting suspension is stirred for 10 minutes and finally, at from −70° to −75°, a solution of 43.4 g of the compound of Example 16g) in 110 ml of tetrahydrofuran is added dropwise within a period of 5 minutes. The reaction mixture is stirred at room temperature for 2.5 hours and eventually poured onto a mixture of 1 l of saturated, aqueous ammonium chloride solution and 500 g of ice. The aqueous phase is extracted with 2 l of ethyl acetate, and the organic phase is washed with water and dried over sodium sulphate. Concentration by evaporation yields the diastereoisomeric mixture of the title compound in the form of a yellow oil $R_f$(N4)=0.36; $R_f$(N5)=0.21 (values for the less polar component).

(i) 2(R,S)-(3-Benzyloxycarbonyl-4(S)-cyclohexylmethyl-2,2-dimethyl-1,3-oxazolidinyl-5(S)-methyl)-3-methylbutyric acid: 1.77 ml of water are added at approximately 5° to 16.5 g of potassium tert.-butoxide in 250 ml of ether. The white suspension is stirred for 10 minutes in an ice bath and then 35.8 g of the compound of Example 16h) (diastereoisomeric mixture) in 250 ml of ether are added, the temperature being maintained below 10°. The reaction mixture is subsequently stirred for 18 hours at room temperature and eventually poured onto 500 ml of saturated aqueous ammonium chloride solution. The aqueous phase is extracted with ethyl acetate and the organic phase is washed with saturated aqueous sodium chloride solution, dried over sodium sulphate and concentrated by evaporation. The oily crude product is separated by flash chromatography (2.5 kg of silica gel 60, 40–63 um, eluant N4). Z-Cha≃Val-OH, the less polar component of the title compound with the desired configuration of the carbon atom bonded to the isopropyl group (S-configuration), is obtained in the form of a yellow oil. $R_f$(N16)=0.20; $R_f$(N6)=0.35.

(j) Z-Cha≃Val-NHMe: A mixture of 311.9 mg of Z-Cha≃Val-OH, 6.4 ml of DMF, 138.2 mg of HOBt and 186.1 mg of DCCI is left to stand for 24 hours at 0°. Excess methylamine is added to the mixture and the whole is stirred for 2 hours at 0° and for 2 hours at room temperature. The crystallised DCH is filtered off and the filtrate is concentrated and dried in a high vacuum. The title compound is obtained in the form of a colourless oil by flash chromatography of the residue (eluant system N3) $R_f$(N3)=0.45.

(k) H-Cha≃Val-NHMe: 243 mg of Z-Cha≃Val-NHMe are hydrogenated in 10 ml of methanol/water 9:1 in the presence of 50 mg of palladium-on-carbon (10% Pd) at normal pressure and room temperature until saturation is reached. The reaction mixture is filtered and the filtrate is stirred at room temperature with 10 ml of water. The title compound is obtained in the form of a colourless oil by evaporating off the solvent. $R_f$(B4)=0.11; $R_f$(S4)=0.31.

Example 17:
N-(2(R,S)-Acetoxy-3-α-naphthylpropionyl)-His-Leu≃Val-n-butylamide 22.2 mg of DCCI are added at 0°, while stirring, to a solution of 21.4 mg of 2(R,S)-acetoxy-3-α-naphthylpropionic acid, 35 mg of H-His-Leu≃Val-n-butylamide and 12.7 mg of HOBt in 1.5 ml of absolute DMF. The reaction mixture is further stirred for 12 hours at 0° and 48 hours at room temperature and then filtered. The filtrate is concentrated by evaporation at 40° and the residue is maintained at 60° for 60 minutes in 2 ml of a mixture of methanol/water/glacial acetic acid (94:3:3). Subsequently, the solution is concentrated by evaporation in a rotary evaporator and briefly dried in a high vacuum, and the resulting residue is chromatographed on silica gel with the solvent system B28, yielding the title compound in the form of white crystals. $R_f$(B4)=0.415.

The starting material is manufactured in the following manner:

(a) 2(R,S)-Acetoxy-3-α-naphthylpropionic acid: A mixture of 0.21 g of 2-hydroxy-3-α-naphthylpropionic acid and 0.2 ml of acetyl chloride is stirred at room temperature for 40 minutes and then concentrated by evaporation in a rotary evaporator at below 50°. The title compound remaining is dried over potash for 16 hours at 40° in a high vacuum. $R_f$(N18)=0.63.

(b) 2-Hydroxy-3-α-naphthylpropionic acid: A solution of 1.4 g of 2-bromo-3-α-naphthylpropionic acid and 1.4 g of calcium carbonate in 14 ml of water is boiled at reflux for 10 hours, cooled, adjusted to pH 2 with 2N hydrochloric acid, and extracted with ethyl acetate. The organic phases are dried with sodium sulphate and concentrated by evaporation. The crystalline title compound is obtained from the residue by chromatography on silica gel with eluant N21. $R_f$(N18)=0.5.

(c) 2-Bromo-3-α-naphthylpropionic acid: To a solution - of 10 g of α-naphthylamine in 100 ml of acetone there are added dropwise, while stirring, at room temperature, 39.2 ml of concentrated HBr and then, at 0°–5°, 17.4 ml of a 4N aqueous solution of sodium nitrite. Subsequently, 70 ml of acrylic acid are rapidly added dropwise and 0.4 g of copper(I) bromide are added. The reaction mixture is adjusted to pH 3 at 60° with approximately 30 g of sodium acetate, further stirred for 90 minutes at 70°, and then concentrated by evaporation in a rotary evaporator. The residue is dissolved in ethyl acetate and extracted four times with sodium bicarbonate solution. The bicarbonate extracts are rendered acidic with hydrochloric acid and extracted with ethyl acetate. The organic phases are washed with water and brine, dried over sodium sulphate and concentrated by evaporation. Chromatography of the residue with toluene/ethyl acetate (9:1) on silica gel yields the title compound in the form of brownish crystals. $R_f$(N19)=0.25.

Example 18:
N-[4-(2-Benzofuranyl)-2(R,S)-benzyl-4-oxobutyryl]-His-Leu≃Val-n-butylamide The title compound is obtained analogously to Example 17 from 50 mg of 4-(2-benzofuranyl)-2-(R,S)-benzyl-4-oxobutyric acid, 50 mg of H-His-Leu≃Val-n-butylamide, 25 mg of HOBt and 36 mg of DCCI and purified by flash chromatography with solvent system B7. $R_f$(B7)=0.30.

The starting material is manufactured in the following manner:

(a) 4-(2-Benzofuranyl)-2(R,S)-benzyl-4-oxobutyric acid: 2.0 g of (benzofuranyl-2-carbonylmethyl)-benzyl-malonic acid diethyl ester are dissolved in 10 ml of ethanol and, at room temperature, 10 ml of water and 7.4 ml of 2N sodium hydroxide solution are added in succession thereto. After stirring for 16 hours at room temperature, the reaction mixture is acidified to pH 3 with 1N HCl and extracted with methylene chloride. The crude di-acid, m.p. 154°, crystallises on concentration. The di-acid crystals are decarboxylated in a round-bottomed flask for 10 minutes at a temperature of 170°. After cooling the melt, crystallisation from ethyl acetate/hexane is carried out, resulting in the pure title compound, m.p. 170°–171°. $R_f$(N12)=0.63.

(b) (Benzofuranyl-2-carbonylmethyl)-benzylmalonic acid diethyl ester: 5.0 g of benzylmalonic acid diethyl ester are added dropwise at room temperature to a suspension of 870 mg of sodium hydride in 25 ml of DMF. After 20 minutes, 4.78 g of bromomethyl-2-benzofuranyl ketone (manufactured according to Liebigs Ann. Chem. 312, 332 (1900)) dissolved in 25 ml of DMF are added dropwise. After stirring for 2 hours at room temperature, the whole is poured onto ice and 1N HCl and extracted with methylene chloride. The crude product is purified by flash chromatography on 260 g of silica gel with methylene chloride as eluant, yielding the title compound in the form of an oil. $R_f$(CH$_2$Cl$_2$)=0.23.

Example 19:
N-(4-Cyano-2(R,S)-α-naphthylmethylbutyryl)His-Leu≃Val-n-butylamide Analogously to Example 17, the title compound is obtained from 21.0 mg of 4-cyano-2(R,S)-α-naphthylmethylbutyric acid, 35.0 mg of H-His-Leu≃Val-N-butylamide, 12.7 mg of HOBt and 22.2 mg of DCCI and purified by flash chromatography with solvent system B3. $R_f$(B4)=0.46 (slower diastereoisomer).

The starting material is manufactured in the following manner:

(a) 4-Cyano-2(R,S)-α-naphthylmethylbutyric acid: 2.13 g of 2-cyanoethylmalonic acid diethyl ester are added to a suspension of 0.48 g of sodium hydride dispersion in 25 ml of DMF. The reaction mixture is stirred for 2 hours at 80° and then, at room temperature, 1.77 g of α-chloromethylnaphthalene in 5 ml of DMF are added. The mixture is further stirred for 16 hours at 50° and then concentrated by evaporation. The residue is dissolved in ethyl acetate, washed with 0.1N hydrochloric acid and water, dried over sodium sulphate and concentrated by evaporation, leaving 2-cyanoethyl-α-naphthylmethylmalonic acid diethyl ester.

7.2 g of this intermediate product are stirred for 3 hours at 180° in 36 ml of DMSO, 360 μl of water and 1.73 g of lithium chloride. The reaction mixture is concentrated by evaporation in a high vacuum, the residue is dissolved in ethyl acetate, washed with water and brine, dried over sodium sulphate and concentrated by evaporation, yielding 4-cyano-2(R,S)-α-naphthylmethylbutyric acid ethyl ester.

For hydrolysis 0.45 g of this ester is stirred for 16 hours at 35° in 7 ml of methanol and 1.8 ml of 1N sodium hydroxide solution. Subsequently the reaction mixture is concentrated by evaporation, the residue is dissolved in water, washed with ethyl acetate, acidified with 2N sulphuric acid and extracted with ethyl acetate. The ethyl acetate extracts are washed with water, dried over sodium sulphate and concentrated by evaporation to yield the title compound in the form of a yellow oil.

Example 20: N-(2(R)- and 2(S)-cyanomethyl-3-α-naphthylpropionyl)-His-Leu≃Val-n-butylamide Analogously to Example 17, the title compound is obtained in the form of a diastereoisomeric mixture from 19.9 mg of 2(R,S)-cyanomethyl-3-α-naphthylpropionic acid, 35.0 mg of H-His-Leu≃Val-n-butylamide, 12.7 mg of HOBt and 22.2 mg of DCCI and separated by flash chromatography with solvent system B28. $R_f$(B4)=0.46 (more rapid diastereoisomer); $R_f$(B4)=0.44 (slower diastereoisomer).

The starting material is manufactured in the following manner:

(a) 2(R,S)-Cyanomethyl-3-α-naphthylpropionic acid: 3.0 g of α-naphthylmethylmalonic acid diethyl ester and, after 30 minutes, 0.6 ml of chloroacetonitrile are added to a stirred suspension of 0.44 g of sodium hydride dispersion in 50 ml of DMF. The reaction mixture is stirred for 1 hour at 50° and then concentrated by evaporation in a high vacuum. The residue is dissolved in ethyl acetate, washed with 0.1N hydrochloric acid and water, dried over sodium sulphate, concentrated by evaporation and purified by chromatography on silica gel with toluene, yielding cyanomethyl-(α-naphthylmethyl)-malonic acid diethyl ester.

Analogously to Example 19a), this malonic ester is hydrolysed and decarboxylated, and the resulting 2(R,S)-cyanomethyl-3-α-naphthylpropionic acid ethyl ester is purified by chromatography with solvent system N4 and hydrolysed with sodium hydroxide solution in methanol, yielding the title compound in the form of a yellowish oil.

Example 21:
N-Benzyloxycarbonyl-(p-benzyloxycarbonylamino-Phe)-His-Leu$^c$Val-n-butylamide Analogously to Example 17, the title compound is manufactured from 58 mg of N-benzyloxycarbonyl-p-benzyloxycarbonylamino-L-phenylalanine, 50 mg of H-His-Leu$^c$Val-n-butylamide, 20 mg of HOBt and 32 mg of DCCI and purified by flash chromatography with solvent system B31. $R_f$(B8)=0.51.

The starting material is manufactured in the following manner:

(a) N-Benzyloxycarbonyl-p-benzyloxycarbonylamino-L-phenylalanine: 1.01 g of p-amino-L-phenylalanine (Bachem AG, Bubendorf) is taken up in the form of a sodium salt in 6 ml of H$_2$O. Then, while cooling with an ice bath, 3.35 ml of chloroformic acid benzyl ester (50% in toluene) and 5 ml of 2N NaOH are simultaneously added dropwise and the whole is then stirred for 20 minutes. The white suspension is adjusted to pH 1 with 2N HCl, extracted with ethyl acetate, and the organic phase is dried over sodium sulphate and concentrated by evaporation. The residue is purified by flash chromatography with solvent system B11. The eluate is acidified with 2N HCl and extracted with ethyl acetate, and the extracts are dried and concentrated by evaporation to yield the title compound in the form of white crystals. $R_f$(B11)=0.22.

Example 22:
N-Pivaloyl-(p-benzyloxycarbonylamino-Phe)His-Leu$^c$-Val-n-butylamide Analogously to Example 17, the title compound is manufactured from 52 mg of N-pivaloyl-p-benzyloxycarbonylamino-L-phenylalanine, 50 mg of H-His-Leu$^c$Val-n-butylamide, 20 mg of HOBt and 32 mg of DCCI and purified by flash chromatography with solvent system B31. $R_f$(B8)=0.41.

The starting material is manufactured in the following manner:

(a) N-Pivaloyl-p-benzyloxycarbonylamino-L-phenylalanine: 2.22 g of N-pivaloyl-p-amino-L-phenylalanine are introduced into 4 ml of 2N NaOH and 5 ml of H$_2$O. While cooling with an ice bath, 1.3 ml of chloroformic acid benzyl ester and 2.1 ml of 4N NaOH are simultaneously added dropwise. The suspension is then stirred for 30 minutes and subsequently adjusted to pH 1 with concentrated HCl. It is extracted with ethyl acetate, washed with water, dried, and the solvent is evaporated off in vacuo, yielding beige crystals. $^1$H-NMR (DMSO-d$_6$, TMS): 1.0 ppm (s, 9H); 2.9–3.0 (dd, 2H); 4.4 (m, 1H); 5.15 (s, 2H); 5.72 (s, 2H); 7.1 (d, 1H); 7.3–7.5 (m, 5H); 14.6 (s, 1H).

(b) N-Pivaloyl-p-amino-L-ohenylalanine: 2.73 g of N-pivaloyl-p-nitro-L-phenylalanine in 50 ml of methanol are hydrogenated in the presence of 270 mg of palladium-on-carbon (10% Pd) for 20 minutes at normal pressure and room temperature. The catalyst is filtered off and the filtrate is concentrated to dryness by evaporation, leaving the title compound in the form of a pink-red powder. $^1$H-NMR (DMSO-d$_6$, TMS): 1.05 ppm (s, 9H); 2.8–2.95 (m, 2H); 4.2–4.5 (m, 1H); 6.45 (d, 2H); 6.9 (d, 2H); 7.25 (d, 1H).

(c) N-Pivaloyl-p-nitro-L-phenylalanine: 2.0 g of p-nitro-L-phenylalanine (Bachem AG, Bubendorf) are dissolved in 5 ml of 2N NaOH and 2 ml of THF and, at 10°–15°, 1.2 ml of pivaloyl chloride in 1.3 ml of toluene and 2.4 ml of 4N NaOH are simultaneously added. The whole is then stirred for 1 hour at room temperature and subsequently adjusted to pH 1 with concentrated HCl. The aqueous phase is extracted with ethyl acetate and the organic phase is dried and concentrated by evaporation, yielding the title compound in the form of a yellowish powder. $R_f$(N20)=0.23.

Example 23

The following are manufactured analogously to Example 17:

(a) N-(2(R)- and 2(S)-hydroxy-3-α-naphthylpropionyl)His-Leu$^c$Val-n-butylamide, separation of the diastereoisomers by flash chromatography with solvent system B30; $R_f$(B4)=0.43 (slower diastereoisomer) and $R_f$(B4)=0.49 (more rapid diastereoisomer).

(b) N-(3-α-naphthylpropionyl)-His-Leu$^c$Val-n-butylamide, flash chromatography with eluant B28; $R_f$(B4)=0.41.

(c) N-(quinolyl-2-carbonyl)-His-Leu$^c$Val-n-butylamide, medium-pressure chromatography on Lobar®-prefabricated column with eluant B31; $R_f$(B8)=0.64.

(d) N-(8-Naphthylcarbonyl)-His-Leu$^c$Val-n-butylamide, flash chromatography with eluant B31; $R_f$(B8)=0.60.

(e) N-(α-Naphthoxyacetyl)-His-Leu$^c$Val-n-butylamide, flash chromatography with eluant B23; $R_f$(B4)=0.49.

(f) N-(2(R,S)-Benzyl-5,5-dimethyl-4-oxohexanoyl)-His-Leu$^c$Val-n-butylamide: $R_f$(B7)=0.33. The starting material is described in Example 25a.

Example 24:
N-(2(R,S)-Acetoxy-3-α-naphthylpropionyl)-His-Cha$^c$Val-n-butylamide Analogously to Example 17, the title compound is obtained from 30 mg of 2(R,S)-acetoxy-3-α-naphthylpropionic acid, 54 mg of H-His-Cha$^c$Val-n-butylamide, 17.8 mg of HOBt and 31 mg of DCCI and purified by flash chromatography with solvent system B28. $R_f$(B4)=0.5.

The starting material is manufactured in the following manner:

(a) H-His-Cha$^c$Val-n-butylamide is obtained, analogously to Example 16a, by hydrogenating 1.6 g of Z-His-Cha$^c$Val-n-butylamide in the presence of 200 mg of palladium-on-carbon (10%). $R_f$ (B4)=0.05; $R_f$ (S4)=0.16.

(b) Z-His-Cha$^c$Val-n-butylamide is obtained analogously to Example 16b from 1.75 g of Z-His-OH, 1.97 g of H-Cha$^c$Val-n-butylamide, 930 mg of HOBt and 1.62 g of DCCI and purified by flash chromatography with solvent system B4. M.p. 208°–210° $R_f$(B4)=0.49; $R_f$(S4)=0.62.

(c) H-Cha$^c$Val-n-butylamide is obtained, analogously to Example 16k, by hydrogenating 4.2 g of Z-Cha$^c$Valn-butylamide in the presence of 500 mg of palladium-on-carbon (10%). $R_f(B4)=0.25$.

(d) Z-Cha≅Val-n-butylamide is obtained analogously to Example 16j from 4.01 g of Z-Cha≅Val-Oh, 2.68 g of n-butylamine, 1.80 g of HOBt and 2.41 g of DCCI and purified by flash chromatography with solvent system N4. $R_f(N3)=0.61$.

Example 25: N-(2(R,S)-, 2(R)- and 2(S)-benzyl-5,5-dimethyl-4-oxohexanoyl)-His-Cha≅Val-n-butylamide Analogously to Example 24, the corresponding title compound is obtained from 40 mg of 2(R,S)-, 2(R)- and 2(S)-benzyl-5,5-dimethyl-4-oxohexanoic acid, respectively, 50 mg of H-His-Cha≅Val-n-butylamide, 25 mg of HOBt and 36 mg of DCCI and purified by flash chromatography with solvent system B5. $R_f(B5)=0.24$; $R_f(B7)=0.35$ (both diastereoisomers).

The starting materials are manufactured in the following manner:

(a) 2(R,S)-Benzyl-5,5-dimethyl-4-oxohexanoic acid: Analogously to Examples 18a and 18b, the title compound is obtained from 5.0 g of benzylmalonic acid diethyl ester, 870 mg of sodium hydride and 3.58 g of bromomethyl-tert.-butyl ketone in DMF. M.p. 94°-95°. $R_f(N11)=0.56$.

(b) 2(R)- and 2(S)-benzyl-5,5-dimethyl-4-oxohexanoic acid: 400 mg of the racemate from Example 25a, 370 mg of 2(S)-amino-3-phenylpropanol (L-phenylalaninol), 272 mg of HOBt and 500 mg of DCCI are reacted analogously to Example 1. The diastereoisomers are separated by flash chromatography with solvent system N3. $R_f(N3)=0.23$ (more rapid diastereoisomer) and $R_f(N3)=0.17$ (slower diastereoisomer). By boiling with acetic acid/2N HCl 1:1 for 10 hours at 80°, the phenylalaninol radical is removed again and the title compounds are isolated in the form of pure enantiomers.

Example 26:
N-(2(R,S)-Ethoxycarbonyl-3-α-naphthylpropionyl)-His-Cha≅Val-n-butylamide Analogously to Example 24, the title compound is obtained from 42 mg of α-naphthylmethylmalonic acid monoethyl ester, 60 mg of H-His-Cha≅Val-n-butylamide, 26 mg of HOBt and 40 mg of DCCI and purified by flash chromatography with solvent system B5. $R_f(B5)=0.22$; $R_f(B7)=0.36$.

The starting material is manufactured in the following manner:

(a) α-Naphthylmethylmalonic acid monoethyl ester: 16.5 ml of 1N NaOH are added to 5.0 g of α-naphthylmethylmalonic acid diethyl ester (J. Am. Chem. Soc. 62, 2335 (1940)) dissolved in 50 ml of water/ethanol 1:1. After 30 minutes at room temperature the hydrolysis is complete. 16.5 ml of 1N HCl are added to the reaction mixture and extraction is carried out with methylene chloride. The extracts are concentrated by evaporation and the residue is purified by flash chromatography with solvent system N11. $R_f(N11)=0.35$; $R_f(N7)=0.25$.

Example 27:
N-(Cyclohepta[b]pyrrolyl-5-carbonyl)-His-Cha≅Val-n-butylamide

Analogously to Example 24, the title compound is obtained from 37 mg of cyclohepta[b]pyrrole-5-carboxylic acid, 60 mg of H-His-Cha≅Val-n-butylamide, 32 mg of HOBt and 48 mg of DCCI and purified by flash chromatography with solvent system B7. $R_f(B7)=0.35$.

The starting material is manufactured in the following manner:

(a) Cyclohepta[b]pyrrole-5-carboxylic acid: 260 mg of cyclohepta[b]pyrrole-5-carboxylic acid nitrile are boiled under reflux for 24 hours in 16 ml of a 1:1 mixture of ethanol and 10N sodium hydroxide solution. Subsequently the whole is acidified with concentrated hydrochloric acid, extracted with methylene chloride, and the extracts are concentrated by evaporation. $R_f(B11)=0.18$; $R_f(N12)=0.55$.

(b) Cyclohepta[b]pyrrole-5-carboxylic acid nitrile: 800 mg of cyclohepta[b]pyrrole (manufactured according to Helv. Chim. Acta 67, 1647 (1984)) are added in portions, at 0°, to a solution of 1.1 ml of oxalyl chloride in 40 ml of DMF. The whole is subsequently stirred for 30 minutes at room temperature, then 60 ml of saturated sodium acetate solution are added and the pH is adjusted to 9 with concentrated ammonia. The cyclohepta[b]pyrrole-5-carbaldehyde formed is extracted with methylene chloride and purified by flash chromatography with solvent system N6. $R_f(N6)=0.46$.

300 mg of this aldehyde are stirred vigorously with 640 mg of hydroxylamine and 1.5 g of sodium acetate in 20 ml of methanol at room temperature. The reaction mixture is poured onto water and the cyclohepta[b]pyrrole-5-carbaldoxime formed is extracted with methylene chloride. $R_f(N6)=0.35$.

371 mg of N,N'-carbonyldiimidazole are added to 340 mg of this oxime in 20 ml of methylene chloride at room temperature. After 1 hour the reaction mixture is applied directly to 65 g of silica gel and, under slight over-pressure, the title compound is eluted with solvent system B6. $R_f(B6)=0.70$.

Example 28:
N-[2(R,S)-(2-Dimethylaminoethylcarbamoyl)3-α-naphthylpropionyl]-His-Cha≅Val-n-butylamide Analogously to Example 24, the title compound is obtained from 49 mg of 2(R,S)-(2-dimethylaminoethylcarbamoyl)-3-α-naphthylpropionic acid, 60 mg of H-His-Cha≅Val-n-butylamide, 26 mg of HOBt and 40 mg of DCCI and purified by flash chromatography with solvent system B9. $R_f(B9)=0.27$; $R_f(B7)=0.13$.

The starting material is manufactured in the following manner:

(a) 2(R,S)-(2-Dimethylaminoethylcarbamoyl)-3-α-naphthylpropionic acid: 2(R,S)-(2-dimethylaminoethylcarbamoyl)-3-α-naphthylpropionic acid ethyl ester is manufactured analogously to Example 1 from 1.00 g of α-naphthylmethylmalonic acid monoethyl ester (Example 26a), 0.80 ml of 2-dimethylaminoethylamine, 0.67 g of HOBt and 1.14 g of DCCI. $R_f(B5)=0.33$; $R_f(B7)=0.46$.

The ethyl ester is hydrolysed analogously to Example 26a with sodium hydroxide solution in aqueous ethanol. The title compound crystallises from water at 4° in the form of thin colourless crystals having a melting point of 102°. $R_f(B11)=0.08$.

Example 29:
N-[2(R,S)-(2-Hydroxy-1(S)-methylethylcarbamoyl)-3-α-naphthylpropionyl]-His-Cha≅Val-n-butylamide Analogously to Example 24, the title compound is obtained from 47 mg 2(R,S)-(2-hydroxy-1(S)-methylethylcarbamoyl)-3-α-naphthylpropionic acid, 60 mg of H-His-Cha≅Val-n-butylamide, 26 mg of HOBt and 40 mg of DCCI and purified by flash chromatography with solvent system B7. $R_f(B7)=0.22$; $R_f(B9)=0.31$.

The starting material is manufactured in the following manner:

(a) 2(R,S)-(2-Hydroxy-1(S)-methylethylcarbamoyl)-3-α-naphthylpropionic acid is manufactured analogously to Example 28a from 2.00 g of α-naphthylmethylmalonic acid monoethyl ester (Example 26a), 0.69 g of 2(S)-amino-1-propanol, 1.46 g of HOBt and 2.27 g of DCCI. $R_f(B11)=0.18$; $R_f(S10)=0.52$.

Example 30:
N-[2(R,S)-(2,2-Dimethoxyethylcarbamoyl)-3-α-naphthylpropionyl]-His-Cha≗Val-n-butylamide Analogously to Example 24, the title compound is obtained from 51 mg of 2(R,S)-(2,2-dimethoxyethylcarbamoyl)-3-α-naphthylpropionic acid, 60 mg of H-His-Cha≗Val-n-butylamide, 26 mg of HOBt and 40 mg of DCCI and purified by flash chromatography with solvent system B7. $R_f(B7)=0.35$; $R_f(B5)=0.20$.

The starting material is manufactured in the following manner:

(a) 2(R,S)-(2,2-Dimethoxyethylcarbamoyl)-3-α-naphthylpropionic acid is manufactured analogously to Example 28a from 1.00 g of α-naphthylmethylmalonic acid monoethyl ester (Example 26a), 0.48 ml of aminoacetaldehyde-dimethyl acetal, 0.73 g of HOBt and 1.14 g of DCCI. $R_f(B11)=0.28$; $R_f(S10)=0.65$.

Example 31:
N-[2(R,S)-(tert.-butoxycarbonylmethylcarbamoyl)-3-α-naphthylpropionyl]-His-Cha≗Val-n-butylamide Analogously to Example 24, the title compound is manufactured from 92 mg of 2(R,S)-(tert.-butoxycarbonylmethylcarbamoyl)-3-α-naphthylpropionic acid, 100 mg of H-His-Cha≗Val-n-butylamide, 43 mg of HOBt and 67 mg of DCCI and purified by flash chromatography with solvent system B5. $R_f(B5)=0.21$; $R_f(B7)=0.34$.

The starting material is manufactured in the following manner:

(a) 2(R,S)-(tert.-butoxycarbonylmethylcarbamoyl)-3-α-naphthylpropionic acid is manufactured analogously to Example 28a from 1.00 g of α-naphthylmethylmalonic acid monoethyl ester (Example 26a), 1.73 g of glycine tert.-butyl ester dibenzenesulphimide salt, 0.73 g of HOBt and 1.14 g of DCCI and purified by flash chromatography with solvent system N12. $R_f(N12)=0.38$.

Example 32:
N-[2(R,S)-Carboxymethylcarbamoyl-3-α-naphthylpropionyl]-His-Cha≗Val-n-butylamide 90 mg of N-[2(R,S)-(tert.-btuoxycarbonylmethylcarbamoyl)-3-α-naphthylpropionyl]-His-Cha≗Val-n-butylamide (Example 31) are dissolved in 0.5 ml of trifluoroacetic acid and left to stand at room temperature for 1 hour. Subsequently the whole is concentrated to dryness by evaporation and the product is purified by flash chromatography with solvent system B11. $R_f(B11)=0.34$; $R_f(B9)=0.21$.

Example 33:
N-(5,5-Dimethyl-2(R,S)-α-naphthylmethyl-4-oxohexanoyl)-His-Cha≗Val-n-butylamide Analogously to Example 24, the title compound is obtained from 46 mg of 5,5-dimethyl-2(R,S)-(α-naphthylmethyl)-4-oxohexanoic acid, 60 mg of H-His-Cha≗Val-n-butylamide, 26 mg of HOBt and 40 mg of DCCI and purified by flash chromatography with solvent system B5. $R_f(B5)=0.21$; $R_f(B7)=0.37$.

The starting material is manufactured in the following manner:

(a) 5,5-Dimethyl-2(R,S)-α-naphthylmethyl-4-oxohexanoic acid: Analogously to Examples 18a and 18b, the title compound is obtained from 5.0 g of α-naphthylmethylmalonic acid diethyl ester (J. Am. Chem. Soc. 62, 335 (1940)), 730 mg of sodium hydride and 2.9 g of bromomethyl-tert.-butyl ketone in DMF with subsequent hydrolysis and decarboxylation. M.p. 93°–93.5°. $R_f(N11)=0.50$.

Example 34:
N-(Ethoxycarbonyl-α-naphthoxyacetyl)His-Cha≗Val-n-butylamide

Analogously to Example 24, the title compound is manufactured from 29.6 mg of α-naphthoxymalonic acid monoethyl ester, 50.0 mg of H-His-Cha≗Val-n-butylamide, 16.5 mg of HOBt and 28.8 mg of DCCI and purified by flash chromatography with solvent system B3. $R_f(B4)=0.54$.

The starting material is manufactured in the following manner:

(a) α-Naphthoxymalonic acid monoethyl ester: 2.0 g of α-naphthoxymalonic acid diethyl ester are dissolved in 5 ml of absolute ethanol and, while stirring, a solution of 0.41 g of potassium hydroxide in 5 ml of absolute ethanol is added. The reaction mixture is stirred at room temperature for 16 hours and then concentrated to dryness by evaporation. The residue is dissolved in water, washed with ether, acidified with 5N hydrochloric acid and extracted with ethyl acetate. The title compound is obtained in the form of a light brown oil from these ethyl acetate extracts by washing with brine, drying over sodium sulphate and concentration by evaporation.

Example 35:
N-(4-Cyano-2(R,S)-α-naphthoxybutyryl)-His-Cha≗Val-n-butylamide

Analogously to Example 24, the title compound is manufactured from 27.6 mg of 4-cyano-2(R,S)-α-naphthoxybutyric acid, 50.0 mg of H-His-Cha≗Val-n-butylamide, 16.5 mg of HOBt and 28.8 mg of DCCI and purified by flash chromatography with solvent system B28. $R_f(B4)=0.52$.

The starting material is manufactured in the following manner:

(a) 4-Cyano-2(R,S)-α-naphthoxybutyric acid: 0.11 ml of a 50% aqueous KOH solution is added at 0°, while stirring, to a mixture of 5.0 g of α-naphthoxymalonic acid diethyl ester and 1.09 ml of acrylonitrile. The reaction mixture is stirred for 5 days at room temperature and then dissolved in ethyl acetate. The ethyl acetate solution is washed with 2N sodium bicarbonate solution, 2N hydrochloric acid and brine, dried over sodium sulphate and concentrated by evaporation, leaving (2-cyanoethyl)-α-naphthoxymalonic acid diethyl ester.

7.84 g of this malonic ester are stirred for 3 hours at 180° in 39.2 ml of DMSO, 398 μl of water and 1.87 g of lithium chloride. The reaction mixture is concentrated by evaporation in a high vacuum, the residue is dissolved in ethyl acetate and extracted with water. The aqueous extracts are adjusted to pH 2 with 2N hydrochloric acid and extracted with ethyl acetate. The ethyl acetate extracts are washed with water and brine, dried over sodium sulphate and concentrated by evaporation, yielding the title compound in the form of a light brown oil.

Example 36
N-(4-tert.-butoxycarbonyl-2(R,S)-α-naphthoxybutyryl)-His-Cha£Val-n-butylamide Analogously to Example 24, the title compound is manufactured from 35.7 mg of 4-tert.-butoxycarbonyl2(R,S)-α-naphthoxybutyric acid, 50.0 mg of H-His-Cha£Val-n-butylamide, 16.5 mg of HOBt and 28.8 mg of DCCI and purified by flash chromatography with solvent system B28. $R_f(B4)=0.33$.

The starting material is manufactured in the following manner:

(a) 4-tert.-butoxycarbonyl-2(R,S)-α-naphthoxybutyric acid: A solution of 25 g of 1-naphthol in 50 ml of DMF is slowly added dropwise to a solution of 7.6 g of sodium hydride dispersion in 300 ml of DMF. The suspension is stirred for 30 minutes and subsequently 41.5 g of bromomalonic acid diethyl ester in 50 ml of DMF are added dropwise. The reaction mixture is further stirred for 16 hours at room temperature and then concentrated by evaporation in a high vacuum. The residue is dissolved in ethyl acetate and washed with 2N sodium hydroxide solution, water and brine, dried over sodium sulphate and concentrated by evaporation. The residue is distilled at 145°–170°/2.6 Pa and yields α-naphthoxymalonic acid diethyl ester in the form of an orange-coloured oil.

1.49 ml of 1,8-diazabicyclo[5.4.0]undec-7-ene is added to a solution of 3.0 g of this malonic acid ester and 1.45 ml of acrylic acid tert.-butyl ester in 5 ml of acetonitrile and the whole is stirred at room temperature for 24 hours. 25 ml of water are added to the reaction mixture which is then adjusted to pH 2 with approximately 12 ml of 2N hydrochloric acid and extracted with ether. The ethereal phases are washed with brine and water, dried over sodium sulphate and concentrated by evaporation, leaving (2-tert.-butoxycarbonylethyl)-α-naphthoxymalonic acid diethyl ester in the form of a light brown oil.

This ester is hydrolysed with lithium chloride and water in DMSO at 180° analogously to Example 35a and decarboxylated. The crude acid is purified by chromatography with solvent system B4 and yields the title compound in the form of a white foam.

Example 37:
N-(2(R,S)-Ethylaminocarbonyloxy-3-α-naphthylpropionyl)-His-Cha£Val-n-butylamide Analogously to Example 24, the title compound is manufactured from 15.5 mg of 2(R,S)-ethylaminocarbonyloxyoxyl-3-α-naphthylpropionic acid, 25.0 mg of H-His-Cha£Val-n-butylamide, 8.3 mg of HOBt and 14.4 mg of DCCI and purified by flash chromatography with solvent system B28. $R_f(B29)=0.25$.

The starting material is manufactured in the following manner:

(a) 2(R,S)-Ethylaminocarbonyloxy-3-α-naphthylpropionic acid: 54 μl of ethyl isocyanate are added to a solution of 50 mg of 2-hydroxy-3-α-naphthylpropionic acid (Example 17b) in 2 ml of DMF. The reaction mixture is stirred for 3 hours at 100° and then concentrated by evaporation in a rotary evaporator under a high vacuum. The residue is dissolved in ethyl acetate, washed with 0.1N hydrochloric acid, water and brine, dried over sodium sulphate, concentrated by evaporation and purified by chromatography on silica gel with solvent system B11. Yellow oil. $R_f(B11)=0.27$.

Example 38:
N-[2(R,S)-(2-Benzyloxycarbonylamino-2-methylpropionyloxy)-3-α-naphthylpropionyl]-His-Cha£Val-n-butylamide Analogously to Example 24, the title compound is manufactured from 47.0 mg of 2(R,S)-(2-benzyloxycarbonylamino-2-methylpropionyloxy)-3-α-naphthylpropionic acid, 50.0 mg of H-His-Cha£Val-n-butylamide, 16.5 mg of HOBt and 28.2 mg of DCCI and purified by flash chromatography with solvent system B30. $R_f(B29)=0.38$.

The starting material is manufactured in the following manner:

(a) 2(R,S)-(2-Benzyloxycarbonylamino-2-methylpropionyloxy)-3-α-naphthylpropionic acid: A solution of 0.77 g of α-benzyloxycarbonylaminoisobutyric acid in 5 ml of DMF and, after 30 minutes, 1 g of 2-bromo-3-α-naphthylpropionic acid ethyl ester in 5 ml of DMF are added dropwise, at room temperature, to a stirred suspension of 0.14 g of sodium hydride (55% in mineral oil) in 10 ml of DMF. The reaction mixture is stirred for 16 hours at room temperature and then concentrated by evaporation in a high vacuum. The residue is dissolved in ethyl acetate, washed with water and brine, dried over sodium sulphate and concentrated by evaporation. Chromatography of the residue on silica gel with toluene/ethyl acetate (95:5) yields the ethyl ester of the title compound For hydrolysis, 20.8 mg of LiOH.H$_2$O are added at 0° to 230 mg of the ester dissolved in 5 ml of THF/water (9:1). The reaction mixture is stirred for 20 hours at 0° and then extracted three times with ethyl acetate. The ethyl acetate phases are washed with water and brine, dried over sodium sulphate and concentrated by evaporation. Chromatography of the residue on silica gel with solvent system B11 yields the title compound in the form of a yellow oil, $R_f(B11)=0.34$.

Example 39:
N-(3-Phenyl-2(S)-pivaloyloxypropionyl)-His-Cha£Val-n-butylamide

Analogously to Example 24, the title compound is manufactured from 30 mg of 3-phenyl-2(S)-pivaloyloxypropionic acid, 50 mg of H-His-Cha£Val-n-butylamide, 18 mg of HOBt and 29 mg of DCCI and purified by medium-pressure chromatography over a Lobar ® prefabricated column with methylene chloride/methanol/concentrated ammonia 150:10:1. $R_f(B8)=0.45$.

The starting material is manufactured in the following manner:

(a) 3-Phenyl-2(S)-pivaloyloxypropionic acid: 3.01 g of 3-phenyl-2(S)-pivaloyloxypropionic acid benzyl ester are hydrogenated for 30 minutes at room temperature under normal pressure in 35 ml of methanol in the presence of 300 mg of palladium-on-carbon (10%). The catalyst is filtered off and the filtrate is concentrated by evaporation in vacuo. The title compound is obtained in the form of a clear colourless oil. $R_f(N21)=0.74$. $^1$H-NMR (DMSO-d6): 12.5 (1H); 7.25 (s, 5H); 5.1 (dxd, 1H); 3.15 (m, 2H); 1.1 ppm (s, 9H).

(b) 3-Phenyl-2(S)-pivaloyloxypropionic acid benzyl ester: 0.24 ml of pivalic acid chloride in 2 ml of methylene chloride are added dropwise to a solution, cooled to 0° C., of 250 mg of 3-phenyl-2(S)-hydroxypropionic acid benzyl ester (L-β-phenyllactic acid benzyl ester)

and 0.408 ml of triethylamine in 5 ml of methylene chloride. The mixture is stirred for 30 hours at room temperature and subsequently poured onto ice. The organic phase is washed with 1N hydrochloric acid and water and dried over sodium sulphate. The solvent is evaporated off in vacuo and the residue is purified by medium-pressure chromatography (Lobar ® prefabricated column Merck, size B, eluant petroleum ether/ether 11:1). The title compound is obtained in the form of a colourless oil. $R_f$(N4)=0.52.

(c) 3-Phenyl-2(S)-hydroxypropionic acid benzyl ester: 23 ml of a 20% aqueous solution of caesium carbonate (pH 7) are added dropwise at room temperature to a solution of 4.0 g of L-β-phenyllactic acid (3-phenyl-2(S)-hydroxypropionic acid) in 65 ml of methanol and 6.5 ml of water. The solvent is evaporated off and the residue is dried in a high vacuum for 24 hours at room temperature. The dried caesium salt is taken up in 37 ml of anhydrous DMF, cooled to 0° and 3.15 ml of benzyl bromide are added dropwise thereto. The resulting white suspension is stirred for 24 hours at room temperature and subsequently filtered. The filtrate is concentrated by evaporation in a high vacuum, and the residue is taken up in ether, washed with water and saturated aqueous $NaHCO_3$ solution and dried over sodium sulphate. After evaporating off the solvent in vacuo the title compound is obtained in the form of a yellowish oil. $R_f$(N4)=0.2. $^1$H-NMR (DMSO-$d_6$): 7.3 (s, 5H); 7.2 (s, 5H); 5.6 (d, 1H); 5.15 (s, 2H); 4.4 (m, 1H), 3.0 ppm (m, 2H).

Example 40: N-(2(R,S)-, 2(R)- and 2(S)-dimethoxyphosphoryl-3-phenylpropionyl)-His-Cha$^c$Val-n-butylamide Analogously to Example 24, the title compound is obtained in the form of a diastereoisomeric mixture from 31 mg of 2(R,S)-dimethoxyphosphoryl-3-phenylpropionic acid, 50 mg of H-His-Cha$^c$Val-n-butylamide, 18 mg of HOBt and 29 mg of DCCI and purified by medium-pressure chromatography (Lobar ® prefabricated column, eluant methylene chloride/methanol/concentrated ammonia 120:10:1). $R_f$(B8)=0.46 (more rapid diastereoisomer); $R_f$(B8)=0.41 (slower diastereoisomer). The diastereoisomers can be separated by chromatography.

The starting material is manufactured in the following manner:

(a) 2(R,S)-Dimethoxyphosphoryl-3-phenylpropionic acid: 6.66 g of 2-dimethoxyphosphoryl-3-phenylpropionic acid methyl ester (α-benzylphosphonoacetic acid trimethyl ester) are placed in 20 ml of MeOH and, at room temperature, 8 ml of $H_2O$ and 12.14 ml of 2N KOH are added and the whole is stirred for 90 minutes. Subsequently, the reaction mixture is neutralised with 12.14 ml of 2N HCl, concentrated by evaporation to 20 ml, extracted with ethyl acetate, dried and concentrated by evaporation again. $^1$H-NMR (DMSO-$d_6$): 2.8–3.2 ppm (m, 2H); 3.6 (s, 3H); 3.75 (s, 3H); 7.2 (s, 5H).

(b) α-Benzylphosphonoacetic acid trimethyl ester: 0375 2.4 g of NaH (50% in oil) are placed in 250 ml of dimethoxyethane and, while cooling with an ice bath, 10 g of phosphonoacetic acid trimethyl ester in 40 ml of dimethoxyethane are added. The whole is stirred for 90 minutes at room temperature and then 6.52 ml of benzyl bromide in 40 ml of dimethoxyethane are added. After stirring for 4.5 hours at room temperature, the reaction mixture is poured onto 100 ml of a 2N aqueous solution of $NaH_2PO_4$ and ice and extracted with ether, and the organic phase is dried and concentrated by evaporation. The crude product is purified by medium-pressure chromatography (1400 g Lichoprep ® Si 60, 25–40 μm, eluant ethyl acetate/n-hexane 2:1 and pure ethyl acetate). $^1$H-NMR (DMSO-$d_6$): 2.9–3.4 ppm (m, 2H); 3.60 (s, 3H); 3.61 (s, 3H); 3.85 (s, 3H); 7.22 (s, 5H).

Example 41: Ammonium N-(2-(R,S)-methoxyoxidophosphoryl-3-phenylpropionyl)-His-Cha$^c$Val-n-butylamide and diammonium N-(3-phenyl-2(R,S)-phosphonatopropionyl)-His-Cha$^c$Val-n-butylamide 45 μl of trimethylbromosilane are added at room temperature to 43 mg of N-(2(R,S)-dimethoxyphosphoryl-3-phenylpropionyl)-His-Cha$^c$Val-n-butylamide (Example 40) in 1 ml of chloroform and the whole is left to stand for 30 hours. The reaction mixture is concentrated by evaporation, 1 ml of 1N hydrochloric acid is added, the whole is stirred for 1 hour at room temperature and concentrated by evaporation again. The residue is separated by flash chromatography (eluant methylene chloride/methanol/concentrated ammonia, first 10:5:1, then 5:3:1).

Methyl ester ammonium salt: $R_f$(B32)=0,38 (more rapid diastereoisomer); $R_f$(B32)=0.33 (slower diastereoisomer). Diammonium salt: $R_f$(B32)=0.32 (more rapid diastereoisomer); $R_f$(B32)=0.26 (slower diastereoisomer).

Example 42: N-(2(R,S)-Benzyl-3-diethoxyphosphorylpropionyl)-His-Cha$^c$Val-n-butylamide Analogously to Example 24, the title compound is manufactured from 93 mg of 2(R,S)-benzyl-3-diethoxyphosphorylpropionic acid, 130 mg of H-His-Cha$^c$Val-n-butylamide, 47 mg of HOBt and 75 mg of DCCI and purified by flash chromatography with solvent system B5. $R_f$(B8)=0.37 (more rapid diastereoisomer); $R_f$(B8)=0.32 (slower diastereoisomer).

The starting material is manufactured in the following manner:

(a) 2(R,S)-Benzyl-3-diethoxyphosphorylpropionic acid: 745 mg of 2-benzyl-3-diethoxyphosphorylpropionic acid ethyl ester are placed in 5 ml of ethanol and 4 ml of water, 1.13 ml of 2N KOH are added and the whole is stirred at room temperature for 4 hours, then neutralised with 1.13 ml of 2N HCl and concentrated by evaporation. The residue is purified by flash chromatography with solvent system N10. $R_f$(N8)=0.46. $^1$H-NMR (DMSO-$d_6$): 1.2 ppm (t, 6H); 1.7 (m, 1H); 2.05 (m, 1H); 2.7–3.0 (m, 3H); 3.95 (q, 4H); 7.15–7.35 (m, 5H).

(b) 2-Benzyl-3-diethoxyphosphorylpropionic acid ethyl ester: 4 ml of a 1% sodium ethoxide solution, 1.0 g of α-benzylacrylic acid ethyl ester and 0.68 ml of diethyl phosphite (phosphorous acid diethyl ester) in 5 ml of ethanol are added to 30 ml of ethanol at room temperature. The mixture is stirred for 24 hours at room temperature, then 200 mg of $NaH_2PO_4$ in 1 ml of water are added and the whole is concentrated by evaporation. The mixture is partitioned between ether and water and the organic phase is dried, concentrated by evaporation and purified by flash chromatography with methylene chloride/ether 7:1. $^1$H-NMR (DMSO-$d_6$): 1.05 ppm (t, 3H); 1.18 (t, 6H); 1.8–2.2 (m, 2H); 2.9 (m, 3H); 3.95 (m, 6H); 7.2 (m, 5H).

(c) α-Benzylacrylic acid ethyl ester: 4.0 g of KOH in 50 ml of ethanol are added at room temperature to 20 g of benzylmalonic acid diethyl ester in 40 ml of ethanol, the whole is stirred overnight at room temperature and concentrated by evaporation, 7.1 ml of water are added, and the whole is acidified with 6.3 ml of concentrated hydrochloric acid in an ice bath. The product is partitioned between water and ether, the organic phase is dried and the ether is distilled off. 12.9 ml of pyridine, 0.61 g of piperidine and 1.78 g of paraformaldehyde are added to the residue. The mixture is heated in an oil bath (130°) for 90 minutes, cooled, 220 ml of water are added and the whole is extracted three times with 75 ml of n-hexane. The combined organic phases are washed with water, 1N HCl, water, saturated NaHCO$_3$ solution and brine. The title compound is obtained by distillation. $^1$H-NMR (DMSO-d$_6$): 1.2 ppm (t, 3H); 3.6 (d, 2H), 4.1 (q, 2H); 5.6 (m, 1H); 6.15 (m, 1H); 7.25 (m, 5H).

Example 43:
N-(3-Benzyloxycarbonyl-2(R,S)-α-naphthoxypropionyl)-His-Cha£Val-n-butylamide Analogously to Example 24, the title compound is manufactured from 135 mg of 3-benzyloxycarbonyl-2(R,S)-α-naphthoxypropionic acid, 181 mg of H-His-Cha£Val-n-butylamide, 60 mg of HOBt and 105 mg of DCCI and purified by flash chromatography with solvent system B23. R$_f$(B23)=0.34.

The starting material is manufactured in the following manner:

(a) 3-Benzyloxycarbonyl-2-(R,S)-α-naphthoxypropionic acid: 0.35 g of sodium hydride (55% in oil) is added at 0° to 1.04 g of α-naphthoxysuccinic acid in 20 ml of DMF, the whole is stirred for 4 hours at room temperature, then 1.08 ml of benzyl bromide are added and the whole is stirred for 20 hours at 45°. The reaction mixture is concentrated by evaporation, dried in a high vacuum, taken up in 1N hydrochloric acid and extracted with ethyl acetate. The organic phase is dried over MgSO$_4$ and concentrated by evaporation. The residue is purified by flash chromatography with ethyl acetate/n-hexane/methanol 20:10:1, yielding the title compound in the form of a beige oil. R$_f$(S13)=0.48.

(b) α-Naphthoxysuccinic acid: 20.2 g of sodium hydride (55% in oil) are added in portions at 0°, while stirring, to 23 g of α-naphthol in 700 ml of DMF and 200 ml of THF. After 15 minutes at 10°, 29.6 g of bromosuccinic acid in 100 ml of DMF are added dropwise over a period of 30 minutes. The reaction mixture is stirred for 2 hours at room temperature and for 15 hours at 100°, THF being distilled off. The reaction mixture is then concentrated in a high vacuum and partitioned between 1N hydrochloric acid and ethyl acetate. The organic phase is dried, concentrated by evaporation and purified by flash chromatography with solvent system B10. The title compound is obtained in the form of a beige powder, m.p. 161°-162°, by crystallisation from ethyl acetate/n-hexane 1:2. R$_f$(S10)=0.17.

Example 44: N-(4-Carbamoyl-2(R)- and 2(S)-α-naphthoxybutyryl)-His-Cha£Val-n-butylamide Analogously to Example 24, the title compound is obtained in the form of a diastereoisomeric mixture from 14.8 mg of 4-carbamoyl-2(R,S)-α-naphthoxybutyric acid, 25.0 mg of H-His-Cha£Val-n-butylamide, 8.3 mg of HOBt and 14.4 mg of DCCI, and separated by flash chromatography with solvent system B29. R$_f$(B4)=0.35 (more rapid diastereoisomer) and R$_f$(B4)=0.25 (slower diastereoisomer).

The starting material is manufactured in the following manner:

(a) 4-Carbamoyl-2(R,S)-α-naphthoxybutyric acid: 1.49 ml of 1,8-diazabicyclo[5.4.0]undec-7-ene are added to a solution of 3 g of α-naphthoxymalonic acid diethyl ester (Example 36a) and 0.71 g of acrylamide in 5 ml of acetonitrile and the whole is stirred at room temperature for 24 hours. 25 ml of water are added to the reaction mixture, which is adjusted to pH 2 with 2N hydrochloric acid and extracted with ether. The ethereal phases are washed with water and brine, dried over sodium sulphate and concentrated by evaporation, leaving (2-carbamoylethyl)-α-naphthoxymalonic acid diethyl ester.

This ester is hydrolysed with lithium chloride and water in DMSO at 180° analogously to Example 35a and decarboxylated.

The crude acid is purified by chromatography with solvent system B11 and yields the pure title compound.

Example 45

The following are manufactured analogously to Example 24:

(a) N-(2(R)- and 2(S)-cyanomethyl-3-α-naphthylpropionyl)-His-Cha£Val-n-butylamide; separation by flash chromatography with eluant B28; R$_f$(B4)=0.43 (more rapid diastereoisomer) and R$_f$(B4)=0.38 (slower diastereoisomer).

(b) N-(Indolyl-2-carbonyl)-His-Cha£Val-n-butylamide; flash chromatography with eluant B23; R$_f$(B4)=0.43; R$_f$(B4)=0.59.

(c) N-Phenoxyacetyl-His-Cha£Val-n-butylamine; flash chromatography with eluant B23; R$_f$(B4)=0.48; R$_f$(S4)=0.62.

(d) N-(β-Naphthylcarbonyl)-His-Cha£Val-n-butylamide; flash chromatography with eluant B23; R$_f$(B4)=0.44; R$_f$(S4)=0.67.

(e) N-(α-Naphthoxyacetyl)-His-Cha£Val-n-butylamide; flash chromatography with eluant B23; R$_f$(B4)=0.52.

(f) N-(3-Benzyloxycarbonyl-2(R,S)-α-naphthylmethylpropionyl)-His-Cha£Val-n-butylamide; flash chromatography with eluant B3; R$_f$(B23)=0.21; R$_f$(S6)=0.23.

(g) N-(2(R,S)-Benzyl-4-oxopentanoyl)-His-Cha£Val-n-butylamide; R$_f$(B7)=0.43.

(h) N-(2(R,S)-Benzyl-4,4-dimethyl-3-oxopentanoyl)-His-Cha£Val-n-butylamide; R$_f$(B7)=0.35.

(i) N-(5-Dimethylamino-2(R)- and 2(S)-α-naphthylmethylpentanoyl)-His-Cha£Val-n-butylamide; R$_f$(B11)=0.63 (more rapid diastereoisomer) and R$_f$(B11)=0.18 (slower diastereoisomer).

(j) N-(2(R,S)-Benzyl-5,5-dimethyl-4-oxohexanoyl)-His-Cha£Val-methylamide; R$_f$(B7)=0.30.

(k) N-(2-(R,S)-tert.-Butylcarbamoyl-3-α-napthylpropionyl)-His-Cha£Val-n-butylamide; R$_f$(B5)=0.20; R$_f$(B7)=0.30.

Example 46: N-(3-Carboxy-2(R)- and 2(S)-α-naphthylmethylpropionyl)-His-Cha£Val-n-butylamide 60 mg of N-(3-benzyloxycarbonyl-2(R,S)-α-naphthylmethylpropionyl)-His-Cha£Val-n-butylamide (Example 45f) are dissolved in 6 ml of methanol and hydrogenated in the presence of 100 mg of palladium-on-carbon (10% Pd) until saturation is reached. The residue is separated by chromatography on 30 g of silica gel with methylene chloride/methanol/water (first 110:10:1, then 50:10:1). R$_f$(S10)=0.66 and R$_f$(N22)=0.37 (more

Example 47:
N-(Quinolyl-2-carbonyl)-N-methyl-His-Cha⊆Val-n-butylamide 41 mg of DCCI are added to 50 mg of H-Cha⊆Val-n-butylamide (Example 24c), 55 mg of N$^\alpha$-(quinolyl-2-carbonyl)-N$^\alpha$-methyl-L-histidine and 26 mg of HOBt in 2 ml of DMF in an ice bath. The whole is stirred for 6 hours in an ice bath and for 3 days at room temperature. After evaporating off the solvent in a high vacuum, the residue is heated for 60 minutes at 60° C. in 5 ml of a mixture of methanol/water/glacial acetic acid (94:3:3) and concentrated by evaporation again. The residue is purified by medium-pressure chromatography over a Lobar® prefabricated column, size B, with solvent system B26 and isolated by lyophilisation from tert.-butanol. R$_f$(B8)=0.36.

The starting material is manufactured in the following manner:

(a) N$^\alpha$-(Quinolyl-2-carbonyl-N$^\alpha$-methyl-L-histidine: 321.mg of N$^\alpha$-(quinolyl-2-carbonyl)-N$^\alpha$-methyl-L-histidine methyl ester are dissolved in 3 ml of THF and 1.42 ml of 1N NaOH are added at room temperature. After 1.5 hours the reaction mixture is neutralised with 1.42 ml of 1N HCl and concentrated to dryness by evaporation. R$_f$(B8)=0.02.

(b) N$^\alpha$-(Quinolyl-2-carbonyl)-N$^\alpha$-methyl-L-histidine methyl ester: 400 mg of N$^\alpha$-methyl-L-histidine methyl ester dihydrochloride, 298 mg of quinoline-2-carboxylic acid, 263 mg of HOBt, 0.531 ml of ethyl diisopropylamine and 418 mg of DCCI are stirred at room temperature for 5 days in 2 ml of DMF and then concentrated by evaporation. The residue is stirred for 1 hour at 60° in a mixture of methanol/water/glacial acetic acid (94:3:3), concentrated by evaporation again and purified by medium-pressure chromatography over a Lobar® prefabricated column with solvent system B31. R$_f$(B8)=0.63.

(c) N$^\alpha$-Methyl-L-histidine methyl ester dihydrochloride: 2 g of N$^\alpha$-methyl-L-histidine hydrochloride (Bachem AG, Bubendorf) are dissolved in 30 ml of methanol and, while cooling with an ice bath, 1.2 ml of SOCl$_2$ are added. The whole is stirred overnight at room temperature and then concentrated to dryness by evaporation. $^1$H-NMR (DMSO-d$_6$, TMS): 2.65 ppm (s, 3H); 3.45 (dd, 2H); 3.7 (s, 3H); 4.4 (m, 1H); 7.55 (s, H); 9.1 (s, 1H).

Example 48:
N-Methyl-N-(3-phenyl-2(S)-pivaloyloxypropionyl)-His-Cha⊆Val-n-butylamide Analogously to Example 47, the title compounds manufactured from 68 mg of N$^\alpha$-methyl-N$^\alpha$-(3-phenyl-(S)-pivaloyloxypropionyl)-L-histidine, 50 mg of H-Cha⊆Val-n-butylamide, 26 mg of HOBt and 41 mg of DCCI and purified by medium-pressure chromatography over a Lobar® prefabricated column with solvent system B26. R$_f$(B8)=0.29.

The starting material is manufactured in the following manner:

(a) N$^\alpha$-Methyl-N$^\alpha$-(3-phenyl-2(S)-pivaloyloxypropionyl)-L-histidine: Analogously to Example 47a, the corresponding methyl ester is hydrolysed with sodium hydroxide solution. R$_f$(B8)=0.01.

(b) N$^\alpha$-Methyl-N$^\alpha$-(3-phenyl-2(S)-pivaloyloxypropionyl)-L-histidine methyl ester: Analogously to Example 47b, the title compound is manufactured from N$^\alpha$-methyl-L-histidine methyl ester dihydrochloride and 3-phenyl-2(S)-pivaloyloxypropionic acid (Example 39a) and purified by flash chromatography with eluant N10, then medium-pressure chromatography (Lichroprep® Si60, 25–40 μm, eluant B33). R$_f$(B8)=0.59.

Example 49:
N-(Indolyl-2-carbonyl)-N-methyl-His-Cha⊆Val-n-butylamide hydrochloride Analogously to Example 47, the title compound is manufactured from 53 mg of N$^\alpha$-(indolyl-2-carbonyl)-N$^\alpha$-methyl-L-histidine, 50 mg of His-Cha⊆Val-n-butylamide, 26 mg of HOBt and 41 mg of DCCI, purified by medium-pressure chromatography (Lichroprep® Si60, 25–40 μm, eluant B33) and lyophilised from tert.-butanol. R$_f$(B8)=0.57.

The starting material N$^\alpha$-(indolyl-2-carbonyl)N$^\alpha$-methyl-L-histidine is manufactured analogously to Example 47a.

Example 50:
N-(Naphthalene-1,8-dicarbonyl)-Phe-Cha⊆Val-n-butylamide

Analogously to Example 1, the title compound is obtained from 110 mg of naphthalene-1,8-dicarbonyl-L-phenylalanine (Egypt. J. Chem. 24, 127 (1981)), 80 mg of H-Cha⊆Val-n-butylamide (Example 24c), 49 mg of HOBt and 81 mg of DCCI and purified by flash chromatography with solvent system N6. R$_f$(N7)=0.41; R$_f$(N6)=0.17.

Example 51:
N-(Indolyl-2-carbonyl)-Phe-Cha⊆Val-n-butylamide

A mixture of 39 mg of indole-2-carboxylic acid, 114 mg of H-Phe-Cha⊆Val-n-butylamide, 37 mg of HOBt and 66 mg of DCCI in 6 ml of DMF is stirred at room temperature for 24 hours. The crystallised DCH is filtered off and the filtrate is concentrated by evaporation. The crude product is purified by flash chromatography (100 g of silica gel 60, 40–63 μm, eluant N6). Concentration by evaporation of the combined product-containing fractions yields the title compound. R$_f$(B3)=0.46; R$_f$(S9)=0.89.

The starting material is manufactured in the following manner:

(a) H-Phe-Cha⊆Val-n-butylamide: 144 mg of Z-Phe-Cha⊆Val-n-butylamide are hydrogenated at normal pressure and room temperature in 5 ml of methanol/water 9:1 in the presence of 20 mg of palladium-on-carbon (10% Pd) until saturation is reached. The reaction mixture is filtered and the filtrate is stirred at room temperature with 5 ml of water. After evaporating off the solvent the title compound is obtained in the form of a colourless oil. R$_f$(B2)=0.62; R$_f$(S9)=0.85.

(b) Z-Phe-Cha⊆Val-n-butylamide: A mixture of 150 mg of Z-Phe-OH, 164 mg of H-Cha⊆Val-n-butylamide, 76 mg of HOBt and 134 mg of DCCI in 6 ml of DMF is stirred for 48 hours at room temperature. The DCH is filtered off and the filtrate is concentrated and dried in a high vacuum. The residue is separated by flash chromatography (185 g of silica gel 60, 40–63 μm, eluant N6). Concentration by evaporation of the combined product-containing fractions yields the title compound. R$_f$(B4)=0.80; R$_f$(N7)=0.37.

Example 52:
N-(Indolyl-2-carbonyl)-Nle-Cha£Val-n-butylamide

Analogously to Example 51, the title compound is obtained from 40 mg of indole-2-carboxylic acid, 110 mg of H-Nle-Cha£Val-n-butylamide, 38 mg of HOBt and 68 mg of DCCI in 6 ml of DMF and purified by flash chromatography with solvent system N7. $R_f$ (B2)=0.38; $R_f$(S9)=0.89.

The starting material is manufactured in the following manner:

(a) H-Nle-Cha£Val-n-butylamide is obtained analogously to Example 51a by hydrogenation of 144 mg of Z-Nle-Cha£Val-n-butylamide in 5 ml of methanol/water 9:1 in the presence of 20 mg of palladium-on-carbon (10% Pd). $R_f$(B2)=0.57; $R_f$(S9)=0.69.

(b) Z-Nle-Cha£Val-n-butylamide is manufactured analogously to Example 51b from 133 mg of Z-Nle-OH, 163 mg of H-Cha£Val-n-butylamine, 77 mg of HOBt and 134 mg of DCCI in 6 ml of DMF. $R_f$(B2)=0.80; $R_f$(N7)=0.31.

Example 53:
N-(Indolyl-2-carbonyl)-His-Cha£Val-3-dimethylaminopropylamide Analogously to Example 17, the title compound is obtained from 15 mg of indole-2-carboxylic acid, 43 mg of H-His-Cha£Val-3-dimethylaminopropylamide, 14 mg of HOBt and 25 mg of DCCI in 2 ml of DMF and purified by flash chromatography with solvent system B11. $R_f$(B1)=0.32; $R_f$(S9)=0.12.

The starting material is manufactured in the following manner:

(a) H-His-Cha£Val-3-dimethylaminopropylamide is manufactured, analogously to Example 16a, by hydrogenating 57 mg of Z-His-Cha£Val-3-dimethylaminopropylamide in 18 ml of methanol/water 9:1 in the presence of 15 mg of palladium-on-carbon (10% Pd) $R_f$ (B1)=0.085.

(b) Z-His-Cha£Val-3-dimethylaminopropylamide is obtained analogously to Example 16b from 136 mg of Z-His-OH, 167 mg of H-Cha£Val-3-dimethylaminopropylamide, 72 mg of HOBt and 128 mg of DCCI in 6 ml of DMF. $R_f$(B1)=0.32; $R_f$(S9)=0.14.

(c) H-Cha£Val-3-dimethylaminopropylamide: 247 mg of Z-Cha☆Val-3dimethylaminopropylamide are hydrogenated in 10 ml of methanol/water 9:1 in the presence of 40 mg of palladium-on-carbon (10% Pd) at normal pressure and room temperature until saturation is reached. The reaction mixture is filtered and the filtrate is stirred with 10 ml of water at room temperature. After evaporating off the solvent the title compound is obtained in the form of a colourless oil. $R_f$(B1)=0.13.

(d) Z-Cha☆Val-3-dimethylaminopropylamide: A mixture of 357 mg of Z-Cha☆Val-OH (Example 16i), 8.5 ml of DMF, 153 mg of HOBt and 206 mg of DCCI is left to stand for 24 hours at 0°. 337 mg of dimethyl-3-aminopropylamine are added to the mixture and the whole is stirred for 2 hours at 0° and for 39 hours at room temperature. The crystallised DCH is filtered off and the filtrate is concentrated and dried in a high vacuum. The title compound is obtained in the form of a colourless oil by flash chromatography of the residue (eluant system B4). $R_f$(B4)=0.32; $R_f$(N12)=0.24.

Example 54:
N-(Indolyl-2-carbonyl)-His-Cha£Val-2-morpholinoethylamide

Analogously to Example 17, the title compound is obtained from 26 mg of indole-2-carboxylic acid, 83 mg of H-His-Cha£Val-2-morpholinoethylamide, 25 mg of HOBt and 43 mg of DCCI in 4 ml of DMF and purified by flash chromatography with eluant system B4. $R_f$ (B2)=0.19; $R_f$(S9)=0.41.

The starting material is manufactured in the following manner:

(a) H-His-Cha£Val-2-morpholinoethylamide is manufactured, analogously to Example 16a, by hydrogenating 104 mg of Z-His-Cha£Val-2-morpholinoethylamide in 10 ml of methanol/water 9:1 in the presence of 40 mg of palladium-on-carbon (10% Pd) $R_f$ (B1)=0.43; $R_f$ (S9)=0.13.

(b) Z-His-Cha£Val-2-morpholinoethylamide is obtained analogously to Example 16b from 174 mg of Z-His-OH, 230 mg of H-Cha£Val-2-morpholinoethylamide, 92 mg of HOBt and 163 mg of DCCI in 8 ml of DMF. $R_f$(B2)=0.28; $R_f$(S9)=0.39.

(c) H-Cha£Val-2-morpholinoethylamide is manufactured, analogously to Example 53c, by hydrogenating 340 mg of Z-Cha☆Val-2-morpholinoethylamide in 10 ml of methanol/water 9:1 in the presence of 50 mg of palladium-on-carbon (10% Pd). $R_f$ (B1)=0.48; $R_f$ (S9)=0.21.

(d) Z-Cha☆Val-2-morpholinoethylamide is manufactured, analogously to Example 53d, from 267 mg of Z-Cha☆Val-OH, 98 mg 4-(2-aminoethyl)-morpholine, 115 mg of HOBt and 155 mg of DCCI in 7 ml of DMF. $R_f$(N1)=0.68; $R_f$(N6)=0.10.

Example 55:
N-(Indolyl-2-carbonyl)-His-Cha£Val-(5-tert.-butoxycarbonylamino-5-methoxycarbonylpentyl)-amide Analogously to Example 17, the title compound is obtained from 31 mg of indole-2-carboxylic acid, 124 mg of H-His-Cha£Val-(5-tert.-butoxycarbonylamino-5-methoxycarbonylpentyl)-amide, 29 mg of HOBt and 52 mg of DCCI in 3 ml of DMF and purified by flash chromatography with solvent system B23. $R_f$ (B4)=0.42; $R_f$(S9)=0.71.

The starting material is manufactured in the following manner:

(a) H-His-Cha£Val-(5-tert.-butoxycarbonylamino-5-methoxycarbonylpentyl)-amide is manufactured, analogously to Example 16a, by hydrogenating 143 mg of Z-His-Cha£Val-(5-tert.-butoxycarbonylamino-5-methoxycarbonylpentyl)-amide in 10 ml of methanol/water 9:1 in the presence of 25 mg of palladium-on-carbon (10% Pd) $R_f$(B4)=0.10; $R_f$(B11)=0.66.

(b) Z-His-Cha£Val-(5-tert.-butoxycarbonylamino-5-methoxycarbonylpentyl)-amide is obtained analogously to Example 16b from 197 mg of Z-His-OH, 349 mg of H-Cha£Val-(5-tert.-butoxycarbonylamino-5-methoxycarbonylpentyl)-amide, 104 mg of HOBt and 183 mg of DCCI in 11 ml of DMF. $R_f$(B4)=0.59.

(c) H-Cha£Val-(5-tert.-butoxycarbonylamino-5-methoxycarbonylpentyl)-amide is manufactured, analogously to Example 53c, by hydrogenating 469 mg of Z-Cha☆Val-(5-tert.-butoxycarbonylamino-5-methoxycarbonylpentyl)amide in 7 ml of methanol/water 9:1 in the presence of 100 mg of palladium-on-carbon (10% Pd) $R_f$(B4)=0.16.

(d) Z-Cha≃Val-(5-tert.-butoxycarbonylamino-5-methoxycarbonylpentyl)-amide is manufactured, analogously to Example 53d, from 446 mg of Z-Cha≃Val-OH, 320 mg of $N^\alpha$-tert.-butoxycarbonyl-L-lysine methyl ester, 153 mg of HOBt and 278 mg of DCCI in 14 ml of DMF. $R_f$(N3)=0.48; $R_f$(N10)=0.63.

Example 56:
N-(Indolyl-2-carbonyl)-His-Cha≃Val-(5-amino-5-carboxypentyl)-amide hydrochloride 102 mg of N-(indolyl-2-carbonyl)-His-Cha≃Val-(5-tert.-butoxycarbonylamino-5-methoxycarbonylpentyl)amide, 1.9 ml of 0.1N NaOH and 1 ml of water are stirred for 16 hours at room temperature in 5 ml of methanol. The reaction mixture is neutralised with 1.9 ml of 0.1N HCl, concentrated by evaporation and extracted with ethyl acetate. The extracts are concentrated by evaporation, 1.5 ml of trifluoroacetic acid are added and the whole is left to stand for 20 minutes at room temperature. The trifluoroacetic acid is evaporated off and the crude product is purified by flash chromatography (160 g of silica gel, 40–63 μm, eluant S4). The residue is taken up in 1N HCl, completely concentrated by evaporation, and lyophilised from tert.-butanol, yielding the title compound in the form of a light beige powder. $R_f$(B32)=0.76.

Example 57:
N-(α-Naphthoxyacetyl)-His-Cha≃Val-2-hydroxyethylamide

Analogously to Example 53, the title compound is manufactured from 59 mg of o-naphthoxyacetic acid, 146 mg of H-His-Cha≃Val-2-hydroxyethylamide, 45 mg of HOBt and 78 mg of DCCI and purified by flash chromatography with solvent system B4. $R_f$(B4)=0.30.

Example 58:
N-(3-Phenyl-2(S)-pivaloyloxypropionyl)-His-Leu≃Gly(R- and S-cyclohexylmethyl)-n-butylamide Analogously to Example 17, the title compounds are manufactured from 40 mg of 3-phenyl-2(S)-pivaloyloxypropionic acid (Example 39a), 70 mg of H-His-Leu≃Gly(R- and S-cyclohexylmethyl)-n-butylamide, 25 mg of HOBt and 39 mg of DCCI, purified by medium-pressure chromatography over a Lobar ® prefabricated column with solvent system B31 and isolated by lyophilisation from tert.-butanol. $R_f$(B8)=0.64 (diastereoisomer A) and $R_f$(B8)=0.55 (diastereoisomer B).

The starting material is manufactured in the following manner:

(a) H-His-Leu≃Gly(R- and S-cyclohexylmethyl)-n-butylamide are obtained, analogously to Example 16a, by hydrogenating Z-His-Leu≃Gly(R- and S-cyclohexylmethyl)-n-butylamide. $R_f$(B8)=0.17 (diastereoisomer A) and $R_f$(B8)=0.11 (diastereoisomer B).

(b) Z-His-Leu≃Gly(R- and S-cyclohexylmethyl)-n-butylamide are obtained analogously to Example 16b from Z-His-OH and H-Leu≃Gly(R- and S-cyclohexylmethyl)-n-butylamide and purified by flash chromatography with eluant N10. $R_f$(N8)=0.33 (diastereoisomer A) and $R_f$(N8)=0.43 (diastereoisomer B).

(c) H-Leu≃Gly(R- and S-cyclohexylmethyl)-n-butylamide are obtained analogously to Example 16k by hydrogenating Z-Leu≃Gly(R- and S-cyclohexylmethyl)-n-butylamide. $R_f$(B10)=0.64 (diastereoisomer A) and $R_f$(B10)=0.61 (diastereoisomer B).

(d) Z-Leu≃Gly(R- and S-cyclohexylmethyl)-n-butylamide are obtained analogously to Example 16j from Z-Leu≃Gly(R- and S-cyclohexylmethyl)-OH and n-butylamine and separated by flash chromatography with eluant N4. $R_f$(N3)=0.65 (diastereoisomer A) and $R_f$(N3)=0.59 (diastereoisomer B).

(e) Z-Leu≃Gly(R- and S-cyclohexylmethyl)-H (3-[3-benzyloxycarbonyl-2,2-dimethyl-4(S)-isobutyl-1,3-oxazolidin-5(S)-yl]-2(R,S)-cyclohexylmethylpropionic acid) is manufactured analogously to Example 16i by hydrolysis of the corresponding methyl ester. $R_f$(N4)=0.05 (diastereoisomeric mixture).

(f) 3-(3-Benzyloxycarbonyl-2,2-dimethyl-4(S)-isobutyl-1,3-oxazolidin-5(S)-yl)-2(R,S)-cyclohexylmethylpropionic acid methyl ester is manufactured analogously to Example 1d from compound (XXV) and 3-cyclohexylpropionic acid methyl ester and purified by medium-pressure chromatography over a Lobar ® prefabricated column with n-hexane/ethyl acetate 19:1. $R_f$(N5)=0.14 and 0.17.

(g) 3-Cyclohexylpropionic acid methyl ester: 20 g of cyclohexylpropionic acid are left to stand overnight at room temperature in 200 ml of 5N HCl in methanol. The solvent is evaporated off and the residue is taken up in ether, washed with saturated NaHCO₃ solution and brine and dried. Distillation at 121°–125°/2.0–2.5×10⁻² bar yields the title compound.

Example 59:
N-(3-Phenyl-2(S)-pivaloyloxypropionyl)-His-Leu≃Gly-(R- and S-α-decahydronaphthyl)-n-butylamide Analogously to example 17, the title compounds are manufactured from 29 mg of 3-phenyl-2(S)-pivaloyloxypropionic acid (Example 39a), 55 mg of H-His-Leu≃Gly(R- and S-α-decahydronaphthyl)-n-butylamide, 18 mg of HOBt and 28 mg of DCCI and purified by medium-pressure chromatography over a Lobar ® prefabricated column with solvent system B31. $R_f$(B8)=0.53 (diastereoisomer A) and $R_f$(B8)=0.45 (diastereoisomer B).

The starting materials are manufactured in the following manner:

(a) H-His-Leu≃Gly(R- and S-o-decahydronaphthyl)-n-butylamide are obtained analogously to Example 16a by hydrogenating Z-His-Leu≃Gly(R- and S-α-decahydronaphthyl)-n-butylamide. $R_f$(B8)=0 (both diastereoisomers).

(b) Z-His-Leu≃Gly(R- and S-o-decahydronaphthyl)-n-butylamide are obtained analogously to Example 16b from Z-His-OH and H-Leu≃Gly(R- and S-α-decahydronaphthyl)-n-butylamide and purified by medium-pressure chromatography with eluant B31. $R_f$(B8)=0.59 (diastereoisomer A) and $R_f$(B8)=0.48 (diastereoisomer B).

(c) H-Leu≃Gly(R- and S-α-decahydronaphthyl)-n-butylamide are obtained analogously to Example 16k by hydrogenating Z-Leu≃Gly(R- and S-α-decahydronaphthyl)-n-butylamide and purified by medium-pressure chromatography with eluant N8 followed by pure methanol. $R_f$(B8)=0 (both diastereoisomers).

(d) Z-Leu≃Gly(R- and S-α-decahydronaphthyl)-n-butylamide are obtained analogously to Example 16j from Z-Leu≃Gly(R,S-α-decahydronaphthyl)-OH and n-butylamine and purified by flash chromatography with eluant N4. $R_f$(N3)=0.68 (diastereoisomer A) and $R_f$(N3)=0.61 (diastereoisomer B).

(e) Z-Leu≃Gly(R,S,-α-decahydronaphthyl)-OH (3-[3-benzyloxycarbonyl-2,2-dimethyl-4(S)-isobutyl-1,3-oxazolidin-5(S)-yl]-2(R,S)-α-decahydronaphthylpropionic acid) is manufactured analogously to Example 16i by hydrolysis of the corresponding methyl ester and purified by medium-pressure chromatography with n-hexane/ethyl acetate 19:1. $R_f$(N4)=0.13 and 0.18.

(f) 3-[3-Benzyloxycarbonyl-2,2-dimethyl-4(S)-isobutyl-1,3-oxazolidin-5(S)-yl]-2(R,S)-α-decahydronaphthylpropionic acid methyl ester is manufactured analogously to Example 1d from compound (XXV) and α-decahydronaphthylacetic acid methyl ester and purified by medium-pressure chromatography with n-hexane/ethyl acetate 19:1.

(g) α-Decahydronaphthylacetic acid methyl ester is manufactured analogously to Example 58g by esterifying α-decahydronaphthylacetic acid. $^1$H-NMR (DMSO-$d_6$, TMS): 3.58 ppm (s, 3H) and others.

(h) α-Decahydronaphthylacetic acid: 25 g of α-naphthylacetic acid are dissolved in 120 ml of water and 134 ml of 1N sodium hydroxide solution and hydrogenated for 31 hours at room temperature and normal pressure in the presence of 1.3 g of platinum/rhodium catalyst ($PtO_2.H_2O$-$Rh_2O_3$=54:46). The catalyst is filtered off and the filtrate is acidified with concentrated hydrochloric acid to pH 1 and extracted with ether. The title compound is obtained by drying and concentrating by evaporation the ethereal extract.

Example 60:
N-(3-phenyl-2(S)-pivaloyloxypropionyl)-His-Leu$^c$Gly-(R- and S-dimethylamino)-n-butylamide Analogously to Example 17, the title compounds are manufactured from 20 mg of 3-phenyl-2(S)-pivaloyloxypropionic acid (Example 39a), 27 mg of H-His-Leu$^c$-Gly(R- and S-dimethylamino)-n-butylamide, 12 mg of HOBt and 20 mg of DCCI, purified by medium-pressure chromatography over a Lobar® prefabricated column with solvent system B5 and isolated by lyophilisation from tert.-butanol. $R_f$ (B8)=0.36 (diastereoisomer A) and $R_f$(B8)=0.30 (diastereoisomer B).

The starting materials are manufactured in the following manner:

(a) H-His-Leu$^c$Gly(R- and S-dimethylamino)-n-butylamide are obtained by hydrogenating Z-His-Leu$^c$-Gly(R- and S-dimethylamino)-n-butylamide analogously to Example 16a. $R_f$(B8)=0.01 (both diastereoisomers).

(b) Z-His-Leu$^c$Gly(R- and S-dimethylamino)-n-butylamide are obtained analogously to Example 16b from Z-His-OH and H-Leu$^c$Gly(R- and S-dimethylamino)-n-butylamide and purified by medium-pressure chromatography with eluant B33. $R_f$ (B8)=0.36 (diastereoisomer A) and $R_f$(B8)=0.15 (diastereoisomer B).

(c) H-Leu$^c$Gly(R- and S-dimethylamino)-n-butylamide are obtained by hydrogenating Z-Leu$^c$Gly(R,S-dimethylamino)-n-butylamide analogously to Example 16k and separation by medium-pressure chromatography with eluant B33. $R_f$(B8)=0.28 (diastereoisomer A) and $R_f$(B8)=0.19 (diastereoisomer B).

(d) Z-Leu$^c$Gly(R,S-dimethylamino)-n-butylamide is obtained analogously to Example 16j from Z-Leu$^c$Gly-(R,S-dimethylamino)-OH and n-butylamine and purified by flash chromatography with eluant methylene chloride/methanol/concentrated ammonia 500:10:1. $R_f$(B31)=0.91 and 0.95.

(e) Z-Leu$^c$Gly(R,S-dimethylamino)-OH (3-[3-benzyloxycarbonyl-2,2-dimethyl-4(S)-isobutyl-1,3-oxazolidin-5(S)-yl]-2(R,S)-dimethylaminopropionic acid) is manufactured analogously to Example 16j by hydrolysis of the corresponding ethyl ester and purified by medium-pressure chromatography with eluant N8. $R_f$(N3)=0.21 and 0.10.

(f) 3-(3-Benzyloxycarbonyl-2,2-dimethyl-4(S)-isobutyl-1,3-oxazolidin-5(S)-yl)-2(R,S)-dimethylaminopropionic acid ethyl ester is manufactured analogously to Example 1d from compound (XXV) and dimethylaminoacetic acid ethyl ester and purified by medium-pressure chromatography with eluant N3. $R_f$(N3)=0.52 and 0.35.

Example 61:
N-(Indolyl-2-carbonyl)-His-Leu$^c$Val-4-[tris-(tert.-butyldimethylsilyloxymethyl)-methylcarbamoyl]-butylamide 21 mg of indole-2-carboxylic acid, 20 mg of HOBt and 23 μl of ethyldiisopropylamine are cooled to 0° in 2 ml of DMF. After the addition of 116 mg of H-His-Leu$^c$Val-4-[tris-(tert.-butyldimethylsilyloxymethyl)-methylcarbamoyl]-butylamide and 34 mg of DCCI the whole is stirred for 24 hours while cooling with ice and then for 2 days at room temperature. The crystalline DCH is filtered off with suction and the filtrate is concentrated in a high vacuum. The residue is purified by flash chromatography with solvent system B23. Lyophilisation in 20 ml of tert.-butanol yields the title compound in the form of a slightly yellowish lyophilisate. $R_f$(B4)=0.49.

The starting material is manufactured in the following manner:

(a) H-His-Leu$^c$Val-4-[tris-(tert.-butyldimethylsilyloxymethyl)-methylcarbamoyl]-butylamide is obtained from the corresponding N-benzyloxycarbonyl compound by hydrogenation analogously to Example 4a. $R_f$(B4)=0.11.

(b) Z-His-Leu$^c$Val-4-[tris-(tert.-butyldimethylsilyloxymethyl)-methylcarbamoyl]-butylamide: Analogously to Example 61, the title compound is manufactured from 58 mg of Z-His-OH, 155 mg of H-Leu$^c$Val-4-[tris-(tert.-butyldimethylsilyloxymethyl)methylcarbamoyl]-butylamide (manufactured according to EP-A 143 746), 35 μl of ethyldiisopropylamine, 31 mg of HOBt and 54 mg of DCCI in 4 ml of DMF and purified by flash chromatography with eluant B23. $R_f$(B4)=0.42.

Example 62:
N-(Indolyl-2-carbonyl)-His-Leu$^c$Val-4-[tris-(hydroxymethyl)-methylcarbamoyl]-butylamide 36 mg of N-(indolyl-2-carbonyl)-His-Leu$^c$Val-4-[tris-(tert.-butyldimethylsilyloxymethyl)-methylcarbamoyl]-butylamide and 2 ml of acetic acid/water 2:1 are stirred for 2 hours at room temperature and then concentrated by evaporation. The residue is purified by flash chromatography with solvent system B11 and yields the title compound in the form of a white powder. $R_f$(B11)=0.27.

Example 63:
N-(1-Benzylindolyl-3-carbonyl)-His-Leu$^c$Val-2-picolylamide

Analogously to Example 4, the title compound is obtained from 30 mg of N-benzylindole-3-carboxylic acid, 45 mg of H-His-Leu$^c$Val-2-picolylamide, 19 mg of HOBt and 30 mg of DCCI and purified by flash chromatography with solvent system B7. $R_f$(B7)=0.31; $R_f$(B9)=0.43.

The starting materials are manufactured in the following manner:

(a) H-His-Leu≏Val-2-picolylamide is obtained, analogously to Example 1g, by hydrogenating 430 mg of Z-His-Leu≏Val-2-p:colylamide in the presence of 50 mg of palladium-on-carbon (10%). $R_f$ (B1)=0.18; $R_f$ (B7)=0.12.

(b) Z-His-Leu≏Val-2-picolylamide is obtained analogously to Example 1 from 225 mg of Z-His-OH, 350 mg of H-Leu≏Val-2-picolylamide, 130 mg of HOBt and 218 mg of DCCI and purified by flash chromatography with solvent system B7. $R_f$(B7)=0.30; $R_f$(B11)=0.63.

(c) H-Leu≏Val-2-picolylamide is obtained, analogously to Example 1g, by hydrogenating 1.69 g of Z-Leu≏Val-2-picolylamide in the presence of 170 mg of palladium-on-carbon (10 %). $R_f$(B7)=0.25.

(d) Z-Leu≏Val-2-picolylamide is obtained analogously to Example 1 from 1.50 g of Z-Leu≏Val-OH, 0.76 ml of 2-aminomethylpyridine, 680 mg of HOBt and 1.070 g of DCCI and purified by flash chromatography with solvent system N7. $R_f$(N7)=0.32.

Example 64

The following are manufactured analogously to Example 8:

(a) N-(Indolyl-2-carbonyl)-His-Leu≏Val-n-pentylamide; flash chromatography with eluant B4; $R_f$(B4)=0.42.

(b) N-(Indolyl-2-carbonyl)-His-Leu≏Val-cyclohexylmethylamide; flash chromatography with eluant B23; $R_f$(B4)=0.34.

(c) N-(Indolyl-2-carbonyl)-His-Leu≏Val-5-hydroxypentylamide; flash chromatography with eluant B4; $R_f$(B4)=0.18.

(d) N-(α-Naphthoxyacetyl)-His-Leu≏Val-2-hydroxyethylamide; flash chromatography with eluant B4; $R_f$(B4)=0.27.

Example 65

The following are manufactured analogously to Example 4:

(a) N-(α-Naphthoxyacetyl)-Phe-Leu≏Val-n-butylamide; flash chromatography with eluant N10; $R_f$(N10)=0.15.

(b) N-Methyl-N-(α-naphthoxyacetyl)-Phe-Leu≏Val-n-butylamide; flash chromatography with eluant N7; $R_f$(N7)=0.26.

Example 66

The following can be manufactured in accordance with one of the preceding Examples:

N-[2-(2-amino-2-methylpropionyloxy)-3-α-naphthylpropionyl]-His-Cha≏Val-n-butylamide;
N-(2-acetoacetoxy-3-α-naphthylpropionyl)-His-Cha≏Val-n-butylamide;
N-(2-cyano-3-α-naphthylpropionyl)-His-Cha≏Val-n-butylamide;
N-(2-acetyl-3-α-naphthylpropionyl)-His-Cha≏Val-n-butylamide;
N-(2-acetonyl-3-α-naphthylpropionyl)-His-Cha≏Val-n-butylamide;
N-(5-dimethylamino-2-α-naphthoxypentanoyl)-His-Cha≏Val-n-butylamide;
N-(4-carboxy-2-α-naphthoxybutyryl)-His-Cha≏Val-n-butylamide;
N-(2-α-naphthoxy-4-oxopentanoyl)-His-Cha≏Val-n-butylamide;
N-(cyano-α-naphthoxyacetyl)-His-Cha≏Val-n-butylamide;
N-(3-phenyl-2-pivaloyloxypropionyl)-His-Cha≏Gly(dimethylamino)-n-butylamide;
N-(2-benzyl-5,5-dimethyl-4-oxohexanoyl)-His-Cha≏Gly(dimethylamino)-n-butylamide;
N-(3-phenyl-2-pivaloyloxypropionyl)-His-Cha≏Val-2-(4-imidazolyl)-ethylamide;
N-(2-benzyl-5,5-dimethyl-4-oxohexanoyl)-His-Cha≏Val-2-(4-imidazolyl)-ethylamide;
N-(3-phenyl-2-pivaloyloxypropionyl)-His-Cha≏Val-2-[2-(4-imidazolyl)-ethylamino]-ethylamide;
N-(2-benzyl-5,5-dimethyl-4-oxohexanoyl)-His-Cha≏Val-2-[2-(4-imidazolyl)-ethylamino]-ethylamide;
N-(2-benzyl-5,5-dimethyl-4-oxohexanoyl)-His-Cha≏Val-4-carboxybutylamide;
N-[2-(2-dimethylaminoethylcarbamoyl)-3-phenylpropionyl]-His-Cha≏Val-4-carboxybutylamide;
N-(2-dimethoxyphosphoryl-3-phenylpropionyl)-His-Cha≏Val-4-carboxybutylamide;
N-[2-(5-amino-5-carboxypentylcarbamoyl)-3-phenylpropionyl]-His-Cha≏Val-n-butylamide;
N-(2-dimethylaminomethyl-3-α-naphthylpropionyl)-His-Cha≏Val-4-carboxybutylamide;
N-(2-benzyl-5-dimethylamino-4-oxopentanoyl)-His-Cha≏Val-methylamide;
N-(2-acetoxy-4-phenylbutyryl)-His-Cha≏Val-n-butylamide;
N-(2-cyanomethyl-4-phenylbutyryl)-His-Cha≏Val-n-butylamide;
N-(2-ethylaminocarbonyloxy-4-phenylbutyryl)-His-Cha≏Val-n-butylamide;
N-(3-α-naphthyl-2-neopentyloxypropionyl)-His-Cha≏Val-n-butylamide;
N-(2-benzyl-5,5-dimethyl-4-oxohexanoyl)-His-Cha≏Gly-(cyclohexylmethyl)-n-butylamide;
N-[4,4-dimethyl-3-oxo-2-(2-phenylethyl)-pentanoyl]-His-Cha≏Val-n-butylamide;
N-(2-dimethoxyphosphoryl)-4-phenylbutyryl)-His-Cha≏Val-n-butylamide;
N-(2-diethoxyphosphorylmethyl-4-phenylbutyryl)-His-Cha≏Val-n-butylamide;
N-[5,5-dimethyl-4-oxo-2-(2-phenylethyl)-hexanoyl]-His-Cha≏Val-n-butylamide;
N-(2-tert.-butylcarbamoyl-4-phenylbutyryl)-His-Cha≏Val-n-butylamide;
N-(2-tert.-butylcarbamoyl-3-phenylpropionyl)-His-Cha≏Val-n-butylamide;
N-(2-tert.-butylcarbamoyl-3-o-naphthylpropionyl)-His-Cha≏Val-methylamide;
N-(2-benzyl-5,5-dimethyl-4-oxohexanoyl)-His-Cha≏Val-methylamide;
N-(2-benzyl-5,5-dimethyl-4-oxohexanoyl)-His-Leu≏Gly-(cyclohexylmethyl)-n-butylamide;
N-(2-benzyl-4,4-dimethyl-3-oxopentanoyl)-His-Leu≏Gly-(cyclohexylmethyl)-n-butylamide;
N-(2-tert.-butylcarbamoyl-3-phenylpropionyl)-His-Leu≏Gly(cyclohexylmethyl)-n-butylamide.

Example 67: Gelatin solution

A sterile-filtered aqueous solution of N-(2(R,S)-benzyl-5,5-dimethyl-4-oxohexanoyl)-His-Cha≏Val-n-butylamide is mixed under aseptic conditions, while heating, with a sterile gelatin solution that contains phenol as preservative, such that 1.0 ml of solution has the following composition:

| | |
|---|---|
| N-(2(R,S)-benzyl-5,5-dimethyl-4-oxohexanoyl)-His-Cha-≏Val-n-butylamide | 3 mg |

| gelatin | 150.0 mg |
| phenol | 4.7 mg |
| distilled water up to | 1.0 ml |

The mixture is introduced under aseptic conditions into 1.0 ml phials.

Example 68: Sterile dry substance for injection 5 mg of N-(2(R,S)-benzyl-5,5-dimethyl-4-oxohexanoyl)-His-Cha≤Val-n-butylamide are dissolved in 1 ml of an aqueous solution with 20 mg of mannitol. The solution is sterile-filtered and introduced under aseptic conditions into a 2 ml ampoule, deep-frozen and lyophilised. Before use, the lyophilisate is dissolved in 1 ml of distilled water or 1 ml of physiological salt solution. The solution is administered intramuscularly or intravenously. This formulation can also be introduced into double-chambered injection ampoules.

Example 69: Nasal spray 500 mg of finely ground (<5.0 μm) of N-(2(R,S)-benzyl-5,5-dimethyl-4-oxohexanoyl)-His-Cha≤Val-n-butylamide are suspended in a mixture of 3.5 ml of "Myglyol 812" and 0.08 g of benzyl alcohol. This suspension is introduced into a container with a metering valve. 5.0 g of "Freon 12" are introduced into the container under pressure through the valve. By shaking, the "Freon" is dissolved in the Myglyolbenzyl alcohol mixture. This spray container contains approximately 100 single doses, which can be administered individually.

We claim:

1. Compounds of the formula

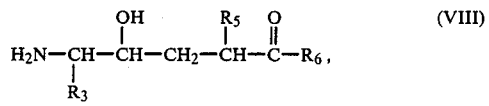

(VIII)

wherein $R_3$ represents hydrogen, hydroxy-lower alkyl, etherified or esterified hydroxy-lower alkyl, cycloalkyl, cycloalkyl-lower alkyl, bicycloalkyl-lower alkyl, tricycloalkyl-lower alkyl, aryl or aryl-lower alkyl, $R_5$ represents lower alkyl having 2 or more carbon atoms, hydroxy-lower alkyl, etherified or esterified hydroxy-lower alkyl, cycloalkyl, cycloalkyl-lower alkyl, bicycloalkyl, bicycloalkyl-lower alkyl, tricycloalkyl, tricycloalkyl-lower alkyl, aryl, aryl-lower alkyl, carbamoyl, substituted carbamoyl, amino, substituted amino, hydroxy, substituted hydroxy, mercapto or substituted mercapto and $R_6$ represents substituted amino with the exception of an amino residue derived from an alpha-amino acid, and salts of such compounds having salt-forming groups.

2. A compound according to claim 1 selected from the group consisting of H-CHa≤Val-methylamide, H-Cha≤Val-n-butylamide, H-Cha≤Val-3-dimethylaminopropylamide, H-Cha≤Val-2-morpholinoethylamide and H-Cha≤Val-(5-tert.-butoxycarbonylamino-5-methoxycarbonylpentyl)amide.

3. A compound according to claim 1, wherein $R_3$ represents cycloalyl-lower alkyl.

4. A compound according to claim 1, wherein $R_3$ represents cyclohexylmethyl.

* * * * *